(12) United States Patent
Pechenov et al.

(10) Patent No.: US 11,173,124 B2
(45) Date of Patent: Nov. 16, 2021

(54) ORAL DELIVERY OF GLP-1 PEPTIDE ANALOGS

(71) Applicant: MEDIMMUNE LIMITED, Cambridge (GB)

(72) Inventors: Sergei Pechenov, Gaithersburg, MD (US); Puneet Tyagi, Gaithersburg, MD (US); Janardhanan Anand Subramony, Gaithersburg, MD (US)

(73) Assignee: MedImmune Limited, Cambridge (GB)

( * ) Notice: Subject to any disclaimer, the term of this patent is extended or adjusted under 35 U.S.C. 154(b) by 0 days.

(21) Appl. No.: 16/760,250

(22) PCT Filed: Oct. 30, 2018

(86) PCT No.: PCT/IB2018/058514
§ 371 (c)(1),
(2) Date: Apr. 29, 2020

(87) PCT Pub. No.: WO2019/087083
PCT Pub. Date: May 9, 2019

(65) Prior Publication Data
US 2020/0323782 A1   Oct. 15, 2020

Related U.S. Application Data

(60) Provisional application No. 62/579,186, filed on Oct. 31, 2017.

(51) Int. Cl.
*A61K 9/28* (2006.01)
*A61K 9/20* (2006.01)
*A61K 9/48* (2006.01)
*A61K 9/50* (2006.01)
*A61K 38/26* (2006.01)

(52) U.S. Cl.
CPC .......... *A61K 9/2846* (2013.01); *A61K 9/2013* (2013.01); *A61K 9/2027* (2013.01); *A61K 9/4808* (2013.01); *A61K 9/4858* (2013.01); *A61K 9/4891* (2013.01); *A61K 9/5026* (2013.01); *A61K 9/5078* (2013.01); *A61K 38/26* (2013.01)

(58) Field of Classification Search
CPC .. A61K 9/2846; A61K 9/2013; A61K 9/2027; A61K 9/4808; A61K 9/4858; A61K 9/4891; A61K 9/5026; A61K 9/5078; A61K 38/26
See application file for complete search history.

(56) References Cited

FOREIGN PATENT DOCUMENTS

| EP | 1613355 A1 | 1/2006 |
|---|---|---|
| EP | 2679270 B1 | 11/2016 |
| WO | 2004/091667 A1 | 10/2004 |
| WO | 2013/148966 A1 | 10/2013 |
| WO | 2014/191545 A1 | 12/2014 |
| WO | 2019/087083 A2 | 5/2019 |

OTHER PUBLICATIONS

Araujo, F. et al., "Oral Delivery of Glucagon-Like Peptide-1 and Analogs: Alternatives for Diabetes Control?" Journal of Diabetes Science and Technology, Nov. 1, 2012; vol. 6, No. 6, pp. 1486-1497.
Pan, C.Q., et al., "Design of a Long Acting Peptide Functioning as Both a Glucagon-like Peptide-1 Receptor Agonist and a Glucagon Receptor Antagonist," The Journal of Biological Chemistry, Feb. 27, 2006, vol. 281, No. 18; pp. 12506-12515.
Zhang, L., et al., "Converting Peptides into Drug Leads by Lipidation," Current Medicinal Chemistry, vol. 19, No. 11, Mar. 1, 2012, pp. 1602-1618.
Supplementary European Search Report, dated Jul. 8, 2021, EP18874364.

*Primary Examiner* — Robert A Wax
*Assistant Examiner* — Olga V. Tcherkasskaya

(57) ABSTRACT

The present invention provides formulations for oral administration of GLP-1 peptide analogs, methods of making such formulations, and methods of treatment using such formulations.

41 Claims, 28 Drawing Sheets
Specification includes a Sequence Listing.

FIG. 1A
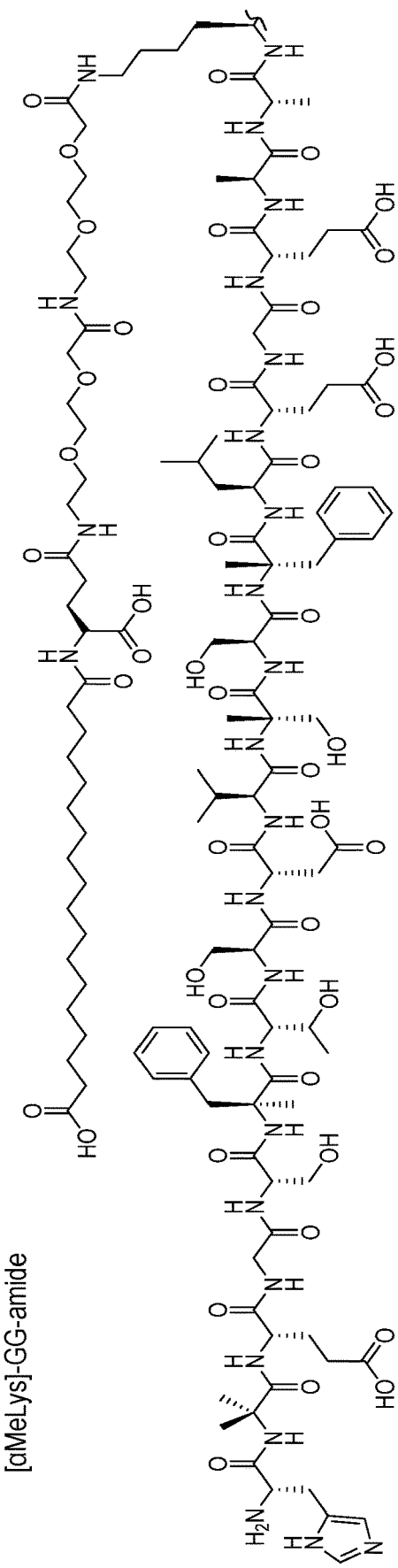
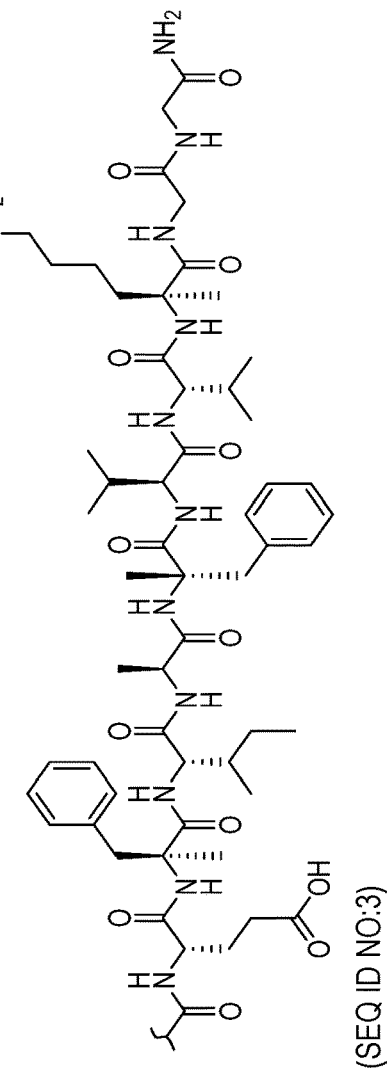
Free-H-[AIB]-EGS-[αMePhe]-TSDV-[αMeSer]-S-[αMePhe]-LEGEAAK[(PEG$_2$)$_2$-γE-Stearate]-E-[αMePhe]-IA-[αMePhe]-VV-[αMeLys]-GG-amide
Chemical Formula: C$_{183}$H$_{286}$N$_{38}$O$_{57}$
Molecular Weight: 3930.51
(SEQ ID NO:3)

FIG. 1B
Free-H-[AIB]-EGS-[aMePhe]-TSDV-[aMeSer]-S-[aMePhe]-LEGEAAK[(PEG2)2-yE-Stearate]-EFIA-[aMePhe]-LEGEAAK[(PEG2)2-yE-Stearate]-EFIA-[aMePhe]-VV-[aMeLys]-GG-amide
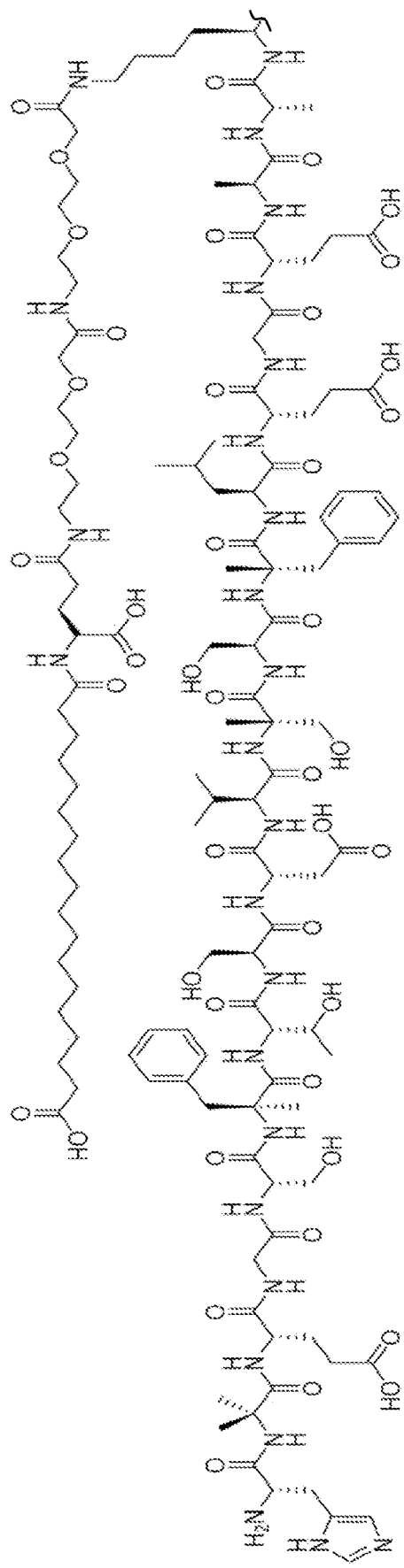
Chemical Formula: $C_{162}H_{284}N_{38}O_{57}$
Molecular Weight: 3916.42
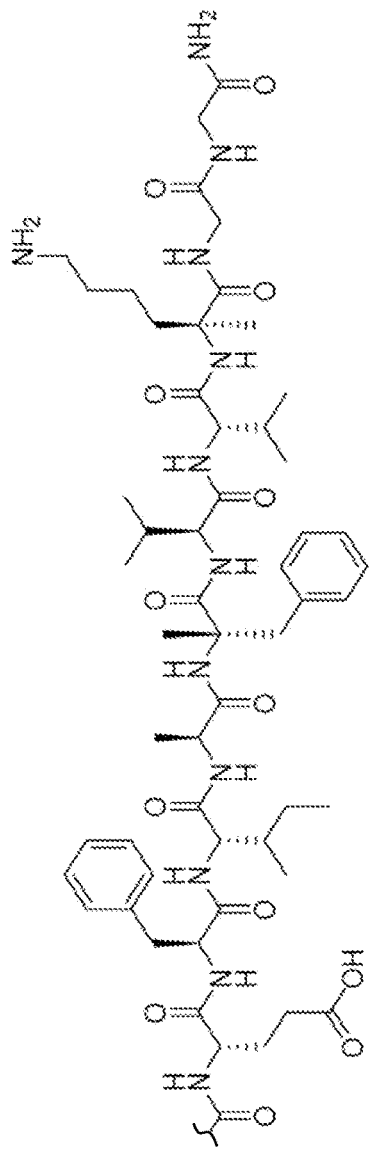
(SEQ ID NO:4)

FIG. 1C
Free-H-[AIB]-EGS-[αMePhe]-TSDVSK[(PEG₂)₂-γE-Lauroyl]-YLEGEAA-[αMeLys]-EFIAK[(PEG₂)₂-γE-Lauroyl]-VVEGG-amide
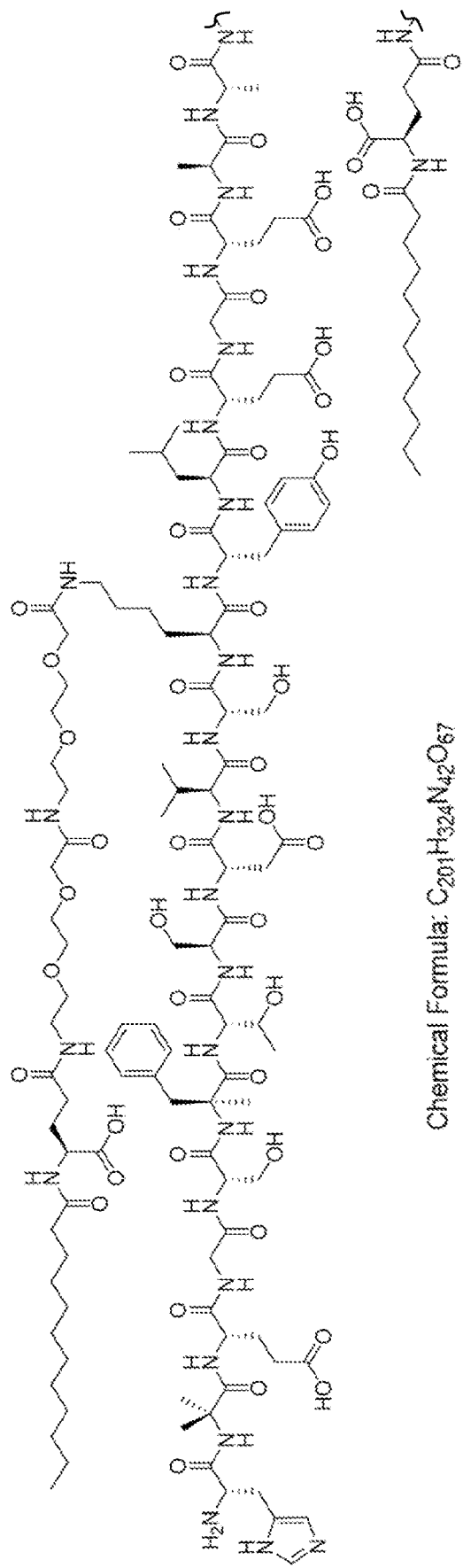
Chemical Formula: $C_{201}H_{324}N_{42}O_{67}$
Molecular Weight: 4400.96
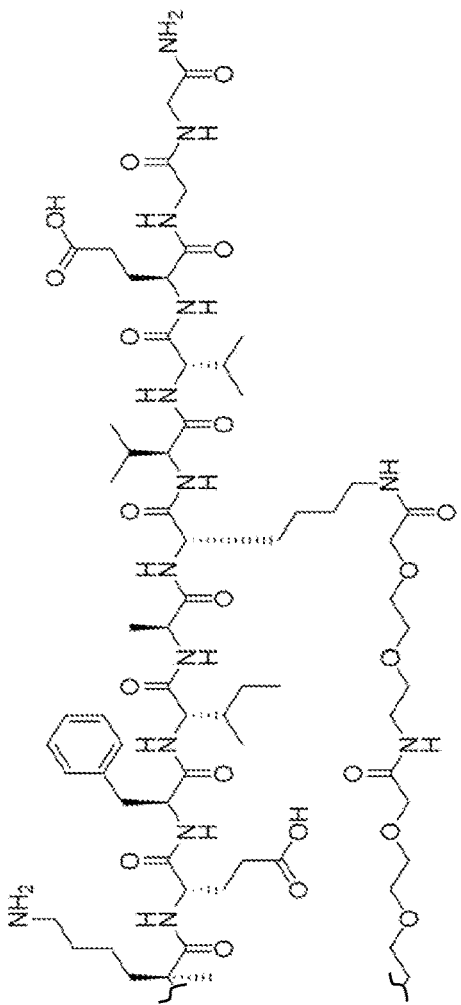
(SEQ ID NO:5)

Free-H-[AIB]-EGS-[αMePhe]-TSDV-[αMeSer]-SK[(PEG₂)₂-γE-Lauroyl]-LEGEAA-[αMeLys]-EFIAK[(PEG₂)₂-γE-Lauroyl]-VVEGG-amide Chemical Formula: C₁₉₆H₃₂₂N₄₂O₆₇
Molecular Weight: 4338.90

(SEQ ID NO:6)

Free-H-[AIB]-EGS-[αMePhe]-TSDVSK[(PEG$_2$)$_2$-γE-Lauroyl]-YLEGEAA-[αMeLys]-EFIAWK[(PEG$_2$)$_2$-γE-Lauroyl]-VEGG-amide Chemical Formula: C$_{207}$H$_{325}$N$_{43}$O$_{67}$
Molecular Weight: 4488.04

(SEQ ID NO:7)

FIG. 1F
Free-H-[AIB]-EGS-[αMePhe]-TSDK[(PEG2)2-γE-Lauroyl]-SSYLEGEAA-[αMeLys]-EFIK[(PEG2)2-γE-Lauroyl]-WVVEGG-amide
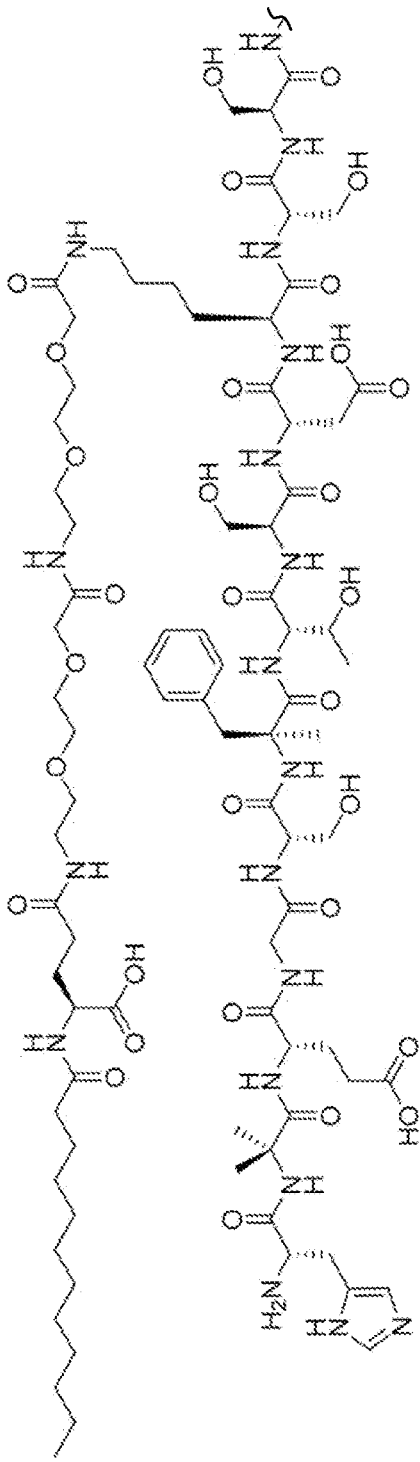
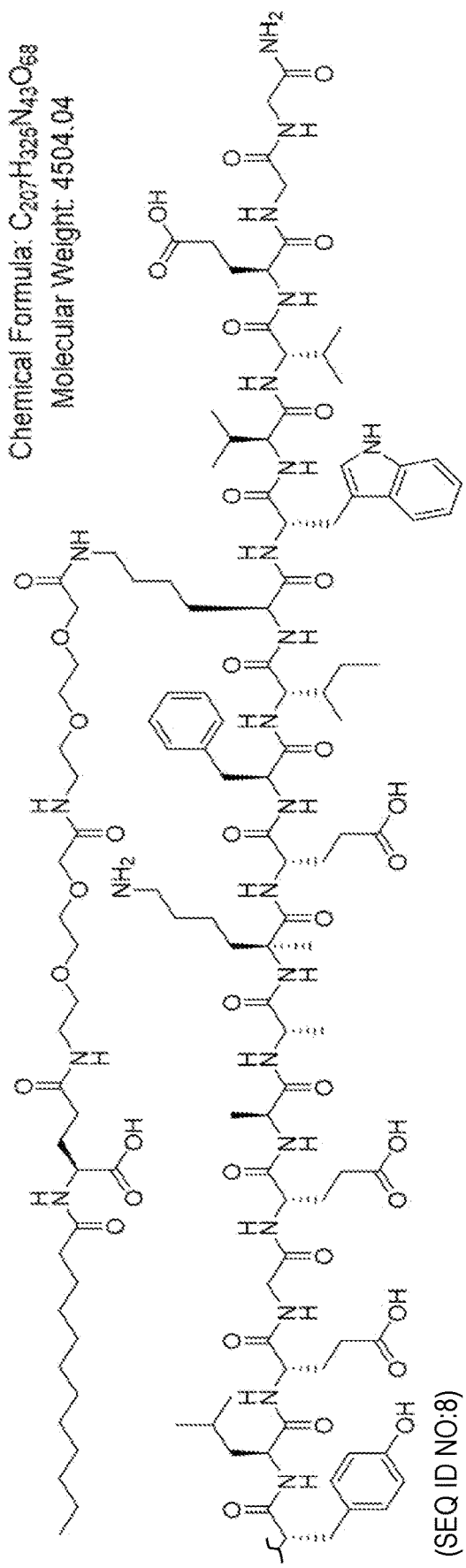
Chemical Formula: $C_{207}H_{325}N_{43}O_{68}$
Molecular Weight: 4504.04
(SEQ ID NO:8)

FIG. 1G
Free-H-[AIB]-EGS-[αMePhe]-TSDV-[αMeSer]-SYK[((PEG2)2-γE-Lauroyl]-EGEAA-[αMeLys]-EFIAK[(PEG2)2-γE-Lauroyl]-VVEGG-amide
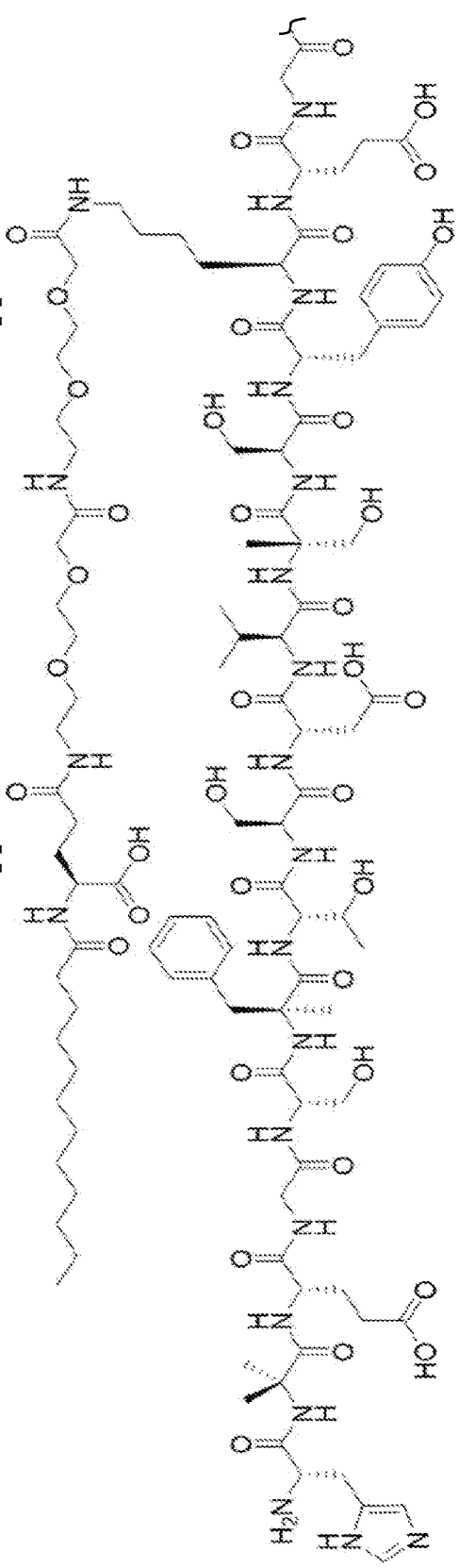
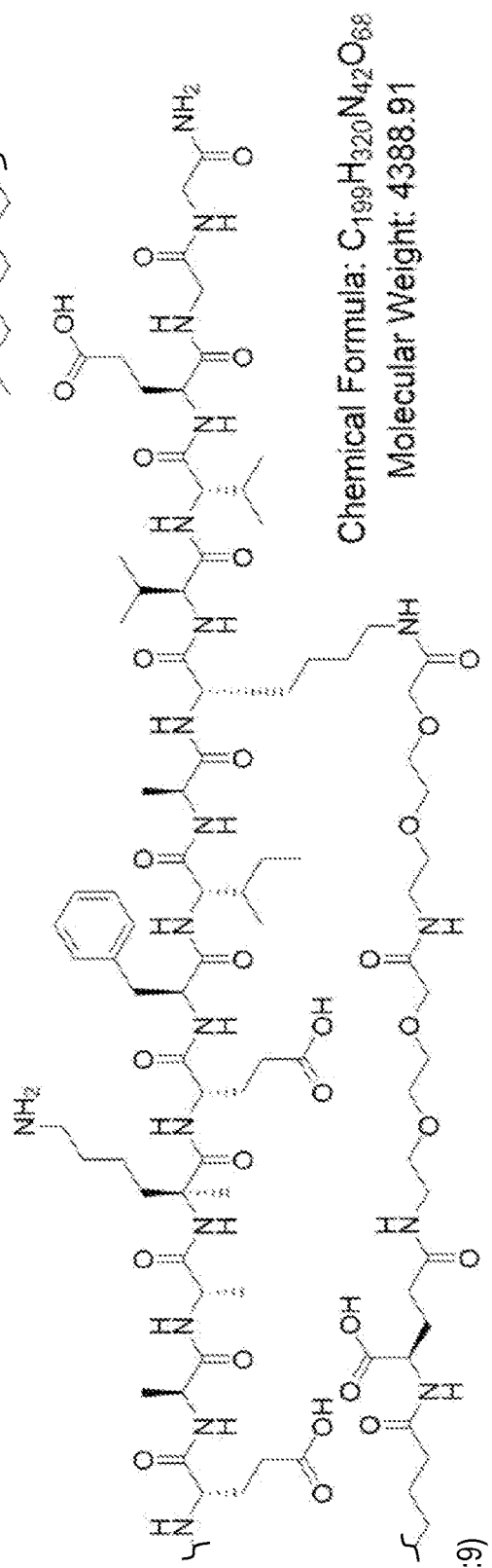
Chemical Formula: $C_{199}H_{320}N_{42}O_{68}$
Molecular Weight: 4388.91
(SEQ ID NO:9)

MEDI7219: Free-H-[AIB]-EGS-[αMePhe]-TSDV-[αMeSer]-SK[(PEG₂)₂-γE-Lauroyl]-LEGEAA-[αMeLys]-E-[αMePhe]-IAK[(PEG₂)₂-γE-Lauroyl]-VVEGG-amide Chemical Formula: C₁₉₇H₃₂₄N₄₂O₆₇
Molecular Weight: 4352.99

(SEQ ID NO:2)

Free-H-[AIB]-EGS-[αMePhe]-TSDV-[αMeSer]-SK[(PEG₂)₂-γE-Palmitoyl]-LEGEAA-[αMeLys]-E-[αMePhe]-IAK[(PEG₂)₂-γE-Palmitoyl]-VVEGG-amide Chemical Formula: C₂₀₅H₃₄₀N₄₂O₆₇
Molecular Weight: 4465.20

(SEQ ID NO:10)

Semaglutide: Free-H-[AIB]-EGTFTSDVSSYLEGQAAK[(PEG2)2-γE-Stearate]-EFIAWLVRGRG-acid Chemical Formula: C187H291N45O59
Molecular Weight: 4113.58

(SEQ ID NO:11)

(SEQ ID NO:12)

(SEQ ID NO:13)

(SEQ ID NO:14)

(SEQ ID NO:15)

ORAL DELIVERY OF GLP-1 PEPTIDE ANALOGS

REFERENCE TO SEQUENCE LISTING SUBMITTED ELECTRONICALLY

The content of the electronically submitted sequence listing in ASCII text file (Name ORPEP-200-PSP_ST25_update.txt; Size: 12,389 bytes; and Date of Creation: Oct. 21, 2018) filed with the application is incorporated herein by reference in its entirety.

BACKGROUND

Field of the Invention

The present disclosure relates to formulations for oral delivery of GLP-1 peptide analogs and methods of administering the same.

Background

Therapeutic peptides are commonly administered by parenteral routes such as intravenous or subcutaneous injection. However, parental administration can result in poor patient compliance due, for example, to needle phobia. Oral administration, in contrast, is a simple and convenient mode of administration. Unfortunately, oral administration of peptides is challenging because the peptides are susceptible to degradation from the acids of the stomach and from proteases. Proteolytic enzymes degrade peptides in the gastrointestinal tract, and this degradation can render the peptides inactive. Oral administration of peptides is also challenging because peptides are poorly absorbed in the gastrointestinal tract. The large size of peptides makes it difficult for them to cross through the intestinal mucus layer and to cross the tight junction epithelial cell layer. These challenges lead to poor bioavailability and high variability in the pharmacokinetic (pK) drug profiles of orally administered peptides.

Glucagon-like peptide 1 (GLP-1) peptide analogs have shown efficacy in treating type 2 diabetes. However, they are currently only available via parenteral administration. Therefore, there is a critical need for orally administering GLP-1 peptides with clinically significant bioavailability that are efficacious and have limited pharmacokinetic variability.

BRIEF SUMMARY OF THE INVENTION

Peptides, such as GLP-1 peptide analogs are generally large amphiphilic molecules that do not go into systemic circulation upon oral administration. In order to achieve systemic exposure, the present invention targets the peptides at their most optimum site of absorption and enhances absorption using formulation components that improve the solubility of the peptide and excipients containing a combination of permeation enhancers sodium chenodeoxycholate and propyl gallate. The present invention also provides a methodology to deliver GLP-1 peptide analogs orally through an approach that involves understanding the site of absorption and improving the solubility of the peptide using excipients, permeation enhancers, and pH modifiers for improved absorption.

In certain embodiments, a pharmaceutical composition for oral administration comprises (i) a bislipidated GLP-1 peptide analog and (ii) sodium chenodeoxycholate.

In certain embodiments, a pharmaceutical composition for oral administration comprises (i) a bislipidated GLP-1 peptide analog and (ii) propyl gallate.

In certain embodiments, a pharmaceutical composition provided herein further comprises sodium chenodeoxycholate. In certain embodiments, the ratio of sodium chenodeoxycholate to propyl gallate is 150:1 to 1:4. In certain embodiments, the ratio of sodium chenodeoxycholate to propyl gallate is 145:1. In certain embodiments, the ratio of sodium chenodeoxycholate to propyl gallate is 29:1. In certain embodiments, the ratio of sodium chenodeoxycholate to propyl gallate is 14:1. In certain embodiments, the ratio of sodium chenodeoxycholate to propyl gallate is 6.5:1. In certain embodiments, the ratio of sodium chenodeoxycholate to propyl gallate is 4:1. In certain embodiments, the ratio of sodium chenodeoxycholate to propyl gallate is 2:1. In certain embodiments, the ratio of sodium chenodeoxycholate to propyl gallate is 1:1. In certain embodiments, the ratio of sodium chenodeoxycholate to propyl gallate is 2:1 to 1:4. In certain embodiments, the ratio of sodium chenodeoxycholate to propyl gallate is 1:2.

In certain embodiments, the amount of sodium chenodeoxycholate is about 1 mg to about 1500 mg. In certain embodiments, the amount of sodium chenodeoxycholate is about 100 mg to about 800 mg. In certain embodiments, the amount of sodium chenodeoxycholate is about 100 mg, about 200 mg, about 300 mg, about 400 mg, about 500 mg, about 600 mg, about 700 mg, or about 800 mg. In certain embodiments, the amount of sodium chenodeoxycholate is about 50 mg, about 65 mg, about 120 mg, about 130 mg, about 140 mg, about 150 mg, about 260 mg, about 280 mg, about 290 mg, or about 299 mg. In certain embodiments, the amount of sodium chenodeoxycholate is about 100 mg. In certain embodiments, sodium chenodeoxycholate is about 15% to about 25% of the pharmaceutical composition by weight. In certain embodiments, sodium chenodeoxycholate is about 20% to about 21% of the pharmaceutical composition by weight. In certain embodiments, sodium chenodeoxycholate is about 15% to about 65% of the pharmaceutical composition by weight. In certain embodiments, sodium chenodeoxycholate is about 30% to about 65% of the pharmaceutical composition by weight.

In certain embodiments, the amount of propyl gallate is about 1 mg to about 3000 mg. In certain embodiments, the amount of propyl gallate is about 200 mg to about 1600 mg. In certain embodiments, the amount of propyl gallate is about 2 mg, about 10 mg, about 20 mg, about 30 mg, about 40 mg, about 50 mg, about 100 mg, about 150 mg, or about 200 mg. In certain embodiments, the amount of propyl gallate is about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, or about 1600 mg. In certain embodiments, the amount of propyl gallate is about 200 mg. In certain embodiments, propyl gallate is about 45% to about 55% of the pharmaceutical composition by weight. In certain embodiments, propyl gallate is about 40% to about 41% of the pharmaceutical composition by weight.

In certain embodiments, the pharmaceutical composition does not comprise propyl gallate. In certain embodiments, a pharmaceutical composition provided herein further comprises a pH modifier.

In certain embodiments, a pharmaceutical composition provided herein further comprises Tris base. In certain embodiments, the amount of Tris base is up to 300 mg. In certain embodiments, the amount of Tris base is about 30 mg to about 40 mg. In certain embodiments, the amount of Tris base is about 36 mg to about 37 mg. In certain embodiments, Tris base is about 5% to about 10% of the pharmaceutical composition by weight. In certain embodiments, Tris base is about 7% to about 8% of the pharmaceutical composition by weight.

In certain embodiments, a pharmaceutical composition provided herein does not comprise a pH modifier.

In certain embodiments, a pharmaceutical composition provided herein does not comprise Tris base.

In certain embodiments, a pharmaceutical composition provided herein comprises an enteric coating, e.g., an enteric coating that dissolves at a pH of about 5 to about 7.5, an enteric coating that dissolves at a pH of about 5.5 or above, or an enteric coating that dissolves at a pH of about 7.0 or above.

In certain embodiments, a pharmaceutical composition provided herein further comprises a bioadhesive.

In certain embodiments, a pharmaceutical composition provided herein further comprises cross-linked polyacrylic polymers. In certain embodiments, the cross-linked polyacrylic polymers are in a powder form or a granular from.

In certain embodiments, a pharmaceutical composition provided herein further comprises Carbopol®.

In certain embodiments, the amount of bioadhesive or cross-linked polyacrylic polymers or Carbopol® is about 1 mg to about 50 mg. In certain embodiments, the amount of bioadhesive or cross-linked polyacrylic polymers or Carbopol® is about 1 mg to about 2 mg. In certain embodiments, the amount of bioadhesive or cross-linked polyacrylic polymers or Carbopol® is about 4 mg to about 5 mg. In certain embodiments, the amount of bioadhesive or cross-linked polyacrylic polymers or Carbopol® is about 14 mg to about 15 mg. In certain embodiments, the amount of bioadhesive or cross-linked polyacrylic polymers or Carbopol® is about 48 mg to about 49 mg. In certain embodiments, the bioadhesive or cross-linked polyacrylic polymers or Carbopol® is about 0.3% to about 10% of the pharmaceutical composition by weight. In certain embodiments, the bioadhesive or cross-linked polyacrylic polymers or Carbopol® is about 0.3% to about 3% of the pharmaceutical composition by weight. In certain embodiments, the bioadhesive or cross-linked polyacrylic polymers or Carbopol® is about 1% to about 10% of the pharmaceutical composition by weight. In certain embodiments, the bioadhesive or cross-linked polyacrylic polymers or Carbopol® is about 0.3%, about 1%, about 3%, or about 10% of the pharmaceutical composition by weight. In certain embodiments, the bioadhesive or cross-linked polyacrylic polymers or Carbopol® is about 0.3%, about 0.9%, or about 1.2% of the pharmaceutical composition by weight.

In certain embodiments, the Carbopol® is Carbopol® 71G. In certain embodiments, the amount of Carbopol® 71G is about 4 mg to about 5 mg. In certain embodiments, the amount of Carbopol® 71G is about 48 mg to about 49 mg. In certain embodiments, Carbopol® 71G is about 1% to about 10% of the pharmaceutical composition by weight.

In certain embodiments, the Carbopol® is Carbopol® 971P. In certain embodiments, the amount of Carbopol® 971P is about 1 mg to about 2 mg. In certain embodiments, the amount of Carbopol® 971P is about 14 mg to about 15 mg. In certain embodiments, Carbopol® 971P is about 0.3% to about 3% of the pharmaceutical composition by weight.

In certain embodiments, a pharmaceutical composition provided herein does not comprise a bioadhesive.

In certain embodiments, a pharmaceutical composition provided herein does not comprise cross-linked polyacrylic polymers.

In certain embodiments, a pharmaceutical composition provided herein further comprises an enteric coat. In certain embodiments, a pharmaceutical composition provided herein further comprises methacrylic acid copolymers. In certain embodiments, a pharmaceutical composition provided herein further comprises Eudragit®. In certain embodiments, the amount of enteric coat or methacrylic acid copolymers or Eudragit® is about 10 mg to about 65 mg. In certain embodiments, the amount of enteric coat or methacrylic acid copolymers or Eudragit® is about 61 mg to about 62 mg. In certain embodiments, the amount of enteric coat or methacrylic acid copolymers or Eudragit® is about 10 mg to about 53 mg. In certain embodiments, the enteric coat or methacrylic acid copolymers or Eudragit® is about 5% to about 15% of the pharmaceutical composition by weight.

In certain embodiments, the enteric coat or methacrylic acid copolymers or Eudragit® dissolves at pH 5.5 or above.

In certain embodiments, a pharmaceutical composition provided herein further comprises a filler. In certain embodiments, a pharmaceutical composition provided herein further comprises a diluent. In certain embodiments, a pharmaceutical composition provided herein further comprises mannitol. In certain embodiments, the amount of the filler, diluent, or mannitol is about 1 mg to about 150 mg. In certain embodiments, the amount of the filler, diluent, or mannitol is about 50 mg to about 100 mg. In certain embodiments, the amount of the filler, diluent, or mannitol is about 75 mg to about 150 mg. In certain embodiments, the filler, diluent, or mannitol is about 5% to about 30% of the pharmaceutical composition by weight. In certain embodiments, the filler, diluent, or mannitol is about 5% to about 20% of the pharmaceutical composition by weight. In certain embodiments, the filler, diluent, or mannitol is about 10% to about 20% of the pharmaceutical composition by weight. In certain embodiments, the filler, diluent, or mannitol is about 15% to about 30% of the pharmaceutical composition by weight.

In certain embodiments, a pharmaceutical composition provided herein further comprises a disintegrant. In certain embodiments, a pharmaceutical composition provided herein further comprises crospovidone. In certain embodiments, the amount of disintegrant or crospovidone is about 25 mg to about 35 mg. In certain embodiments, the amount of disintegrant or crospovidone is about 28 mg to about 29 mg. In certain embodiments, the disintegrant or crospovidone is about 1% to about 10% of the pharmaceutical composition by weight. In certain embodiments, the disintegrant or crospovidone is about 5% to about 6% of the pharmaceutical composition by weight.

In certain embodiments, a pharmaceutical composition provided herein further comprises a glidant. In certain embodiments, a pharmaceutical composition provided herein further comprises fumed silica. In certain embodiments, the amount of glidant or fumed silica is about 1 mg to about 10 mg. In certain embodiments, the amount of glidant or fumed silica is about 4 mg to about 5 mg. In certain embodiments, the glidant or fumed silica is about 1% of the pharmaceutical composition by weight.

In certain embodiments, a pharmaceutical composition provided herein further comprises a lubricant. In certain embodiments, a pharmaceutical composition provided herein further comprises sodium stearyl fumarate. In certain embodiments, the amount of lubricant or sodium stearyl fumarate is about 20 mg to about 30 mg. In certain embodiments, the amount of lubricant or sodium stearyl fumarate is about 24 mg to about 25 mg. In certain embodiments, the lubricant or sodium stearyl fumarate is about 5% of the pharmaceutical composition by weight.

In certain embodiments, a pharmaceutical composition provided herein further comprises sodium caprate. In certain embodiments, the composition comprises about 300 mg to about 2400 mg sodium caprate. In certain embodiments, the composition comprises about 300 mg sodium caprate. In certain embodiments, the composition comprises about 600 mg sodium caprate. In certain embodiments, the composition comprises about 900 mg sodium caprate. In certain embodiments, the composition comprises about 1200 mg sodium caprate. In certain embodiments, the composition comprises about 2400 mg sodium caprate.

In certain embodiments, a pharmaceutical composition for oral administration comprises a bislipidated GLP-1 peptide analog and sodium N-(8-(2-hydroxybenzoyl)amino) caprylate (SNAC).

In certain embodiments, a pharmaceutical composition for oral administration comprises a bislipidated GLP-1 peptide analog and sodium caprate.

In certain embodiments of a pharmaceutical composition provided herein the amount of the GLP-1 peptide analog is about 0.1 mg to about 100 mg. In certain embodiments of a pharmaceutical composition provided herein the amount of the GLP-1 peptide analog is about 0.0625 mg to about 36 mg. In certain embodiments of a pharmaceutical composition provided herein, the amount of the GLP-1 peptide analog is about 0.25 mg to about 36 mg. In certain embodiments of a pharmaceutical composition provided herein the amount of the GLP-1 peptide analog is about 0.125 mg, about 4.5 mg, or about 36 mg. In certain embodiments of a pharmaceutical composition provided herein the GLP-1 peptide analog is about 0.2% to about 10% of the pharmaceutical composition by weight.

In certain embodiments, a pharmaceutical composition for oral administration comprises (i) about 0.1 mg to about 100 mg of a bislipidated GLP-1 peptide analog (ii) about 1 mg to about 1500 mg sodium chenodeoxycholate, (iii) about 1 mg to about 3000 mg propyl gallate, and (iv) 0 to about 300 mg Tris base. In certain embodiments, the pharmaceutical composition further comprises a filler, disintegrant, glidant, lubricant, bioadhesive and/or enteric coat. In certain embodiments, the pharmaceutical composition further comprises mannitol, crospovidone, fumed silica, sodium stearyl fumarate, cross-linked polyacrylic acid polymers, and/or methacrylic acid copolymers.

In certain embodiments, a pharmaceutical composition for oral administration comprises i) about 0.1% to about 10% of a bislipidated GLP-1 peptide analog (ii) about 10% to about 30% sodium chenodeoxycholate, and (iii) about 20% to about 60% propyl gallate.

In certain embodiments, a pharmaceutical composition for oral administration comprises (i) about 0.1% to about 10% of a bislipidated GLP-1 peptide analog (ii) about 15% to about 25% sodium chenodeoxycholate, and (iii) about 30% to about 50% propyl gallate.

In certain embodiments, the pharmaceutical composition further comprises (iv) about 5% to about 20% mannitol, (v) 0 to about 10% Tris base; (vi) about 2% to about 10% crospovidone, (vii) about 0.5% to about 5% fumed silica, and/or (viii) about 1% to about 15% sodium stearyl fumarate. In certain embodiments, the pharmaceutical composition comprises about 3% to about 10% crospovidone. In certain embodiments, the pharmaceutical composition comprises about 1% to about 5% fumed silica.

In certain embodiments, a pharmaceutical composition for oral administration comprises (i) about 0.256% to about 7.364% of a bislipidated GLP-1 peptide analog (ii) about 20.5% sodium chenodeoxycholate, (iii) about 40.9% propyl gallate, (iv) about 6.833% to about 18.903% mannitol, (v) 0 to about 7.815% Tris base; (vi) about 5.81% crospovidone, (vii) about 1% fumed silica, and (viii) about 2% to about 10% sodium stearyl fumarate.

In certain embodiments, a pharmaceutical composition for oral administration comprises (i) about 0.256% to about 7.364% of a bislipidated GLP-1 peptide analog (ii) about 20.5% sodium chenodeoxycholate, (iii) about 40.9% propyl gallate, (iv) about 6.833% to about 18.903% mannitol, (v) 0 to about 7.815% Tris base; (vi) about 5.81% crospovidone, (vii) about 0.3% to about 10% cross-linked polyacrylic acid polymers, (viii) about 1% fumed silica, and (ix) about 2% to about 10% sodium stearyl fumarate.

In certain embodiments, a pharmaceutical composition for oral administration comprises (i) about 0.1 mg to about 40 mg of a bislipidated GLP-1 peptide analog; (ii) about 75 mg to about 125 mg of sodium chenodeoxycholate, and (iii) about 150 mg to about 250 mg propyl gallate.

In certain embodiments, the pharmaceutical composition further comprises (iv) about 40 mg to about 125 mg mannitol, (v) 0 to about 45 mg Tris base, (vi) about 25 mg to about 35 mg crospovidone, (vii) about 1 mg to about 10 mg fumed silica, and (viii) about 20 mg to about 30 mg sodium stearyl fumarate.

In certain embodiments, a pharmaceutical composition for oral administration comprises (i) about 1.25 mg, about 4.5 mg, or about 36 mg of a bislipidated GLP-1 peptide analog; (ii) about 100 mg of sodium chenodeoxycholate, (iii) about 200 mg propyl gallate, (iv) about 94.7 mg, about 89.6 mg, or about 51.8 mg mannitol, (v) 0 to about 36.2 mg Tris base, (vi) about 28.4 mg crospovidone, (vii) about 4.9 mg fumed silica, and (viii) about 24.4 mg sodium stearyl fumarate.

In certain embodiments, a pharmaceutical composition for oral administration comprises (i) about 1 mg to about 10 mg of a bislipidated GLP-1 peptide analog; (ii) about 50 mg to about 150 mg of sodium chenodeoxycholate, and (iii) about 100 mg to about 300 mg propyl gallate. In certain embodiments, the pharmaceutical composition further comprises (iv) about 50 mg to about 150 mg mannitol, (v) 0 to about 50 mg Tris base (vi) about 10 mg to about 45 mg crospovidone, (vii) about 1 mg to about 10 mg fumed silica, and (viii) about 5 mg to about 25 mg sodium stearyl fumarate.

In certain embodiments, a pharmaceutical composition for oral administration comprises (i) about 4.5 mg of a bislipidated GLP-1 peptide analog; (ii) about 100 mg of sodium chenodeoxycholate, (iii) about 200 mg propyl gallate, (iv) about 101.8 mg to about 138 mg, about 88.1 mg to about 124.3 mg, or about 75 mg or 11.2 mg mannitol, (v) 0 to about 36.2 mg Tris base, (vi) 0 mg, about 1.5 mg, or about 14.6 mg cross-linked polyacrylic acid polymers, (vii) about 28.4 mg crospovidone, (viii) about 4.9 mg fumed silica, and (ix) about 12.2 mg or 24.4 mg sodium stearyl fumarate.

In certain embodiments, a pharmaceutical composition for oral administration comprises (i) about 1 to about 15 mg of a bislipidated GLP-1 peptide analog; (ii) about 100 mg to about 800 mg of sodium chenodeoxycholate, and (iii) about 200 mg to about 1600 mg propyl gallate. In certain embodiments, the pharmaceutical composition comprises about 300 mg to about 400 mg of sodium chenodeoxycholate and about 600 mg to about 800 mg propyl gallate. In certain embodiments, the pharmaceutical composition further comprises mannitol, Tris, fumed silica, and/or sodium stearyl fumarate. In certain embodiments, the pharmaceutical composition further comprises about 50 mg to about 150 mg mannitol, 0 to about 50 mg Tris base about 10 mg to about 45 mg crospovidone, about 1 mg to about 10 mg fumed silica, and/or about 5 mg to about 25 mg sodium stearyl fumarate. In certain embodiments, the pharmaceutical composition further comprises cross-linked polyacrylic acid polymers.

In certain embodiments, a pharmaceutical composition provided herein comprises an enteric coat. In certain embodiments, the enteric coat comprises methacrylic acid copolymers.

In certain embodiments, a pharmaceutical composition provided herein comprises a ratio of sodium chenodeoxycholate to propyl gallate of about 1:2.

In certain embodiments, a pharmaceutical composition provided herein comprises Tris base. In certain embodiments, a pharmaceutical composition provided herein does not comprise Tris base.

In certain embodiments, a pharmaceutical composition provided herein comprises a GLP-1 peptide analog that comprises any one of SEQ ID NOs: 2-10 or 12-15 or a salt thereof (e.g., an ammonium acetate salt). In certain embodiments, the GLP-1 peptide analog comprises SEQ ID NO:2 or a salt thereof (e.g., an ammonium acetate salt). In certain embodiments, the GLP-1 peptide comprises SEQ ID NO:2 and an ammonium acetate salt thereof. In certain embodiments, the GLP-1 peptide comprises an ammonium acetate salt of SEQ ID NO:2.

In certain embodiments, a pharmaceutical composition provided herein is a solid dosage form.

In certain embodiments, a pharmaceutical composition provided herein is in the form of a tablet, a hard capsule, or a soft capsule.

In certain embodiments, a pharmaceutical composition provided herein is an immediate release, enterically coated, sustained release, or delayed release composition.

In certain embodiments of a pharmaceutical composition provided herein the GLP-1 peptide analog is absorbed in the proximal colon. In certain embodiments of a pharmaceutical composition provided herein the GLP-1 peptide analog is absorbed in the proximal small bowel region. In certain embodiments of a pharmaceutical composition provided herein the GLP-1 peptide analog is absorbed in the proximal colon and the proximal small bowel region.

In certain embodiments of a pharmaceutical composition provided herein, administration of the pharmaceutical composition to a human results in a bioavailability of about 0.5% to about 35%.

In certain embodiments of a pharmaceutical composition provided herein, administration of the pharmaceutical composition results in a pK variability that does not exceed 100% or above, 50% or above, 25% or above and that is decreasing upon repeated daily dosing.

In certain embodiments, a pharmaceutical composition provided herein has a disintegration time of about 5 minutes to about 100 minutes in disintegration test assay.

In certain embodiments, a pharmaceutical composition provided herein has a dissolution time of about 10 minutes to about 500 minutes in dissolution test assay.

In certain embodiments, a pharmaceutical composition provided herein is less than 2 grams, less than 1.5 grams, less than 1.0 grams, or less than 0.5 grams. In certain embodiments, a pharmaceutical composition is about 400 mg to about 500 mg.

In certain embodiments, a method of improving glycemic control comprises administering a pharmaceutical composition provided herein to a subject in need thereof.

In certain embodiments, a method of treating or preventing a disease or condition caused or characterized by hyperglycemia or impaired insulin release comprises administering a pharmaceutical composition provided herein to a subject in need thereof.

In certain embodiments, a method of treating or preventing diabetes comprises administering a pharmaceutical composition provided herein to a subject in need thereof. In certain embodiments, the diabetes is type-2 diabetes.

In certain embodiments, a method of reducing body weight comprises administering a pharmaceutical composition provided herein to a subject in need thereof.

In certain embodiments, a method of reducing body fat comprises administering a pharmaceutical composition provided herein to a subject in need thereof.

In certain embodiments, a method of treating obesity comprises administering a pharmaceutical composition provided herein to a subject in need thereof.

In certain embodiments, a method of treating or preventing a disease or condition caused or characterized by excess body weight comprises administering a pharmaceutical composition provided herein to a subject in need thereof.

In certain embodiments, a method of managing weight comprises administering a pharmaceutical composition provided herein to a subject in need thereof.

In certain embodiments, a method of increasing lipid oxidation comprises administering a pharmaceutical composition provided herein to a subject in need thereof.

In certain embodiments of the methods provided herein, the subject has diabetes. In certain embodiments, the diabetes is type 2 diabetes mellitus.

In certain embodiments of the methods provided herein, the subject's appetite is reduced.

In certain embodiments of the methods provided herein, the pharmaceutical composition is administered once per day.

In certain embodiments of the methods provided herein, the subject is human.

In certain embodiments, a method of making a pharmaceutical composition provided herein comprises combining the GLP-1 peptide analog, the sodium chenodeoxycholate, and the propyl gallate into an oral pharmaceutical composition.

BRIEF DESCRIPTION OF THE DRAWINGS

FIG. 1A shows the chemical structure, chemical formula, and molecular weight for SEQ ID NO:3.

FIG. 1B shows the chemical structure, chemical formula, and molecular weight for SEQ ID NO:4.

FIG. 1C shows the chemical structure, chemical formula, and molecular weight for SEQ ID NO:5.

FIG. 1F shows the chemical structure, chemical formula, and molecular weight for SEQ ID NO:8.

FIG. 1G shows the chemical structure, chemical formula, and molecular weight for SEQ ID NO:9.

DETAILED DESCRIPTION OF THE INVENTION

Figure 1D:
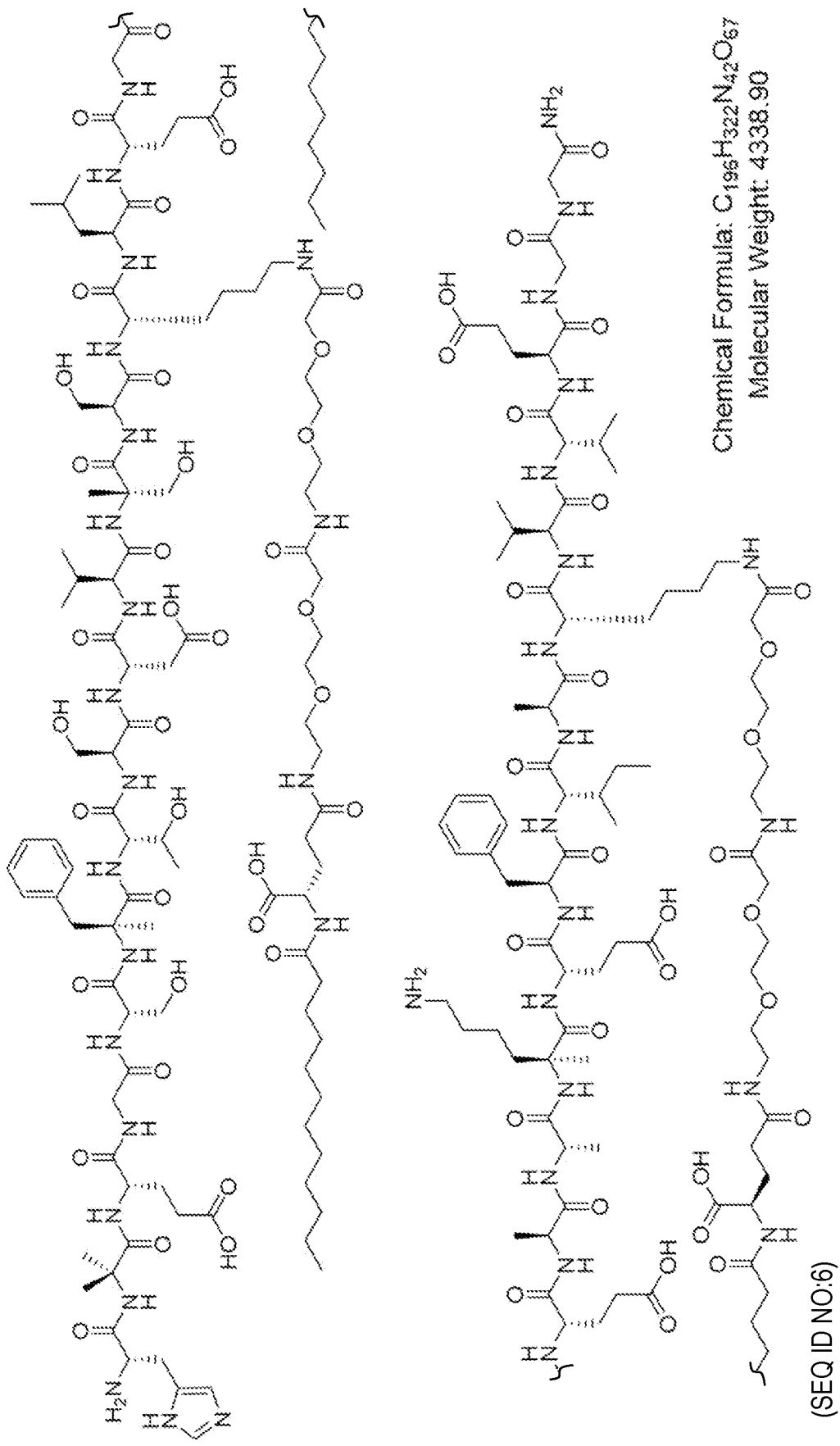
FIG. 1D shows the chemical structure, chemical formula, and molecular weight for SEQ ID NO:6.
Figure 1E:
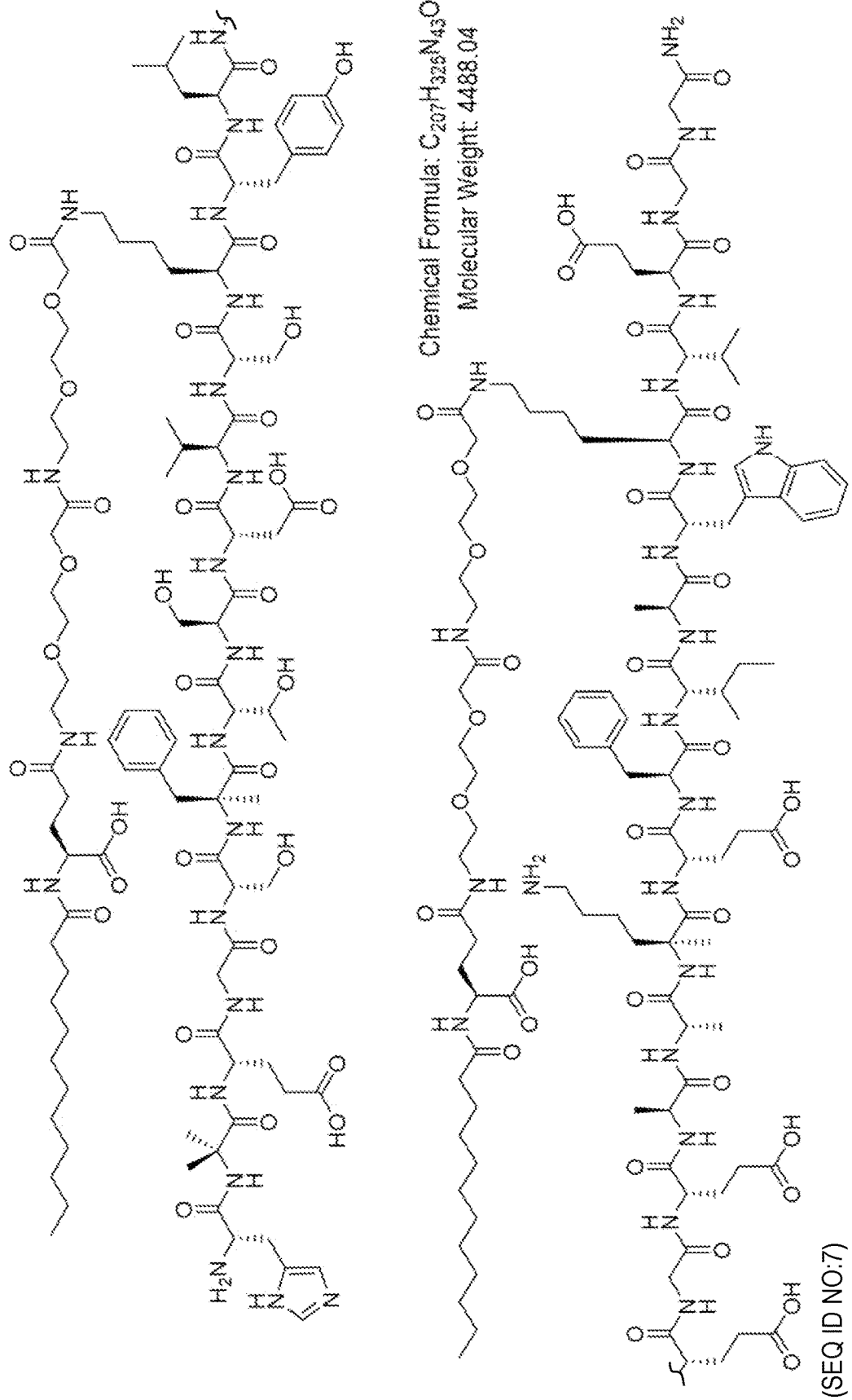
FIG. 1E shows the chemical structure, chemical formula, and molecular weight for SEQ ID NO:7.
Figure 1H:
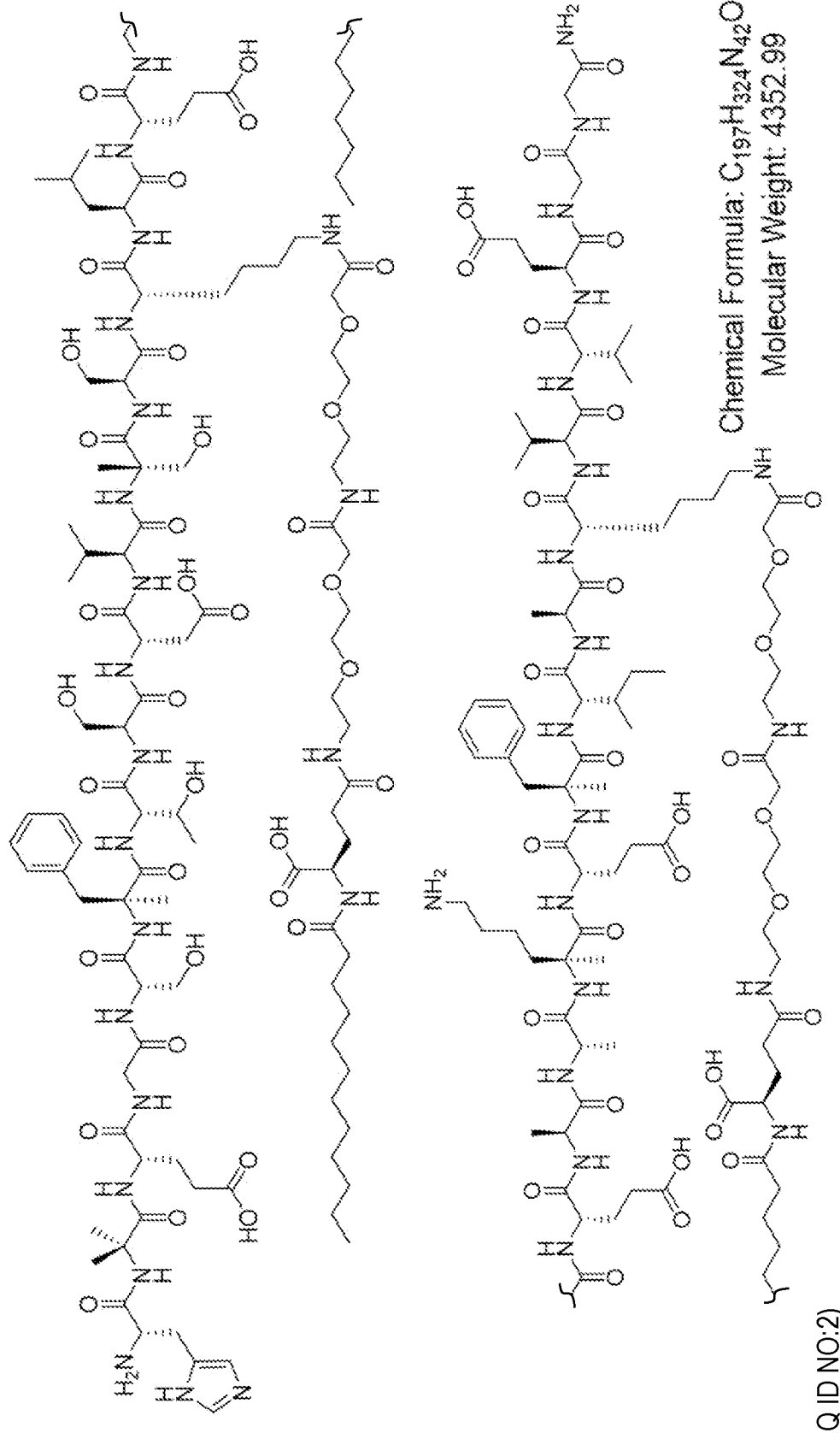
FIG. 1H shows the chemical structure, chemical formula, and molecular weight for SEQ ID NO:2 (MEDI7219).
Figure 1I:
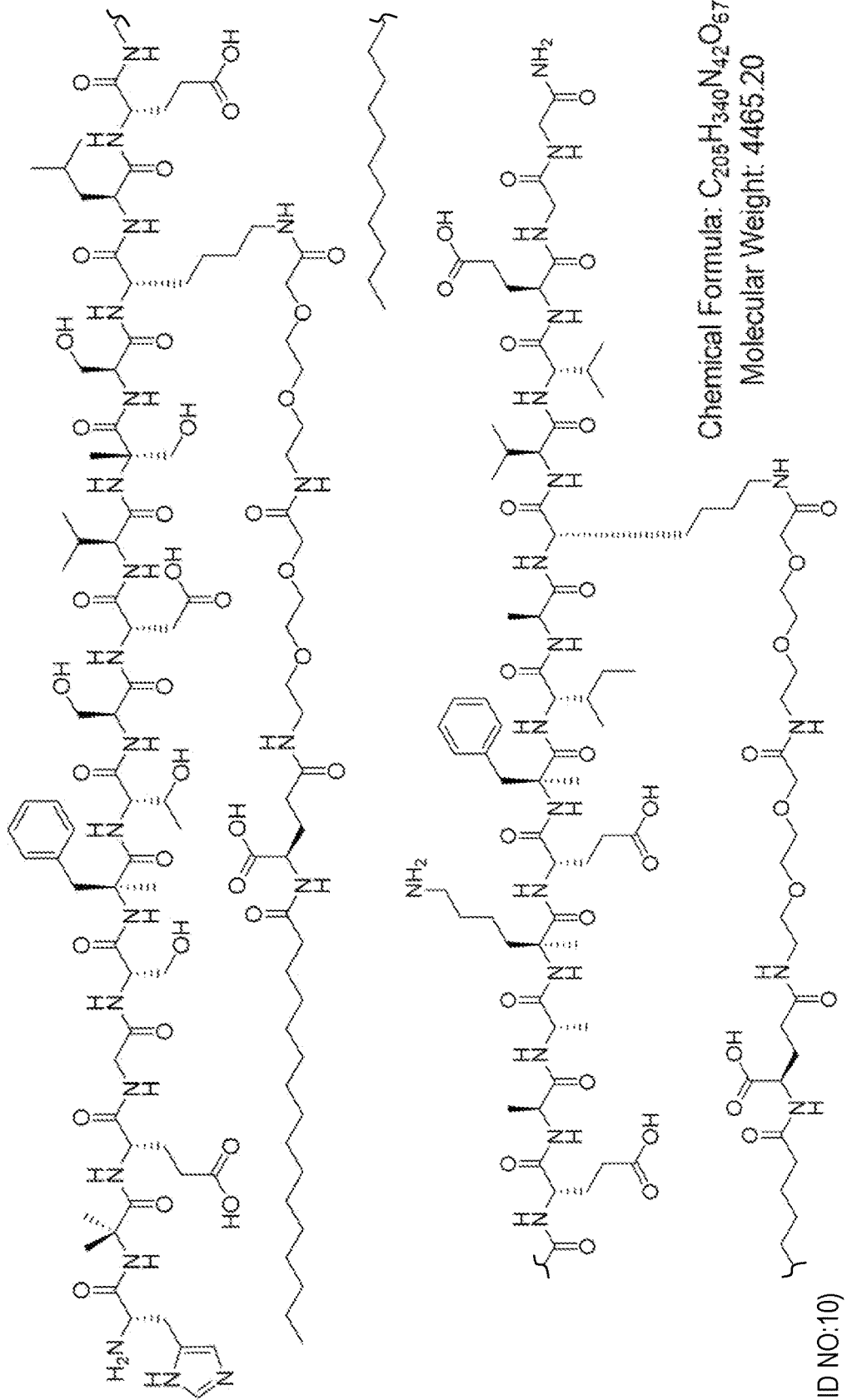
FIG. 1I shows the chemical structure, chemical formula, and molecular weight for SEQ ID NO:10.
Figure 1J:
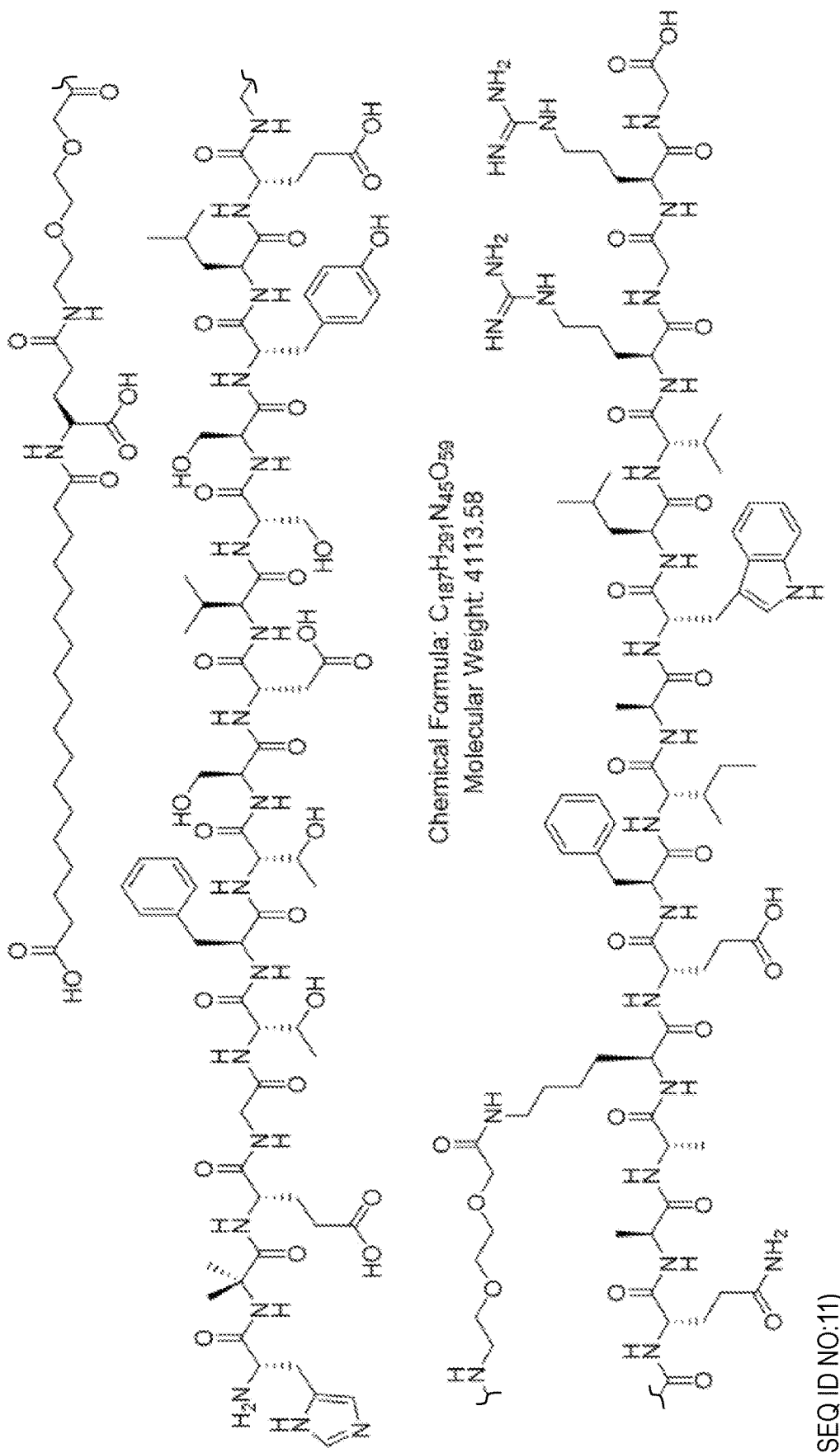
FIG. 1J shows the chemical structure, chemical formula, and molecular weight for semaglutide (SEQ ID NO:11).
Figure 1K:
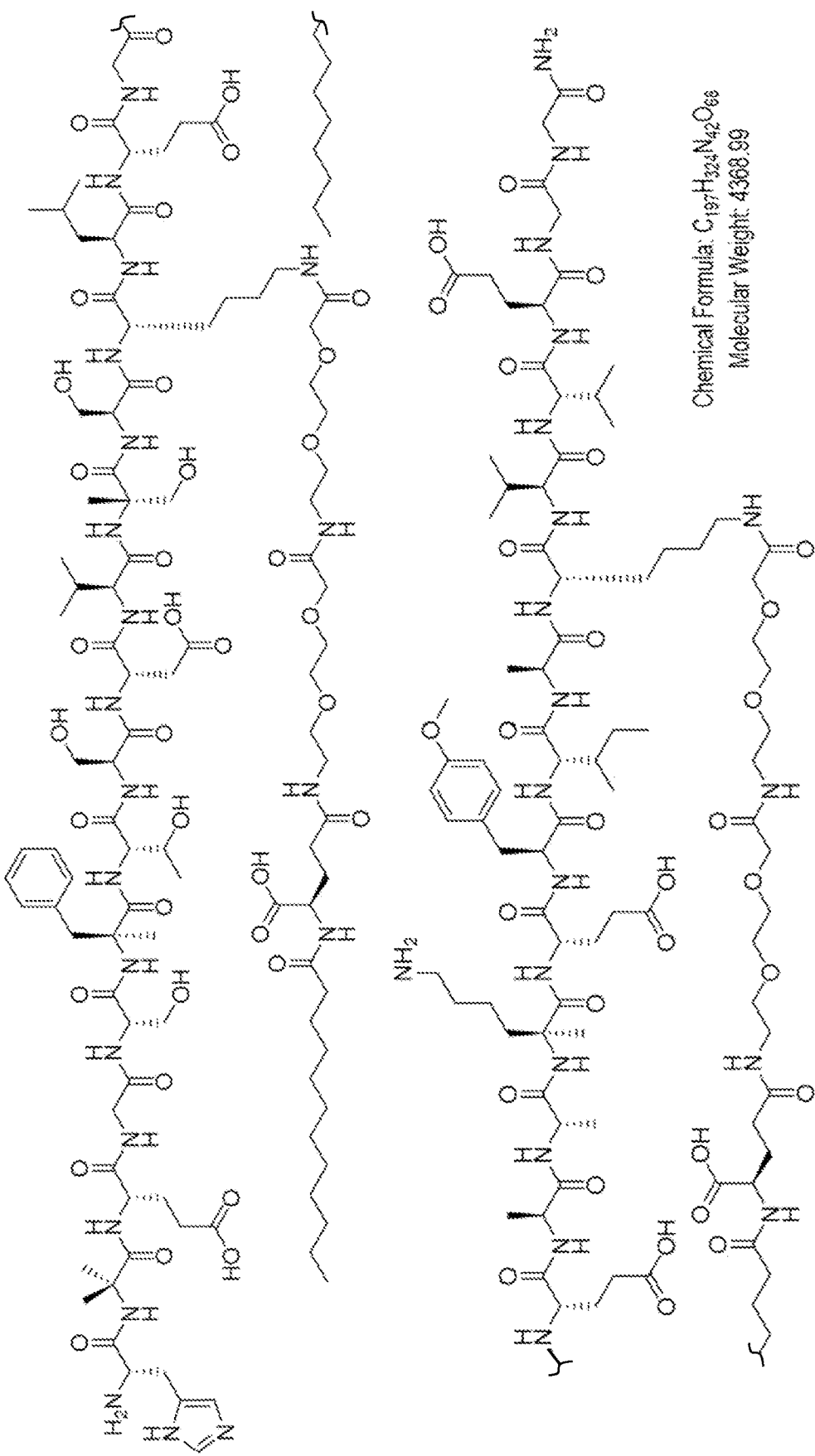
FIG. 1K shows the chemical structure, chemical formula, and molecular weight for SEQ ID NO:12.
Figure 1L:
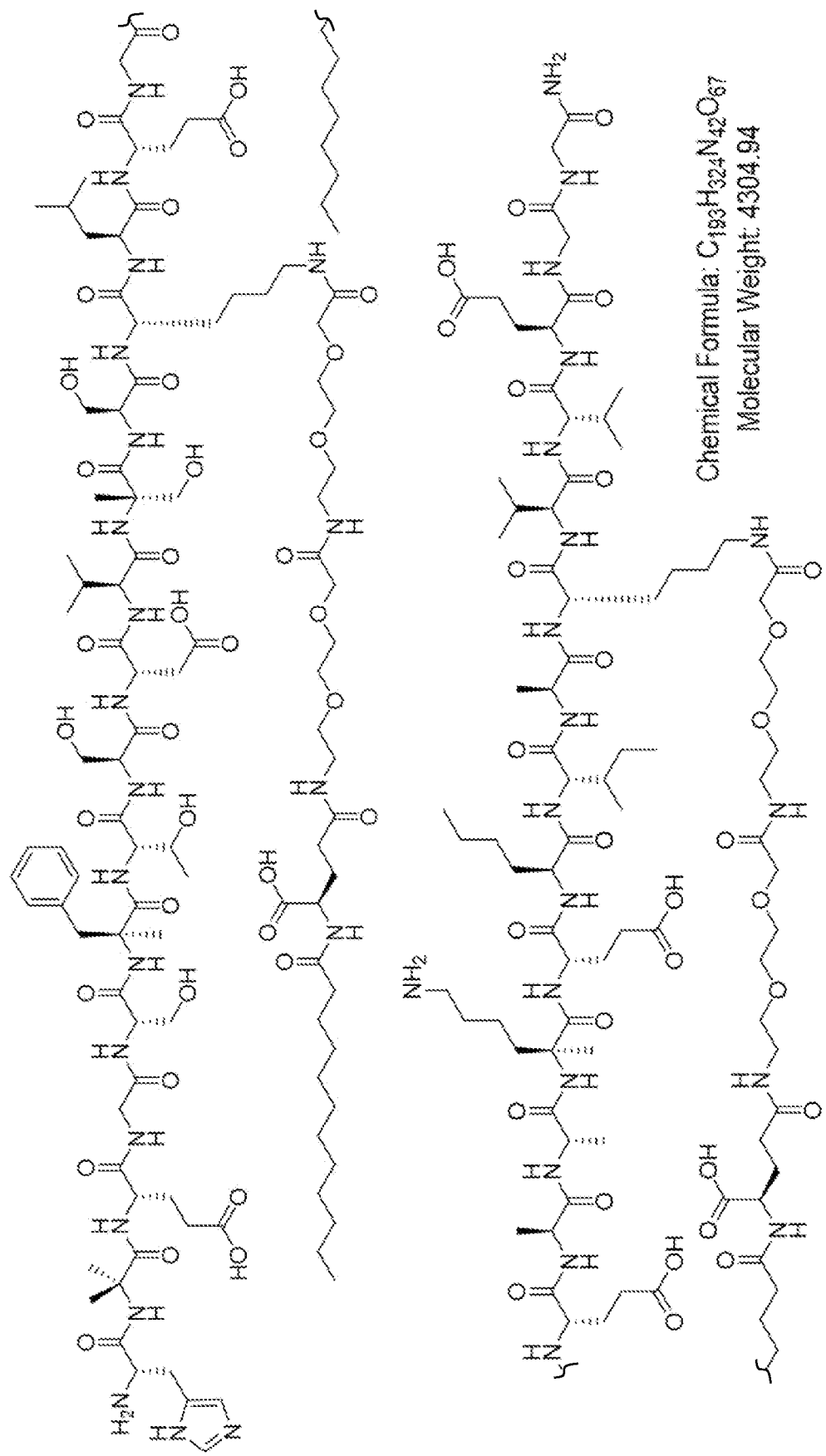
FIG. 1L shows the chemical structure, chemical formula, and molecular weight for SEQ ID NO:13.
Figure 1M:
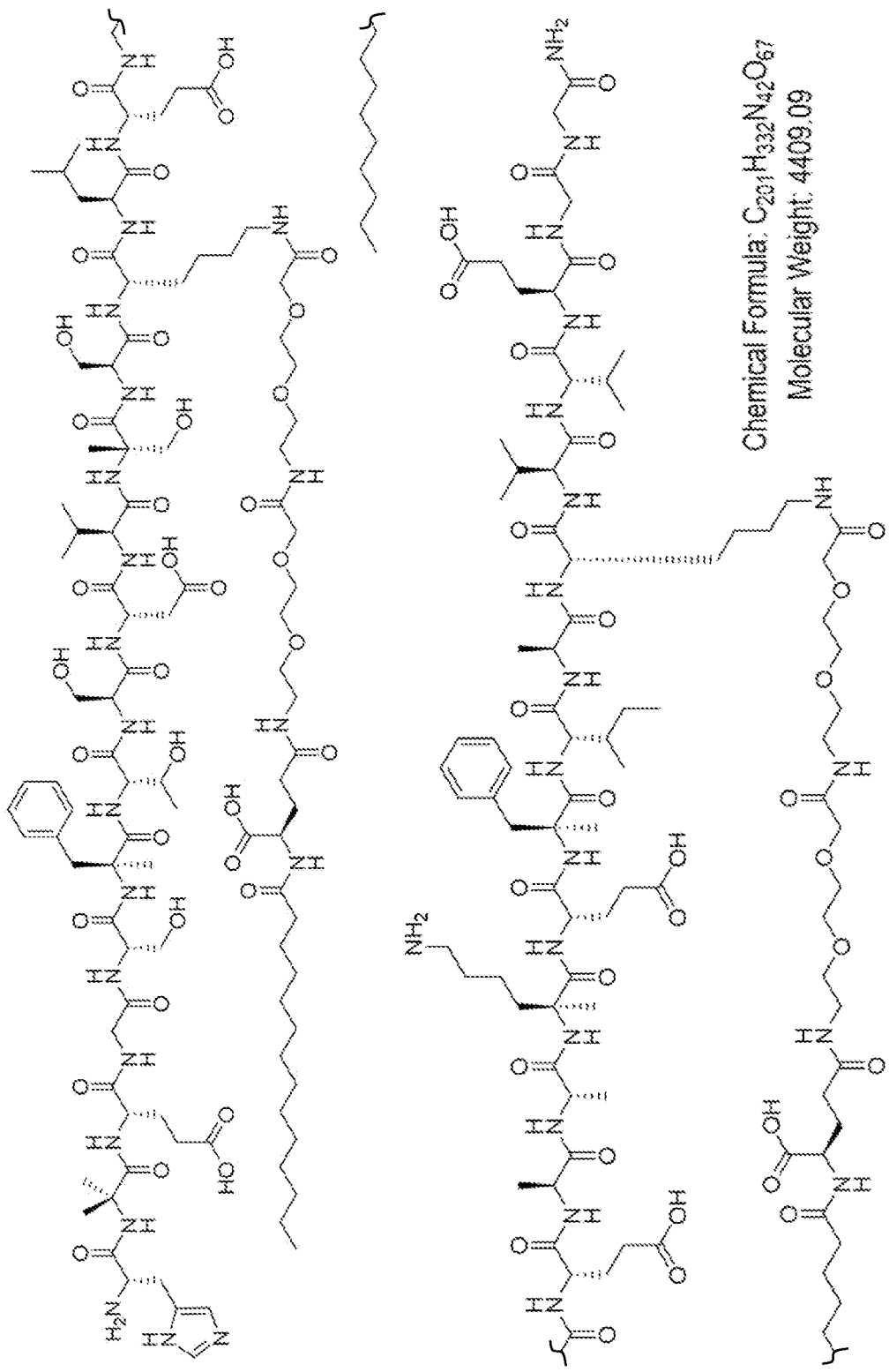
FIG. 1M shows the chemical structure, chemical formula, and molecular weight for SEQ ID NO:14.
Figure 1N:
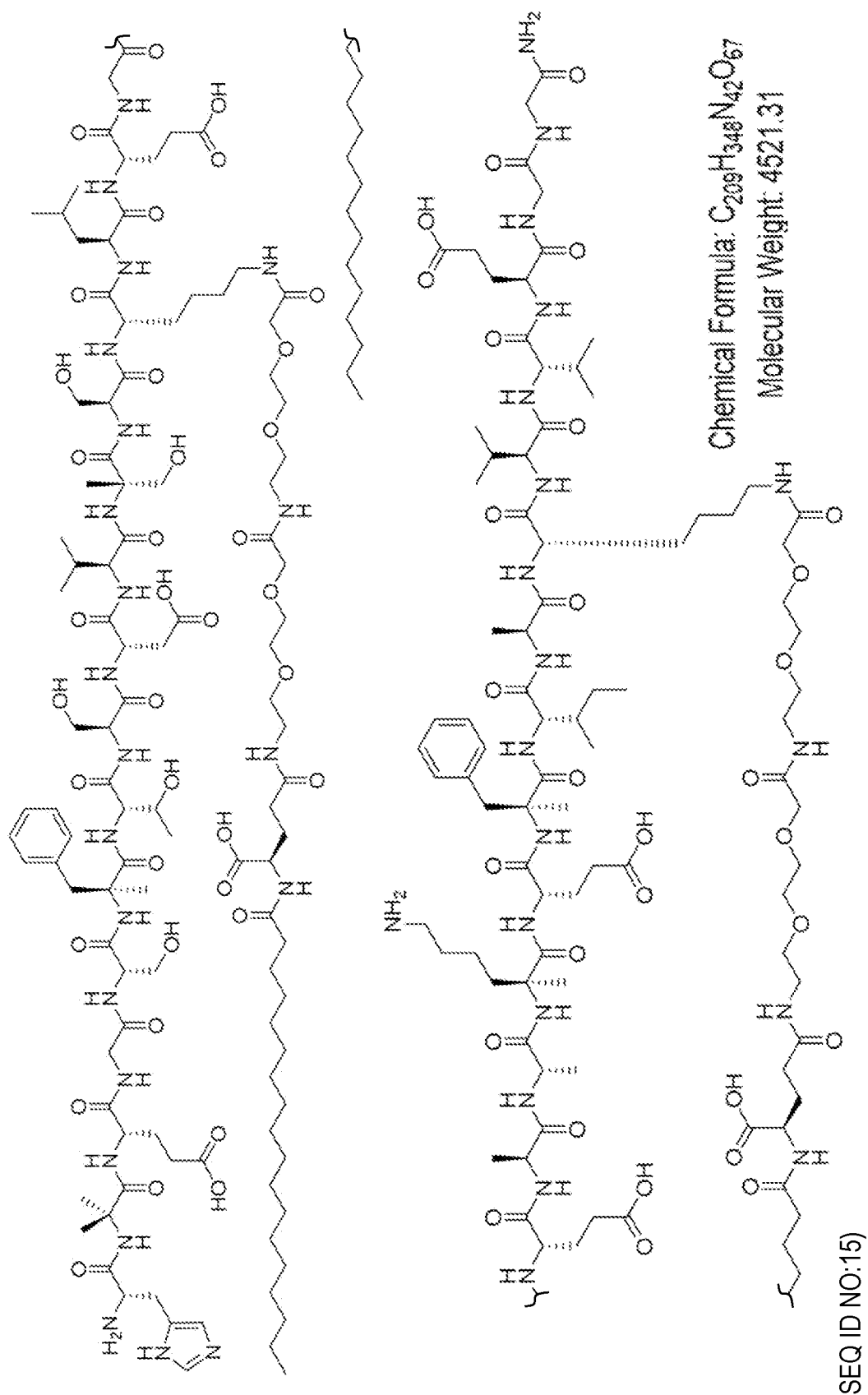
FIG. 1N shows the chemical structure, chemical formula, and molecular weight for SEQ ID NO:15.

It should be appreciated that the particular implementations shown and described herein are examples and are not intended to otherwise limit the scope of the application in any way.

The published patents, patent applications, websites, company names, and scientific literature referred to herein are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

I. Definitions

As used in this specification, the singular forms "a," "an" and "the" specifically also encompass the plural forms of the terms to which they refer, unless the content clearly dictates otherwise. As such, the terms "a" (or "an"), "one or more," and "at least one" can be used interchangeably herein.

The term "about" is used herein to mean approximately, in the region of, roughly, or around. When the term "about" is used in conjunction with a numerical range, it modifies that range by extending the boundaries above and below the numerical values set forth. In general, unless otherwise stated, the term "about" is used herein to modify a numerical value above and below the stated value by a variance of 20%.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided. A peptide "comprising" a particular amino acid sequence refers to a peptide containing the amino acid sequence, wherein the peptide may or may not contain additional amino acids or other modifications to the amino acid sequence. A peptide "consisting of" a particular amino acid sequence refers to a peptide containing only the amino acid sequence and no additional amino acids or other modifications to the amino acid sequence. A peptide "comprising" an amino acid sequence "consisting of" a particular amino acid sequence refers to a peptide containing the amino acid sequence and no additional amino acids; however, the peptide may comprise other modifications to the amino acid sequence (e.g., an acyl moiety or a palmitoyl moiety).

Technical and scientific terms used herein have the meaning commonly understood by one of ordinary skill in the art to which the present application pertains, unless otherwise defined. Reference is made herein to various methodologies and materials known to those of skill in the art. Standard reference works setting forth the general principles of peptide synthesis include W. C. Chan and P. D. White., "Fmoc Solid Phase Peptide Synthesis: A Practical Approach", Oxford University Press, Oxford (2004). In addition, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The terms "peptide," "polypeptide," "protein," and "protein fragment" are used interchangeably herein to refer to a polymer of two or more amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. The term "peptide" further includes peptides that have undergone post-translational or post-synthesis modifications, for example, glycosylation, acetylation, phosphorylation, amidation, derivatization by known protecting/blocking groups, proteolytic cleavage, or modification by non-naturally occurring amino acids. A "peptide" can be part of a fusion peptide comprising additional components such as, an Fc domain or an albumin domain, to increase half-life. A peptide as described herein can also be derivatized in a number of different ways.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refer to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid Amino acid mimetics refer to chemical compounds that have a structure that is different from the general chemical structure of an amino acid, but that function similarly to a naturally occurring amino acid. The terms "amino acid" and "amino acid residue" are used interchangeably throughout.

The term "isolated" refers to the state in which peptides or nucleic acids, will generally be in accordance with the present disclosure. Isolated peptides and isolated nucleic acids will be free or substantially free of material with which they are naturally associated such as other peptides or nucleic acids with which they are found in their natural environment, or the environment in which they are prepared (e.g. cell culture) when such preparation is by recombinant DNA technology practiced in vitro or in vivo. Peptides and nucleic acid can be formulated with diluents or adjuvants and still for practical purposes be isolated—for example the peptides will normally be mixed with gelatin or other carriers if used to coat microtitre plates for use in immunoassays, or will be mixed with pharmaceutically acceptable carriers or diluents when used in diagnosis or therapy.

A "recombinant" peptide refers to a peptide produced via recombinant DNA technology. Recombinantly produced peptides expressed in host cells are considered isolated for the purpose of the present disclosure, as are native or recombinant polypeptides which have been separated, fractionated, or partially or substantially purified by any suitable technique.

The terms "fragment," "analog," "derivative," or "variant," when referring to a peptide as provided herein, include any peptide that has at least some activity of a corresponding native peptide, e.g., GLP-1. As used herein, the term "GLP-1 peptide analog" refers to a peptide that has at least some activity of GLP-1, e.g., binding to GLP-1 receptor. An "analog," "derivative," or "variant" peptide can contain a chemical modifications, e.g., chemical modifications intended to improve metabolic stability including those involve additional chemical manipulation following synthesis of the main peptide chain. Examples of manipulation include lactamization, disulfide bridge closure, lipidation and/or PEGylation.

The terms "lipid modified amino acid" and "lipidated amino acid" are used interchangeably herein, and refer to an amino acid, typically a lysine or cysteine, which has a lipid moiety attached. The terms "lipidated polypeptide," "lipoprotein," and the like refer to a peptide or polypeptide that includes one or more lipid modified amino acids. Representative examples of lipids, lipid moieties, and linkers are provided in WO 2016/198555 (see e.g., FIG. 1 therein.)

As used herein, "proteolytic degradation" means the breakdown of peptides into smaller peptides or even amino acids, generally caused by the hydrolysis of a peptide bond by enzymes. The terms "composition" or "pharmaceutical composition" refer to compositions containing a peptide or polypeptide provided herein, along with e.g., pharmaceutically acceptable carriers, excipients, or diluents for administration to a subject in need of treatment.

Lipidated peptides that are "substantially resistant" to proteolytic degradation can, for example, remain at least about 50% intact following exposure to an enzyme in conditions that the enzyme is generally active (e.g., suitable pH, temperature, other environmental conditions) for a defined period of time. Lipidated peptides provided herein can be substantially resistant to proteolytic degradation for a period of at least 4 hours, at least 8 hours, at least 12 hours, at least 24 hours, at least 36 hours, at least 48 hours, at least 72 hours, at least 96 hours, at least 120 hours, at least 144 hours, at least 168 hours, at least 192 hours, at least 216 hours, at least 240 hours, or about 36 hours to about 240 hours, about 48 hours to 240 hours, about 72 hours to about 240 hours, about 96 hours to about 240 hours, about 120 hours to about 240 hours, about 144 hours to about 240 hours, about 168 hours to about 240 hours, about 192 hours to about 240 hours, or about 216 hours to about 240 hours. In certain embodiments, at least about 60% of the lipidated peptide remains intact following exposure to an enzyme in conditions that the enzyme is generally active for a defined period of time, for example, at least about 70%, at least about 80%, at least about 85%, at least about 90%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, or at least about 100% of the lipidated peptide remains intact following exposure to an enzyme in conditions that the enzyme is generally active for a defined period of time.

The term "pharmaceutical composition" refers to a composition containing a GLP-1 agonist peptide provided herein, along with e.g., pharmaceutically acceptable carriers, excipients, or diluents for administration to a subject in need of treatment, e.g., a human subject.

The term "pharmaceutically acceptable" refers to compositions that are, within the scope of sound medical judgment, suitable for contact with the tissues of human beings and animals without excessive toxicity or other complications commensurate with a reasonable benefit/risk ratio.

The term "pharmaceutically acceptable carrier" refers to one or more non-toxic materials that do not interfere with the effectiveness of the biological activity of the lipidated peptides.

An "effective amount" is that amount of a peptide or formulation provided herein, the administration of which to a subject, either in a single dose or as part of a series, is effective for treatment, i.e., to reduce the severity of a disease or disorder (or one or more symptoms thereof), ameliorate one or more symptoms of such a disease or disorder, prevent the advancement of such a disease or disorder, cause regression of such a disease or disorder, or enhance or improve the therapeutic effect(s) of another therapy.

The term "subject" is meant any subject, particularly a mammalian subject, in need of treatment with a peptide provided herein. Mammalian subjects include, but are not limited to, humans, dogs, cats, guinea pigs, rabbits, rats, mice, horses, cattle, bears, cows, apes, monkeys, orangutans, and chimpanzees, and so on. In one aspect, the subject is a human subject.

As used herein, a "subject in need thereof" refers to an individual for whom it is desirable to treat, e.g., a subject with a condition caused or characterized by hyperglycemia or impaired insulin release, a subject with diabetes (e.g., type-2 diabetes), an obese subject or a subject prone to obesity for whom it is desirable to facilitate weight or body fat loss, weight or body fat maintenance, or to prevent or minimize weight gain over a specified period of time.

Terms such as "treating" or "treatment" or "to treat" refer to therapeutic measures that cure and/or halt progression of a diagnosed pathologic condition or disorder. Terms such as "preventing" refer to prophylactic or preventative measures that prevent and/or slow the development of a targeted pathologic condition or disorder. Thus, those in need of treatment include those already with the disease or condition. Those in need of prevention include those prone to have the disease or condition and those in whom the disease or condition is to be prevented. For example, the phrase "treating a patient" having a disease or condition caused or characterized by excess body weight refers to reducing the severity of the disease or condition to an extent that the subject no longer suffers discomfort and/or altered function due to it. The phrase "preventing" a disease or condition caused or characterized by excess body weight refers to reducing the potential for the disease or condition and/or reducing the occurrence of the disease or condition (for example a relative reduction in occurrence as compared to untreated patients).

Terms such as "decreasing the severity" refer to therapeutic measures that slow down or lessen the symptoms of a diagnosed pathologic condition or disorder. For example, the phrase "decreasing the severity" of diabetes refers to reducing the severity of the disease (for example, a reduction in symptoms when compared to untreated patients or an increase in glucose control).

II. GLP-1 Peptide Analogs

GLP-1 peptide analogs that can be orally administered are provided herein. A GLP-1 peptide analog is a peptide that has at least some activity of GLP-1, e.g., binding to GLP-1 receptor. The native amino acid sequence of GLP-1 (7-36) is HAEGTFTSDVSSYLEGQAAKEFIAWLVKGR (SEQ ID NO:1).

Exemplary GLP-1 peptide analogs for oral administration are provided in WO 2015/086686 and WO 2016/198544, each of which is herein incorporated by reference in its entirety.

In some embodiments, the GLP-1 peptide analog is a bislipidated GLP-1 peptide analog. Exemplary bislipidated GLP-1 peptide analogs are provided in Table 1.

TABLE 1

Exemplary bislipidated GLP-1 peptide analogs

| SEQ ID NO. | Bislipidated GLP-1 peptide analog |
|---|---|
| 2 | Free-H-[AIB]-EGS-[αMePhe]-TSDV-[αMeSer]-SK[(PEG$_2$)$_2$-γE-Lauroyl]-LEGEAA-[αMeLys]-E-[αMePhe]-IAK[(PEG$_2$)$_2$-γE-Lauroyl]-VVEGG-amide (FIG. 1H) |
| 3 | Free-H-[AIB]-EGS-[αMePhe]-TSDV-[αMeSer]-S-[αMePhe]-LEGEAAK[(PEG$_2$)$_2$-γE-Stearate]-E-[αMePhe]-IA-[αMePhe]-VV-[αMeLys]-GG-amide (FIG. 1A) |
| 4 | Free-H-[AIB]-EGS-[αMePhe]-TSDV-[αMeSer]-S-[αMePhe]-LEGEAAK[(PEG$_2$)$_2$-γE-Stearate]-EFIA-[αMePhe]-VV-[αMeLys]-GG-amide (FIG. 1B) |
| 5 | Free-H-[AIB]-EGS-[αMePhe]-TSDVSK[(PEG$_2$)$_2$-γE-Lauroyl]-YLEGEAA-[αMeLys]-EFIAK[(PEG$_2$)$_2$-γE-Lauroyl]-VVEGG-amide (FIG. 1C) |
| 6 | Free-H-[AIB]-EGS-[αMePhe]-TSDV-[αMeSer]-SK[(PEG$_2$)$_2$-γE-Lauroyl]-LEGEAA-[αMeLys]-EFIAK[(PEG$_2$)$_2$-γE-Lauroyl]-VVEGG-amide (FIG. 1D) |
| 7 | Free-H-[AIB]-EGS-[αMePhe]-TSDVSK[(PEG$_2$)$_2$-γE-Lauroyl]-YLEGEAA-[αMeLys]-EFIAWK[(PEG$_2$)$_2$-γE-Lauroyl]-VEGG-amide (FIG. 1E) |
| 8 | Free-H-[AIB]-EGS-[αMePhe]-TSDK[(PEG$_2$)$_2$-γE-Lauroyl]-SSYLEGEAA-[αMeLys]-EFIK[(PEG$_2$)$_2$-γE-Lauroyl]-WVVEGG-amide (FIG. 1F) |
| 9 | Free-H-[AIB]-EGS-[αMePhe]-TSDV-[αMeSer]-SYK[(PEG$_2$)$_2$-γE-Lauroyl]-EGEAA-[αMeLys]-EFIAK[(PEG$_2$)$_2$-γE-Lauroyl]-VVEGG-amide (FIG. 1G) |
| 10 | Free-H-[AIB]-EGS-[αMePhe]-TSDV-[αMeSer]-SK[(PEG$_2$)$_2$-γE-Palmitoyl]-LEGEAA-[αMeLys]-E-[αMePhe]-IAK[(PEG$_2$)$_2$-γE-Palmitoyl]-VVEGG-amide (FIG. 1I) |
| 12 | Free-H-(Aib)2-EG-(S)5-(α-MeF)6-TSDV10-(α-MeS)11-S-K(ε-(PEG)2-(PEG)2-γE-Lauroyl)13-LE15 G-(E)17-AA-(α-MeK)20 E-(Tyr(OMe)22 IA-K(ε-(PEG)2-(PEG)2-γE-Lauroyl)25-(V)26-V-(E)28-G-(G)30-amide (FIG. 1K) |
| 13 | Free-H-(Aib)2-EG-(S)5-(α-MeF)6-TSDV10-(α-MeS)11-S-K(ε-(PEG)2-(PEG)2-γE-Lauroyl)13-LE15 G-(E)17-AA-(α-MeK)20 E-(Nle)22 IA-K(ε-(PEG)2-(PEG)2-γE-Lauroyl)25-(V)26-V-(E)28-G-(G)30-amide (FIG. 1L) |

TABLE 1-continued

Exemplary bislipidated GLP-1 peptide analogs

| SEQ ID NO. | Bislipidated GLP-1 peptide analog |
|---|---|
| 14 | Free-H-(Aib)2-EG-(S)5-(α-MeF)6-TSDV10-(α-MeS)11-S-K(ε-(PEG)2-(PEG)2-γE-Myristoyl)13-LE15 G-(E)17-AA-(α-MeK)20 E-(α-MeF)22 IA-K(ε-(PEG)2-(PEG)2-γE-Myristoyl)25-(V)26-V-(E)28-G-(G)30-amide (FIG. 1M) |
| 15 | Free-H-(Aib)2-EG-(S)5-(α-MeF)6-TSDV10-(α-MeS)11-S-K(ε-(PEG)2-(PEG)2-γE-Stearoyl)13-LE15 G-(E)17-AA-(α-MeK)20 E-(α-MeF)22 IA-K(ε-(PEG)2-(PEG)2-γE-Stearoyl)25-(V)26-V-(E)28-G-(G)30-amide (FIG. 1N) |

In some embodiments, the GLP-1 peptide analog comprises the lipidated peptide of SEQ ID NO:3 or a salt thereof (e.g., an ammonium acetate salt). In some embodiments, the GLP-1 peptide analog consists of the lipidated peptide of SEQ ID NO:3 or a salt thereof (e.g., an ammonium acetate salt).

In some embodiments, the GLP-1 peptide analog comprises the lipidated peptide of SEQ ID NO:4 or a salt thereof (e.g., an ammonium acetate salt). In some embodiments, the GLP-1 peptide analog consists of the lipidated peptide of SEQ ID NO:4 or a salt thereof (e.g., an ammonium acetate salt).

In some embodiments, the GLP-1 peptide analog comprises the lipidated peptide of SEQ ID NO:5 or a salt thereof (e.g., an ammonium acetate salt). In some embodiments, the GLP-1 peptide analog consists of the lipidated peptide of SEQ ID NO:5 or a salt thereof (e.g., an ammonium acetate salt).

In some embodiments, the GLP-1 peptide analog comprises the lipidated peptide of SEQ ID NO:6 or a salt thereof (e.g., an ammonium acetate salt). In some embodiments, the GLP-1 peptide analog consists of the lipidated peptide of SEQ ID NO:6 or a salt thereof (e.g., an ammonium acetate salt).

In some embodiments, the GLP-1 peptide analog comprises the lipidated peptide of SEQ ID NO:7 or a salt thereof (e.g., an ammonium acetate salt). In some embodiments, the GLP-1 peptide analog consists of the lipidated peptide of SEQ ID NO:7 a salt thereof (e.g., an ammonium acetate salt).

In some embodiments, the GLP-1 peptide analog comprises the lipidated peptide of SEQ ID NO:8 a salt thereof (e.g., an ammonium acetate salt). In some embodiments, the GLP-1 peptide analog consists of the lipidated peptide of SEQ ID NO:8 or a salt thereof (e.g., an ammonium acetate salt).

In some embodiments, the GLP-1 peptide analog comprises the lipidated peptide of SEQ ID NO:9 or a salt thereof (e.g., an ammonium acetate salt). In some embodiments, the GLP-1 peptide analog consists of the lipidated peptide of SEQ ID NO:9 or a salt thereof (e.g., an ammonium acetate salt).

In some embodiments, the GLP-1 peptide analog comprises the lipidated peptide of SEQ ID NO:2 or a salt thereof (e.g., an ammonium acetate salt). In some embodiments, the GLP-1 peptide analog comprises the lipidated peptide of SEQ ID NO:2 or an ammonium acetate salt thereof (MEDI7219). In some embodiments, the GLP-1 peptide analog consists of the lipidated peptide of SEQ ID NO:2 or a salt thereof (e.g., an ammonium acetate salt). In some embodiments, the GLP-1 peptide analog consists of the lipidated peptide of SEQ ID NO:2 or an ammonium acetate salt thereof (MEDI7219).

In some embodiments, the GLP-1 peptide analog comprises the lipidated peptide of SEQ ID NO:10 or a salt thereof (e.g., an ammonium acetate salt). In some embodiments, the GLP-1 peptide analog consists of the lipidated peptide of SEQ ID NO:10 or a salt thereof (e.g., an ammonium acetate salt).

In some embodiments, the GLP-1 peptide analog comprises the lipidated peptide of SEQ ID NO:12 or a salt thereof (e.g., an ammonium acetate salt). In some embodiments, the GLP-1 peptide analog consists of the lipidated peptide of SEQ ID NO:12 or a salt thereof (e.g., an ammonium acetate salt).

In some embodiments, the GLP-1 peptide analog comprises the lipidated peptide of SEQ ID NO:13 or a salt thereof (e.g., an ammonium acetate salt). In some embodiments, the GLP-1 peptide analog consists of the lipidated peptide of SEQ ID NO:13 or a salt thereof (e.g., an ammonium acetate salt).

In some embodiments, the GLP-1 peptide analog comprises the lipidated peptide of SEQ ID NO:14 or a salt thereof (e.g., an ammonium acetate salt). In some embodiments, the GLP-1 peptide analog consists of the lipidated peptide of SEQ ID NO:15 or a salt thereof (e.g., an ammonium acetate salt).

In some embodiments, the GLP-1 peptide analog is a synthetic peptide.

In some embodiments, the GLP-1 peptide analog (e.g., SEQ ID NO:2 or an ammonium acetate salt thereof (MEDI7219)) is lipidated. In some embodiments, the GLP-1 peptide analog (e.g., SEQ ID NO:2 or an ammonium acetate salt thereof (MEDI7219)) is bislipidated. In some embodiments, the GLP-1 peptide analog (e.g., SEQ ID NO:2 or an ammonium acetate salt thereof (MEDI7219)) contains two lipidated lysines. Methods of producing lipidated peptides are further described herein.

In some embodiments, the GLP-1 peptide analog (e.g., SEQ ID NO:2 or an ammonium acetate salt thereof (MEDI7219)) is substantially resistant to proteolytic degradation. For example, in certain embodiments the GLP-1 peptide analog (e.g., SEQ ID NO:2 or an ammonium acetate salt thereof (MEDI7219)) is substantially resistant to DPP-IV, neprilysin, α-chymotrypsin, plasmin, thrombin, kallikrein, trypsin, elastase, and/or pepsin degradation.

In some embodiments the GLP-1 peptide analog (e.g., SEQ ID NO:2 or an ammonium acetate salt thereof (MEDI7219)) at least maintains substantially the same receptor potency as compared to a corresponding non-lipidated peptide. In some embodiments, the GLP-1 peptide analog (e.g., SEQ ID NO:2 or an ammonium acetate salt thereof (MEDI7219)) at least maintains substantially the same receptor selectivity as a compared to corresponding non-lipidated peptide. In some embodiments, the GLP-1 peptide analog (e.g., SEQ ID NO:2 or an ammonium acetate salt thereof (MEDI7219)) at least maintains substantially the same receptor potency and selectivity as a compared to corresponding non-lipidated peptide.

The biological activity of a GLP-1 peptide analog can be evaluated, for example, by assessing the ability of the peptide to activate a receptor (e.g., a GLP-1 receptor). Peptide activation of such receptors results in downstream accumulation of cAMP second messenger which can be measured in a functional activity assay. As such, in certain embodiments, the GLP-1 peptide analog (e.g., SEQ ID NO:2 or an ammonium acetate salt thereof (MEDI7219)) exhibits an in vitro potency at the GLP-1 receptor as shown by an EC50 in a cAMP assay of less than 200 pM, less than 100 pM, less than 50 pM, less than 25 pM, less than 20 pM, less than 15 pM, less than 10 pM, less than 5 pM, or less than 4 pM. In certain embodiments, the GLP-1 peptide analog (e.g., SEQ ID NO:2 or an ammonium acetate salt thereof (MEDI7219)) exhibits an in vitro potency at the GLP-1 receptor as shown by an EC50 in a cAMP assay of about 3.9 pM, for example using a primary assay as described in WO 2016/198544, which is herein incorporated by reference in its entirety. In certain embodiments, the GLP-1 peptide analog (e.g., SEQ ID NO:2 or an ammonium acetate salt thereof (MEDI7219)) exhibits an in vitro potency at the GLP-1 receptor as shown by an EC50 in a cAMP assay of about 116 pM, for example using an INSle assay as described in WO 2016/198544, which is herein incorporated by reference in its entirety.

III. Methods of Preparing Lipidated Peptides

While various methods of attaching lipids and lipid moieties to peptides are known, provided herein is at least one representative method of preparing lipidated peptides.

In certain embodiments, lipidated peptides can be prepared as C-terminal carboxamides, such as on NovaSyn® TGR resin. In certain embodiments, amino acids (both natural and unnatural) can be coupled at ambient temperature, such as by using HCTU/DIPEA in NMP, capping residual functionality with a solution of acetic anhydride and pyridine. In such methods, the N-Fmoc group can be deblocked using piperidine in DMF (20% v/v) at ambient temperature and the C-terminal residue incorporated as the N-Boc-protected form, e.g. Boc-His(Trt)-OH or Boc-Tyr (tBu)-OH or equivalent. At the position(s) of lipidation Fmoc-Lys(Mmt)-OH can be incorporated into the peptide backbone during automated assembly and upon completion the Mmt protecting group(s) can be removed manually and selectively by treatment of the synthesis resin with 1% TFA, 2% TIPS, DCM (10×1 minute, 20.0 mL/g). The acidified resin can be quenched, such as with 5% DIPEA/NMP, and the exposed lysine amino-function(s) acylated, PEGylated or lipidated as required prior to peptide cleavage.

Crude peptides can be cleaved from the resin support by treatment with a suitable cleavage cocktail. In certain embodiments the cocktail consists of TFA (95% v/v), TIPS (2.5% v/v), and water (2.5% v/v) with agitation (3×1 hour at ambient temperature). Cleavage aliquots can be combined, concentrated by rotary evaporation and precipitated by addition of cold diethyl ether, isolating the solids by centrifugation. The crude peptides can be dried under a flow of dry nitrogen, reconstituted in a suitable aqueous buffer and filtered prior to chromatographic purification.

Crude mono-lipidated peptides can be dissolved in a solution of acetic acid/acetonitrile/water (1:5:50 v/v) and filtered. The crude filtrates can be chromatographed, such as over an Agilent Polaris C8-A stationary phase (21.2×250 mm, 5 micron) eluting with a linear solvent gradient of 10-70%, 15-80% or 20-90% MeCN (0.1% TFA v/v) in water (0.1% TFA v/v) over 30 minutes using a Varian SD-1 PrepStar binary pump system, monitoring by UV absorption at 210 nm. The peptide-containing fractions can then be pooled, frozen (dry-ice/acetone) and lyophilized.

Crude bis-lipidated peptides can be dissolved, such as in 0.1M ammonium bicarbonate solution (1:5 acetonitrile/water v/v, pH 8.0) and filtered. The crude filtrates can be chromatographed, such as over a Waters X-Bridge C18 stationary phase (19.0×250 mm, 5 micron) eluting with a linear solvent gradient of 20-90% B against A over 30 minutes using a Varian SD-1 PrepStar binary pump system, monitoring by UV absorption at 210 nm (A=0.1M ammonium bicarbonate in water, B=0.1M ammonium bicarbonate in 1:2 water/acetonitrile). The peptide-containing fractions can then pooled, frozen (dry-ice/acetone) and lyophilized.

The peptide sequence can be a GLP-1 analog sequence such as that provided in SEQ ID NO:2. The lipid or lipid moiety can be any such as disclosed herein, including but not limited to: K(ε-(PEG)$_2$-(PEG)$_2$-γE-Stearate); K(ε-γE-Palmitoyl); K(ε-(PEG)$_2$-(PEG)$_2$-γE-Stearate); K(γE-Palmitoyl); K(ε-(PEG)$_2$-(PEG)$_2$-(PEG)$_2$-Stearoyl); K(ε-γE-Lauroyl); K(ε-γE-γE-Lauroyl); K(ε-γE-γE-γE-Lauroyl); K(ε-Ahx-Lauroyl); K(ε-Ahx-Ahx-Lauroyl); K(ε-Ahx-Ahx-Ahx-Lauroyl); K(ε-(PEG)$_2$-Lauroyl); K(ε-(PEG)$_2$-(PEG)$_2$-Lauroyl); K(ε-(PEG)$_2$-(PEG)$_2$-(PEG)$_2$-Lauroyl); K(ε-γE-12-(4-carboxyphenoxy)dodecanoyl); K(ε-γE-γE-12-(4-carboxyphenoxy)dodecanoyl); K(ε-γE-γE-γE-12-(4-carboxyphenoxy)dodecanoyl); K(ε-Ahx -12-(4-carboxyphenoxy)dodecanoyl); K(ε-Ahx-Ahx-12-(4-carboxyphenoxy)dodecanoyl); K(ε-Ahx-Ahx-Ahx-12-(4-carboxyphenoxy)dodecanoyl); K(ε-(PEG)$_2$-12-(4-carboxyphenoxy)dodecanoyl); K(ε-(PEG)$_2$-(PEG)$_2$-12-(4-carboxyphenoxy)dodecanoyl); K(ε-(PEG)$_2$-(PEG)$_2$-(PEG)$_2$-12-(4-carboxyphenoxy)dodecanoyl); K(ε-γE-Stearoyl); K(ε-γE-γE-Stearoyl); K(ε-γE-γE-γE-Stearoyl); K(ε-Ahx-Stearoyl); K(ε-Ahx-Ahx-Stearoyl); K(ε-Ahx-Ahx-Ahx-Stearoyl); K(ε-(PEG)$_2$-Stearoyl); K(ε-(PEG)$_2$-(PEG)$_2$-Stearoyl); K(ε-(PEG)$_2$-(PEG)$_2$-(PEG)$_2$-Stearoyl); K(ε-γE-Stearate); K(ε-γE-γE-Stearate); K(ε-γE-γE-γE-Stearate); K(ε-Ahx-Stearate); K(ε-Ahx-Ahx-Stearate); K(ε-Ahx-Ahx-Ahx-Stearate); K(ε-(PEG)$_2$-Stearate); K(ε-(PEG)$_2$-(PEG)$_2$-Stearate); K(ε-(PEG)$_2$-(PEG)$_2$-(PEG)$_2$-Stearate), and any combination thereof.

IV. Methods of Preparing Synthetic Peptides

Also provided are methods of preparing synthetic peptides.

In some embodiments, the methods suitably comprise identifying at least one native amino acid residue in the peptide for substitution. In other embodiments, the methods suitably comprise identifying at least two native amino acid residues in the peptide for substitution. Alpha-methyl functionalized amino acids can then substituted for the identified native amino acid residues.

As described throughout, the synthetic peptides prepared by the methods provided herein suitably maintain substantially the same or exhibit increased receptor potency and in some cases selectivity as a corresponding synthetic peptide that does not comprise the substitutions. In addition, the synthetic peptides prepared according to the methods described herein can also be substantially resistant to proteolytic degradation.

Suitably in the methods provided herein the substituted alpha-methyl functionalized amino acids correspond to the substituted native amino acid residues, and in additional embodiments, the substituted alpha-methyl functionalized amino acids correspond to the same class as the substituted native amino acid residues.

In further embodiments, the substituted alpha-methyl functionalized amino acids can be alpha-methyl phenylalanine. In exemplary embodiments, alpha-methyl phenylalanine is substituted for corresponding native amino acids, though in further embodiments of the methods, the alpha-methyl phenylalanine does not have to correspond to the same native amino acids for which the substitution is occurring.

In certain embodiments, the synthetic peptides prepared according to the methods described herein can be substantially resistant to one or more of DPP-IV, neprilysin, α-chymotrypsin, plasmin, thrombin, kallikrein, trypsin, elastase and pepsin degradation.

In embodiments, synthetic peptides can be prepared as C-terminal carboxamides on NOVASYN® TGR resin. Amino acids (both natural and unnatural) can be coupled at ambient temperature using HCTU/DIPEA in NMP, capping residual functionality with a solution of acetic anhydride and pyridine. Fmoc is suitably deblocked in using piperidine in DMF at ambient temperature.

As described herein, identifying at least one native amino acid residue in the peptide for substitution suitably comprises identifying amino acids at sites susceptible to enzymatic cleavage. Exemplary methods of identifying amino acids at sites susceptible to enzymatic cleavage are well known in the art. In certain embodiments, methods of identifying amino acids at sites susceptible to enzymatic cleavage suitably comprise exposing a natural peptide (e.g., a wild-type peptide) to a single enzyme under conditions in which the enzyme is active (e.g., suitable pH, buffer conditions, temperature, etc.) for a pre-determined amount of time and measuring the enzymatic degradation products of the peptide. Exemplary methods for measuring the enzymatic degradation products include, for example, reverse-phase liquid chromatography-mass spectrometry.

Peptide solutions can be added to solutions of a protease. The peptide and enzyme can be co-incubated, suitably at about 37° C. Aliquots of the incubated peptide-enzyme mixture can be withdrawn periodically, quenched to arrest proteolytic activity, and analyzed by liquid chromatography-mass spectrometry (LC/MS). Analytes can be detected by both UV absorption (e.g., at 210 nm) and by ionization using a mass detector (ESI+ mode). Peptidic species (fragments) deriving from enzymatic cleavage of peptides can be analyzed post-process, and their molecular masses can be used to identify the precise cleavage position (highlighting the scissile bond in each case).

In embodiments, the methods can be used to prepare synthetic GLP-1 peptide analogs.

In further embodiments, methods of preparing a proteolytically stable peptide are provided. Suitably, such methods comprise exposing a peptide to one or more proteases, identifying at least two native amino acid residues which are sites susceptible to proteolytic cleavage, and substituting alpha-methyl functionalized amino acids for the identified amino acid residues.

As described throughout, suitably such methods provide a synthetic peptide that maintains substantially the same or exhibits increased receptor potency and in some cases selectivity as a corresponding synthetic peptide that does not comprise the substitution(s). In further embodiments, the methods also provide a synthetic peptide that is substantially resistant to proteolytic degradation.

Suitably in the methods provided herein, the substituted alpha-methyl functionalized amino acids correspond to the substituted native amino acid residues, and in additional embodiments, the substituted alpha-methyl functionalized amino acids correspond to the same class as the substituted native amino acid residues.

In still further embodiments, the substituted alpha-methyl functionalized amino acids can be selected from alpha-methyl functionalized Histidine, alpha-methyl functionalized Alanine, alpha-methyl functionalized Isoleucine, alpha-methyl functionalized Arginine, alpha-methyl functionalized Leucine, alpha-methyl functionalized Asparagine, alpha-methyl functionalized Lysine, alpha-methyl functionalized Aspartic acid, alpha-methyl functionalized Methionine, alpha-methyl functionalized Cysteine, alpha-methyl functionalized Phenylalanine, alpha-methyl functionalized Glutamic acid, alpha-methyl functionalized Threonine, alpha-methyl functionalized Glutamine, alpha-methyl functionalized Tryptophan, alpha-methyl functionalized Glycine, alpha-methyl functionalized Valine, alpha-methyl functionalized Ornithine, alpha-methyl functionalized Proline, alpha-methyl functionalized Selenocysteine, alpha-methyl functionalized Serine and alpha-methyl functionalized Tyrosine.

In further embodiments, the substituted alpha-methyl functionalized amino acids can be alpha-methyl phenylalanine and/or alpha-methyl lysine. In exemplary embodiments, alpha-methyl phenylalanine and/or alpha-methyl lysine can be substituted for corresponding native amino acids, though in further embodiments of the methods, the alpha-methyl phenylalanine and/or alpha-methyl lysine do not have to correspond to the same native amino acids for which the substitution is occurring.

In certain embodiments, the synthetic peptides prepared according to the methods described herein can be substantially resistant to one or more of DPP-IV, neprilysin, α-chymotrypsin, plasmin, thrombin, kallikrein, trypsin, elastase and pepsin degradation.

V. Formulations Comprising GLP-1 Peptide Analogs

Formulations for oral administration of GLP-1 peptide analogs are provided herein. Suitably such formulations comprise a lipidated peptide as described herein (e.g., SEQ ID NO:2 or an ammonium acetate salt thereof (MEDI7219)) and a carrier, e.g., a pharmaceutically acceptable carrier.

Oral formulations as described herein can be formulated for a particular dosage form. Dosage regimens can be adjusted to provide the optimum response. It can be useful to formulate compositions in dosage unit forms for ease of administration and uniformity of dosage. Dosage unit forms as used herein refers to physically discrete units suited as unitary dosages for the subjects to be treated; each unit contains a predetermined quantity of a lipidated peptide calculated to produce a therapeutic effect in association with the required pharmaceutical carrier. For example, the oral formulation can comprise a dose of about 0.1 to about 100 mg of a GLP-1 peptide analog (e.g., SEQ ID NO:2 or an ammonium acetate salt thereof (MEDI7219)).

The oral formulation can comprise about 0.0625 to about 36 mg of a GLP-1 peptide analog (e.g., SEQ ID NO:2 or an ammonium acetate salt thereof (MEDI7219)). The oral formulation can comprise about 0.25 to about 36 mg of a GLP-1 peptide analog (e.g., SEQ ID NO:2 or an ammonium acetate salt thereof (MEDI7219)). The oral formulation can comprise about 0.5 to about 36 mg of a GLP-1 peptide analog (e.g., SEQ ID NO:2 or an ammonium acetate salt thereof (MEDI7219)). The oral formulation can comprise about 1 to about 36 mg of a GLP-1 peptide analog (e.g., SEQ ID NO:2 or an ammonium acetate salt thereof (MEDI7219)). The oral formulation can comprise about 3 to about 36 mg of a GLP-1 peptide analog (e.g., SEQ ID NO:2 or an ammonium acetate salt thereof (MEDI7219)). The oral formulation can comprise about 6 to about 36 mg of a GLP-1 peptide analog (e.g., SEQ ID NO:2 or an ammonium acetate salt thereof (MEDI7219)). The oral formulation can comprise about 9 to about 36 mg of a GLP-1 peptide analog (e.g., SEQ ID NO:2 or an ammonium acetate salt thereof (MEDI7219)). The oral formulation can comprise about 18 to about 36 mg of a GLP-1 peptide analog (e.g., SEQ ID NO:2 or an ammonium acetate salt thereof (MEDI7219)). The GLP-1 peptide analog (e.g., SEQ ID NO:2 or an ammonium acetate salt thereof (MEDI7219)) can be about 0.0128% to about 7.36% of the oral formulation. The GLP-1 peptide analog (e.g., SEQ ID NO:2 or an ammonium acetate salt thereof (MEDI7219)) can be about 0.0256% to about 7.36% of the oral formulation The oral formulation can comprise about 0.25 to about 18 mg of a GLP-1 peptide analog (e.g., SEQ ID NO:2 or an ammonium acetate salt thereof (MEDI7219)). The oral formulation can comprise about 0.5 to about 18 mg of a GLP-1 peptide analog (e.g., SEQ ID NO:2 or an ammonium acetate salt thereof (MEDI7219)). The oral formulation can comprise about 1 to about 18 mg of a GLP-1 peptide analog (e.g., SEQ ID NO:2 or an ammonium acetate salt thereof (MEDI7219)). The oral formulation can comprise about 3 to about 18 mg of a GLP-1 peptide analog (e.g., SEQ ID NO:2 or an ammonium acetate salt thereof (MEDI7219)). The oral formulation can comprise about 6 to about 18 mg of a GLP-1 peptide analog (e.g., SEQ ID NO:2 or an ammonium acetate salt thereof (MEDI7219)). The oral formulation can comprise about 9 to about 18 mg of a GLP-1 peptide analog (e.g., SEQ ID NO:2 or an ammonium acetate salt thereof (MEDI7219)).

The oral formulation can comprise about 0.25 to about 9 mg of a GLP-1 peptide analog (e.g., SEQ ID NO:2 or an ammonium acetate salt thereof (MEDI7219)). The oral formulation can comprise about 0.5 to about 9 mg of a GLP-1 peptide analog (e.g., SEQ ID NO:2 or an ammonium acetate salt thereof (MEDI7219)). The oral formulation can comprise about 1 to about 9 mg of a GLP-1 peptide analog (e.g., SEQ ID NO:2 or an ammonium acetate salt thereof (MEDI7219)). The oral formulation can comprise about 3 to about 9 mg of a GLP-1 peptide analog (e.g., SEQ ID NO:2 or an ammonium acetate salt thereof (MEDI7219)). The oral formulation can comprise about 6 to about 9 mg of a GLP-1 peptide analog (e.g., SEQ ID NO:2 or an ammonium acetate salt thereof (MEDI7219)).

The oral formulation can comprise about 0.25 to about 6 mg of a GLP-1 peptide analog (e.g., SEQ ID NO:2 or an ammonium acetate salt thereof (MEDI7219)). The oral formulation can comprise about 0.5 to about 6 mg of a GLP-1 peptide analog (e.g., SEQ ID NO:2 or an ammonium acetate salt thereof (MEDI7219)). The oral formulation can comprise about 1 to about 6 mg of a GLP-1 peptide analog (e.g., SEQ ID NO:2 or an ammonium acetate salt thereof (MEDI7219)). The oral formulation can comprise about 3 to about 6 mg of a GLP-1 peptide analog (e.g., SEQ ID NO:2 or an ammonium acetate salt thereof (MEDI7219)).

The oral formulation can comprise about 0.0625 mg of a GLP-1 peptide analog (e.g., SEQ ID NO:2 or an ammonium acetate salt thereof (MEDI7219)). The oral formulation can comprise about 0.125 mg of a GLP-1 peptide analog (e.g., SEQ ID NO:2 or an ammonium acetate salt thereof (MEDI7219)). The oral formulation can comprise about 0.5 mg of a GLP-1 peptide analog (e.g., SEQ ID NO:2 or an ammonium acetate salt thereof (MEDI7219)). The oral formulation can comprise about 1 mg of a GLP-1 peptide analog (e.g., SEQ ID NO:2 or an ammonium acetate salt thereof (MEDI7219)). The oral formulation can comprise about 3 mg of a GLP-1 peptide analog (e.g., SEQ ID NO:2 or an ammonium acetate salt thereof (MEDI7219)). The oral formulation can comprise about 4.5 mg of a GLP-1 peptide analog (e.g., SEQ ID NO:2 or an ammonium acetate salt thereof (MEDI7219)). The oral formulation can comprise about 6 mg of a GLP-1 peptide analog (e.g., SEQ ID NO:2 or an ammonium acetate salt thereof (MEDI7219)). The oral formulation can comprise about 9 mg of a GLP-1 peptide analog (e.g., SEQ ID NO:2 or an ammonium acetate salt thereof (MEDI7219)). The oral formulation can comprise about 18 mg of a GLP-1 peptide analog (e.g., SEQ ID NO:2 or an ammonium acetate salt thereof (MEDI7219)). The oral formulation can comprise about 36 mg of a GLP-1 peptide analog (e.g., SEQ ID NO:2 or an ammonium acetate salt thereof (MEDI7219)).

In one embodiment, the amount of active pharmaceutical ingredient (API) can be calculated by adjusting for pure peptide content, which can be calculated as an assay, encompassing content of ammonium, acetate and moisture, and multiplied by HPLC purity.

In order to achieve systemic exposure, the present invention provides oral formulations containing permeation enhancers. The permeation enhancer can be, for example, a bile salt, sodium chenodeoxycholate, chenodeoxycholic acid, a gallate derivative, propyl gallate, ethyl gallate, or a combination thereof.

The permeation enhancer can also be, for example, sodium caprate.

In one instance, the oral formulation comprises sodium chenodeoxycholate. The amount of sodium chenodeoxycholate can be about 1 mg to about 1500 mg. The amount of sodium chenodeoxycholate can be about 50 mg. The amount of sodium chenodeoxycholate can be about 65 mg. The amount of sodium chenodeoxycholate can be about 100 mg to about 800 mg. For example, the amount of sodium chenodeoxycholate can be about 100 mg. The amount of sodium chenodeoxycholate can be about 120 mg. The amount of sodium chenodeoxycholate can be about 130 mg. The amount of sodium chenodeoxycholate can be about 140 mg. The amount of sodium chenodeoxycholate can be about 150 mg. The amount of sodium chenodeoxycholate can be about 200 mg. The amount of sodium chenodeoxycholate can be about 260 mg. The amount of sodium chenodeoxycholate can be about 280 mg. The amount of sodium chenodeoxycholate can be about 290 mg. The amount of sodium chenodeoxycholate can be about 299 mg. The amount of sodium chenodeoxycholate can be about 300 mg. The amount of sodium chenodeoxycholate can be about 400 mg. The amount of sodium chenodeoxycholate can be about 500 mg. The amount of sodium chenodeoxycholate can be about 600 mg. The amount of sodium chenodeoxycholate can be about 700 mg. The amount of sodium chenodeoxycholate can be about 800 mg. Sodium chenodeoxycholate can be about 15% to about 25% of the oral formulation by weight. Sodium chenodeoxycholate can be about 20 to about 21%, e.g., about 20.5% of the oral formulation by weight.

In one instance, the oral formulation comprises propyl gallate. The amount of propyl gallate can be about 1 mg to about 3000 mg. For example, the amount of propyl gallate can be about 2 mg. For example, the amount of propyl gallate can be about 10 mg. For example, the amount of propyl gallate can be about 20 mg. For example, the amount of propyl gallate can be about 30 mg. For example, the amount of propyl gallate can be about 40 mg. For example, the amount of propyl gallate can be about 50 mg. For example, the amount of propyl gallate can be about 100 mg. For example, the amount of propyl gallate can be about 150 mg. The amount of propyl gallate can be about 200 mg to about 1600 mg. For example, the amount of propyl gallate can be about 200 mg. For example, the amount of propyl gallate can be about 300 mg. The amount of propyl gallate can be about 400 mg. For example, the amount of propyl gallate can be about 500 mg. For example, the amount of propyl gallate can be about 600 mg. For example, the amount of propyl gallate can be about 700 mg. The amount of propyl gallate can be about 800 mg. For example, the amount of propyl gallate can be about 900 mg. For example, the amount of propyl gallate can be about 1000 mg. For example, the amount of propyl gallate can be about 1100 mg. The amount of propyl gallate can be about 1200 mg. For example, the amount of propyl gallate can be about 1300 mg. For example, the amount of propyl gallate can be about 1400 mg. For example, the amount of propyl gallate can be about 1500 mg. The amount of propyl gallate can be about 1600 mg. Propyl gallate can be about 45% to about 55% of the oral formulation by weight. Propyl gallate can be about 40 to about 42%, e.g., about 40.9% of the oral formulation by weight.

In one instance, the oral formulation comprises sodium chenodeoxycholate and propyl gallate. The ratio of sodium chenodeoxycholate to propyl gallate can be about 150:1 to about 1:4. In one instance, the ratio of sodium chenodeoxycholate to propyl gallate is about 149.5:1. In one instance, the ratio of sodium chenodeoxycholate to propyl gallate is about 145:1. In one instance, the ratio of sodium chenodeoxycholate to propyl gallate is about 29:1. In one instance, the ratio of sodium chenodeoxycholate to propyl gallate is about 14:1. In one instance, the ratio of sodium chenodeoxycholate to propyl gallate is about 6.5:1. In one instance, the ratio of sodium chenodeoxycholate to propyl gallate is about 4:1. In one instance, the ratio of sodium chenodeoxycholate to propyl gallate is about 2:1. In one instance, the ratio of sodium chenodeoxycholate to propyl gallate is about 1:1. The ratio of sodium chenodeoxycholate to propyl gallate can be about 2:1 to about 1:4. The ratio of sodium chenodeoxycholate to propyl gallate can be about 1:1 to about 1:4. The ratio of sodium chenodeoxycholate to propyl gallate can be about 1:1 to about 1:3. In one instance, the ratio of sodium chenodeoxycholate to propyl gallate is about 1:2.

In one instance, the oral formulation comprises a combined amount of sodium chenodeoxycholate and propyl gallate from about 300 mg to about 1800 mg. Thus, the combined amount of sodium chenodeoxycholate and propyl gallate can be, for example, about 300 mg, about 600 mg, about 1200 mg, about 1800 mg, or about 2400 mg. In one instance, the combined amount of sodium chenodeoxycholate and propyl gallate is about 300 mg. In one instance, the oral formulation comprises a combined amount of sodium chenodeoxycholate and propyl gallate from about 50 mg to about 300 mg. In one instance, the combined amount of sodium chenodeoxycholate and propyl gallate is about 75 mg. In one instance, the combined amount of sodium chenodeoxycholate and propyl gallate is about 150 mg.

The oral formulations provided herein can also comprise a pH modifier or pH stabilizing excipient. The pH modifier or pH stabilizing excipient can, for example, maintain maximum solubility of the GLP-1 peptide analog (e.g., SEQ ID NO:2 or an ammonium acetate salt thereof (MEDI7219)) and/or the permeation enhancers (e.g., sodium chenodeoxycholate and propyl gallate) in the oral formulation. The pH modifier or pH stabilizing agent can, for example, allow for slightly alkaline pH in an otherwise variable intestinal pH environment upon tablet disintegration and dissolution. Slightly alkaline pH can be beneficial for peptide and sodium chenodeoxycholate solubility, which in turn increases systemic bioavailability of GLP-1 peptide analogs. The pH modifier or pH stabilizing excipient can be, for example, phosphate, glycinate, citrate, or Tris base.

The pH modifier or pH stabilizing excipient can be, for example Tris base. The amount of pH modifier (e.g., Tris base) can be 0 to 300 mg. The amount of pH modifier (e.g., Tris base) can be about 30 mg to about 40 mg, about 35 mg to about 40 mg, or about 36 to about 37 mg, for example, about 36.2 mg. Tris base can be about 5% to about 10% or about 7% to about 8%, e.g., about 7.41% or about 7.815% of the oral formulation by weight. As provided in the examples below, pH modifiers can increase the oral bioavailability of peptides from oral tablet formulations. This increase in bioavailability can be achieved via a synergistic effect of (i) a pH modifier that increases the pH of the GI tract environment to pH values that are favorable for dissolution of peptide and (ii) permeation enhancer excipients present in said formulations.

In the examples below, the site of absorption of peptide in gastrointestinal tract can significantly increase absolute oral bioavailability of the peptide. It is shown herein that delivery of oral peptide formulations to the proximal colon and to the proximal small bowel results in significantly higher absolute oral bioavailability as compared to delivery to the stomach. Matching the site of absorption with optimal tuning of the formulation for desired solubility at that site is one embodiment of this invention.

As provided herein, in order to increase absolute oral bioavailability of the peptide given in oral formulation, the site of delivery of such formulations within the gastrointestinal tract can be controlled via an enteric coating that dissolves at a specified pH. For instance, the oral formulation can dissolve at a pH of about 5 to about 7.5. Thus, the pH of the oral formulation can be about 5, about 5.5, about 6.0, about 7.0, or about 7.5. In one instance, the pH of the oral formulation is about 5.5. In one instance, the pH of the oral formulation is about 7.0. Dissolution of tablets at specific pH values can be controlled with enteric coatings of polymers that are insoluble at the low pH of the stomach and are soluble at pHs of 5.5 or above. In order to have optimal GLP-1 peptide agonist (e.g., SEQ ID NO:2 or an ammonium acetate salt thereof (MEDI7219)) absorption, the pH of solution upon stabilization of the oral formulation can be about 7.0 to about 9.0. As provided herein, enteric coating polymers can be amino alkyl methacrylate copolymers, methacrylic ester copolymers, or methacrylic acid copolymers. As provided herein, enteric coating polymers can be methacrylic acid copolymers (e.g., Eudragit®).

Pharmaceutical compositions for oral administration provided herein can comprise a mucoadhesive, e.g., cross-linked polyacrylic acid polymers (e.g., carbomers, e.g., Carbopor). The mucoadhesive component can enable the permeation enhancer to stay close to the GLP-1 peptide agonist and/or to the walls of the GI tract, thereby increasing bioavailability.

As provided herein, the oral formulation can be a sustained or delayed release formulation. Excipients such as cross-linked polyacrylic acid polymers (e.g., carbomers, e.g., Carbopol®) or methacrylic acid copolymers (e.g., Eudragit®) can be used in sustained or delayed release formulation. An enteric coat can, for example, allow the tablet to be intact in the harsh low pH environment of the stomach and to dissolve when the tablet reaches the proximal bowel where pH is 5.5 or above. This allows for GLP-1 agonist peptides to continue to be intact and readily available for systemic absorption upon dissolution.

The cross-linked polyacrylic acid polymers, e.g., Carbopol®, can be, for example, about 0.3% to about 10% of the oral formulation by weight. The cross-linked polyacrylic acid polymers, e.g., Carbopol®, can be, for example, about 0.3% to about 3% of the oral formulation by weight. The cross-linked polyacrylic acid polymers, e.g., Carbopol®, can be, for example, about 1% to about 10% of the oral formulation by weight. The cross-linked polyacrylic acid polymers, e.g., Carbopol®, can be, for example, about 0.3%, about 1%, about 3%, or about 10% of the oral formulation by weight. The cross-linked polyacrylic acid polymers, e.g., Carbopol®, can be, for example, about 0.3%, about 0.9%, or about 1% of the oral formulation by weight.

The oral formulation can comprise, for example, about 1 mg to about 50 mg of cross-linked polyacrylic acid polymers, e.g., Carbopol®. The oral formulation can comprise, for example, about 1 mg to about 2 mg, e.g., about 1.5 mg, of cross-linked polyacrylic acid polymers, e.g., Carbopol®. The oral formulation can comprise, for example, about 4 mg to about 5 mg, e.g., about 4.9 mg, of cross-linked polyacrylic acid polymers, e.g., Carbopol®. The oral formulation can comprise, for example, about 14 mg to about 15 mg, e.g., about 14.6 mg, of cross-linked polyacrylic acid polymers, e.g., Carbopol®. The oral formulation can comprise, for example, about 48 mg to about 49 mg, e.g., about 48.8 mg, of cross-linked polyacrylic acid polymers, e.g., Carbopol®.

The cross-linked polyacrylic acid polymers, e.g., Carbopol®, can be, for example, Carbopol 71G. The amount of cross-linked polyacrylic acid polymers, e.g., Carbopol® (e.g., Carbopol 71G) can be, for example, about 1% to about 10% or about 1% to about 5% of the oral formulation by weight. In one instance, the amount of cross-linked polyacrylic acid polymers, e.g., Carbopol® (e.g., Carbopol 71G) is about 1% of the oral formulation by weight. In one instance, the amount of cross-linked polyacrylic acid polymers, e.g., Carbopol® (e.g., Carbopol 71G) is about 2.5% of the oral formulation by weight. In one instance, the amount of cross-linked polyacrylic acid polymers, e.g., Carbopol® (e.g., Carbopol 71G) is about 10% of the oral formulation by weight.

The amount of cross-linked polyacrylic acid polymers, e.g., Carbopol®, e.g., Carbopol® 71G in the oral formulation can be about 4.9 mg to about 48.8 mg. The amount of cross-linked polyacrylic acid polymers, e.g., Carbopol®, e.g., Carbopol® 71G in the oral formulation can be about 4.9 mg. The amount of cross-linked polyacrylic acid polymers, e.g., Carbopol®, e.g., Carbopol® 71G in the oral formulation can be about 48.8 mg.

In addition to Carbopol 71G, other grades of Carbopol polymers, such as Carbopol 971P may be used to achieve controlled release. The amount of cross-linked polyacrylic acid polymers, e.g., Carbopol® (e.g., Carbopol 971P) can be, for example, about 0.3% to about 3% of the oral formulation by weight. In one instance, the amount of cross-linked polyacrylic acid polymers, e.g., Carbopol® (e.g., Carbopol 971P) is about 0.63% of the oral formulation by weight. In one instance, the amount of cross-linked polyacrylic acid polymers, e.g., Carbopol® (e.g., Carbopol 971P) is about 3% of the oral formulation by weight.

The amount of cross-linked polyacrylic acid polymers, e.g., Carbopol®, e.g., Carbopol® 971P in the oral formulation can be up to 120 mg. The amount of cross-linked polyacrylic acid polymers, e.g., Carbopol®, e.g., Carbopol® 971P, in the oral formulation can be about 1.5 mg to about 14.6 mg. The amount of cross-linked polyacrylic acid polymers, e.g., Carbopol®, e.g., Carbopol® 971P, in the oral formulation can be about 1 mg to about 2 mg, e.g., about 1.5 mg. The amount of cross-linked polyacrylic acid polymers, e.g., Carbopol®, e.g., Carbopol® 971P, in the oral formulation can be about 14 mg to about 15 mg, e.g., about 14.6 mg.

The pharmaceutical composition can comprise an enteric coat. The enteric coat can comprise, for example, methacrylic acid copolymers. The methacrylic acid copolymers (e.g., Eudragit®) can be, for example, Eudragit RSPO. The amount of methacrylic acid copolymers, e.g., Eudragit® can be, for example, about 5% to about 10% to about 20% or about 15% to about 20% of the pharmaceutical composition by weight. In one instance, the amount of Eudragit® (e.g., Eudragit RSPO) is about 18%. The amount of methacrylic acid copolymers (e.g., Eudragit®) in the oral formulation can be about 60 to about 65 mg, e.g., about 61.1 mg or about 61.2 mg. The amount of methacrylic acid copolymers (e.g., Eudragit®) in the oral formulation can be about 52 to about 53 mg. In some embodiments, Eudragit is added in amount that results in about 12%, e.g., 12.5% weight gain of the pharmaceutical composition.

The pharmaceutical composition can also comprise a filler and/or diluent, e.g., for providing suitable properties to a pharmaceutical powder blend upon manufacturing. Accordingly, the pharmaceutical composition can comprise mannitol. A pharmaceutical composition can comprise, for example, about 1% to about 30% or about 5% to about 30% mannitol of the pharmaceutical composition by weight. A pharmaceutical composition can comprise about 10% to about 20% mannitol of the pharmaceutical composition by weight. A pharmaceutical composition can comprise about 15% to about 30% mannitol of the pharmaceutical composition by weight. A pharmaceutical composition can comprise about 5% to about 20% mannitol of the pharmaceutical composition by weight. A pharmaceutical composition can comprise, for example, about 1 mg to about 150 mg or about 50 mg to about 100 mg mannitol.

For example, in some embodiments, a pharmaceutical composition, e.g., a pharmaceutical composition containing Tris base, comprises about 1% to about 20% mannitol, e.g., about 1% to about 9.35%, about 5% to about 20%, about 9.76% to about 18.39%, about 10% to about 20%, about 10.57% to about 19.30%, about 10.57% to about 19.4%, about 1%, about 9.35%, about 9.76%, about 18.3%, or about 18.39% of the pharmaceutical composition by weight. The amount of mannitol in a pharmaceutical formulation, e.g., a pharmaceutical formulation containing Tris base, can be about 4.9 mg, about 45.7 mg, about 46.82 mg, about 51.8 mg, about 65.1 mg, about 75 mg, about 84.7 mg, about 88.1 mg, about 89.6 mg, about 94.7 mg, about 94.8 mg, about 101.8 mg.

In some embodiments, a pharmaceutical composition, e.g., a pharmaceutical composition not containing Tris base, comprises about 17 to about 30% mannitol, e.g., about 17.98% to about 26.78% of the pharmaceutical composition by weight. The amount of mannitol in a pharmaceutical formulation, e.g., a pharmaceutical formulation not containing Tris base, can be about 87.9 mg, about 125.3 mg, or about 130.9 mg.

The pharmaceutical composition can also contain a disintegrant, e.g., that allows for the tablet to fall apart and adequately contact gastrointestinal fluid in order to be solubilized and systemically absorbed. Accordingly, the pharmaceutical composition can comprise crospovidone (e.g., Kollidon CL). For example, in some embodiments, a pharmaceutical composition, e.g., a pharmaceutical composition containing or lacking Tris base, comprises about 1% to about 10%, about 5% to about 6%, or about 5.81% crospovidone (e.g., Kollidon CL) of the pharmaceutical composition by weight. In some embodiments, a pharmaceutical composition, e.g., a pharmaceutical composition containing or lacking Tris base, comprises about 25 mg to about 35 mg, about 28 mg to about 29 mg, or about 28.4 mg crospovidone (e.g., Kollidon CL).

The pharmaceutical composition can comprise a glidant, e.g., that ensures powder flow during tablet manufacturing. Accordingly, the pharmaceutical composition can comprise fumed silica (e.g., Aerosil 300). For example, in some embodiments, a pharmaceutical composition, e.g., a pharmaceutical composition containing or lacking Tris base, comprises about 0.5% to about 5% or about 1% fumed silica (e.g., Aerosil 300) of the pharmaceutical composition by weight. In some embodiments, a pharmaceutical composition, e.g., a pharmaceutical composition containing or lacking Tris base, comprises about 1 mg to about 10 mg or about 4 mg to about 5 mg, e.g., about 4.9 mg fumed silica (e.g., Aerosil 300).

The pharmaceutical composition can comprise a lubricant, e.g., that prevents blend sticking during tablet manufacturing. Accordingly, the pharmaceutical composition can comprise sodium stearyl fumarate. For example, in some embodiments, a pharmaceutical composition, e.g., a pharmaceutical composition containing or lacking Tris base, comprises about 1% to about 10% or about 5% sodium stearyl fumarate of the pharmaceutical composition by weight. In some embodiments, a pharmaceutical composition, e.g., a pharmaceutical composition containing or lacking Tris base, comprises about 20 mg to about 30 mg or about 24 mg to about 25 mg, e.g., about 24.4 mg sodium stearyl fumarate. In some embodiments, a pharmaceutical composition, e.g., a pharmaceutical composition containing Tris base, comprises about 12 mg to about 13 mg, e.g., about 12.2 mg sodium stearyl fumarate.

An oral formulation, provided herein, can comprise about 0.0625 mg to about 36 mg of a GLP-1 peptide analog (e.g., SEQ ID NO:2 or an ammonium acetate salt thereof (MEDI7219)); about 100 mg to about 800 mg sodium chenodeoxycholate; about 200 mg to about 1600 mg propyl gallate; about 0 mg to about 120 mg Tris base; and/or about 0 mg to about 120 of cross-linked polyacrylic acid polymers (e.g., Carbopol 971P), optionally further comprising a filler (e.g., mannitol), a disintegrant (e.g., crospovidone such as Kollidon CL), a glidant (e.g., fumed silica such as Aerosil 300), and/or a lubricant (e.g., sodium stearyl fumarate). Such an oral formulation can optionally comprise about 60 mg to about 61 mg, e.g., about 61.2 mg of an enteric coating, e.g., a methacrylic acid copolymer coating (e.g., an Eudragit coating).

An oral formulation, e.g., an immediate release oral formulation provided herein, can comprise about 0.1% to about 10% of a GLP-1 peptide analog (e.g., SEQ ID NO:2 or an ammonium acetate salt thereof (MEDI7219)); about 10% to about 30%, sodium chenodeoxycholate; about 15% to about 60% propyl gallate; about 5% to about 20% mannitol, 0% to about 10% Tris base, about 2% to about 10% of a disintegrant (e.g., crospovidone such as Kollidon CL), about 1% to about 5% of a glidant (e.g., fumed silica such as Aerosil 300), and/or about 1% to about 15% of a lubricant (e.g., sodium stearyl fumarate) of the oral formulation by weight. Such an oral formulation can optionally comprise an enteric coating, e.g., a methacrylic acid copolymer coating (e.g., an Eudragit coating) that increase the weight of the formulation by about 10% to about 15%.

An oral formulation, e.g., a controlled release oral formulation provided herein, can comprise about 0.1% to about 10% of a GLP-1 peptide analog (e.g., SEQ ID NO:2 or an ammonium acetate salt thereof (MEDI7219)); about 10% to about 30%, sodium chenodeoxycholate; about 15% to about 60% propyl gallate; about 5% to about 20% mannitol, 0% to about 10% Tris base, about 2% to about 10% of a disintegrant (e.g., crospovidone such as Kollidon CL), about 0.1% to about 15% of cross-linked polyacrylic acid polymers (e.g., Carbopol 971P), about 1% to about 5% of a glidant (e.g., fumed silica such as Aerosil 300), and/or about 1% to about 15% of a lubricant (e.g., sodium stearyl fumarate) of the oral formulation by weight. Such an oral formulation can optionally comprise an enteric coating, e.g., a methacrylic acid copolymer coating (e.g., an Eudragit coating) that increase the weight of the formulation by about 10% to about 15%.

An oral formulation, e.g., an immediate release tablet, provided herein, can comprise about 4.5 mg of a GLP-1 peptide analog (e.g., SEQ ID NO:2 or an ammonium acetate salt thereof (MEDI7219)); about 100 mg sodium chenodeoxycholate; about 200 mg propyl gallate; about 101 mg to about 102 mg, e.g., about 101.8 mg, mannitol; about 36 mg to about 37 mg, e.g., about 36.2 mg Tris base; about 28 mg to about 29 mg, e.g., about 28.4 mg, crospovidone (e.g., Kollidon CL); about 4 mg to about 5 mg, e.g., about 4.9 mg, fumed silica (e.g., Aerosil 300); and/or about 12 mg to about 13 mg, e.g. about 12.2 mg sodium stearyl fumarate. Such an oral formulation can optionally comprise about 60 mg to about 61 mg, e.g., about 61.2 mg of an enteric coating, e.g., a methacrylic acid copolymer coating (e.g., an Eudragit coating).

An oral formulation, e.g., a controlled release tablet, provided herein, can comprise about 4.5 mg of a GLP-1 peptide analog (e.g., SEQ ID NO:2 or an ammonium acetate salt thereof (MEDI7219)); about 100 mg sodium chenodeoxycholate; about 200 mg propyl gallate; about 88 mg to about 89 mg, e.g., about 88.1 mg, mannitol; about 36 mg to about 37 mg, e.g., about 36.2 mg, Tris base; about 1 mg to about 2 mg, e.g., about 1.5 mg (or about 0.3%) of cross-linked polyacrylic acid polymers (e.g., Carbopol 971P); about 28 mg to about 29 mg, e.g., about 28.4 mg, crospovidone (e.g., Kollidon CL); about 4 mg to about 5 mg, e.g., about 4.9 mg, fumed silica (e.g., Aerosil 300); and/or about 24 mg to about 25 mg, e.g. about 24.4 mg, sodium stearyl fumarate. Such an oral formulation can optionally comprise about 60 mg to about 61 mg, e.g., about 61.2 mg of an enteric coating, e.g., a methacrylic acid copolymer coating (e.g., an Eudragit coating).

An oral formulation, e.g., a controlled release tablet, provided herein, can comprise about 4.5 mg of a GLP-1 peptide analog (e.g., SEQ ID NO:2 or an ammonium acetate salt thereof (MEDI7219)); about 100 mg sodium chenodeoxycholate; about 200 mg propyl gallate; about 75 mg, mannitol; about 36 mg to about 37 mg, e.g., about 36.2 mg, Tris base; about 14 mg to about 15 mg, e.g., about 14.6 mg, (or about 3%) of cross-linked polyacrylic acid polymers (e.g., Carbopol 971P); about 28 mg to about 29 mg, e.g., about 28.4 mg, crospovidone (e.g., Kollidon CL); about 4 mg to about 5 mg, e.g., about 4.9 mg, fumed silica (e.g., Aerosil 300); and/or about 12 mg to about 13 mg, e.g. about 12.2 mg, sodium stearyl fumarate. Such an oral formulation can optionally comprise about 60 mg to about 61 mg, e.g., about 61.2 mg of an enteric coating, e.g., a methacrylic acid copolymer coating (e.g., an Eudragit coating).

An oral formulation, e.g., an immediate release tablet, provided herein, can comprise about 1 mg to about 10 mg of a GLP-1 peptide analog (e.g., SEQ ID NO:2 or an ammonium acetate salt thereof (MEDI7219)); about 50 mg to about 150 mg sodium chenodeoxycholate; about 100 mg to about 300 mg propyl gallate; about 50 mg to about 150 mg mannitol; about 15 mg to about 50 mg Tris base; about 10 mg to about 45 mg, crospovidone (e.g., Kollidon CL); about 1 mg to about 10 mg fumed silica (e.g., Aerosil 300); and/or about 5 mg to about 25 mg sodium stearyl fumarate. Such an oral formulation can optionally comprise about 60 mg to about 61 mg, e.g., about 61.2 mg of an enteric coating, e.g., a methacrylic acid copolymer coating (e.g., an Eudragit coating).

An oral formulation, e.g., a controlled release tablet, provided herein, can comprise about 1 mg to about 10 mg of a GLP-1 peptide analog (e.g., SEQ ID NO:2 or an ammonium acetate salt thereof (MEDI7219)); about 50 mg to about 150 mg sodium chenodeoxycholate; about 100 mg to about 300 mg propyl gallate; about 35 mg to about 135 mg mannitol; about 15 mg to about 50 mg Tris base e; about 1 mg to about 2 mg, e.g., about 1.5 mg (or about 0.3%) of cross-linked polyacrylic acid polymers (e.g., Carbopol 971P); about 28 mg to about 29 mg, e.g., about 28.4 mg, crospovidone (e.g., Kollidon CL); about 1 mg to about 10 mg fumed silica (e.g., Aerosil 300); and/or about 10 mg to about 50 mg sodium stearyl fumarate. Such an oral formulation can optionally comprise about 60 mg to about 61 mg, e.g., about 61.2 mg of an enteric coating, e.g., a methacrylic acid copolymer coating (e.g., an Eudragit coating).

An oral formulation, e.g., a controlled release tablet, provided herein, can comprise about 1 mg to about 10 mg of a GLP-1 peptide analog (e.g., SEQ ID NO:2 or an ammonium acetate salt thereof (MEDI7219)); about 50 mg to about 150 mg sodium chenodeoxycholate; about 100 mg to about 300 mg propyl gallate; about 25 mg to about 125 mg mannitol; about 15 mg to about 50 mg Tris base; about 14 mg to about 15 mg, e.g., about 14.6 mg, (or about 3%) of cross-linked polyacrylic acid polymers (e.g., Carbopol 971P); about 28 mg to about 29 mg, e.g., about 28.4 mg, crospovidone (e.g., Kollidon CL); about 1 mg to about 10 mg fumed silica (e.g., Aerosil 300); and/or about 5 mg to about 25 mg sodium stearyl fumarate. Such an oral formulation can optionally comprise about 60 mg to about 61 mg, e.g., about 61.2 mg of an enteric coating, e.g., a methacrylic acid copolymer coating (e.g., an Eudragit coating).

In the oral formulations provided herein, an enteric coating, e.g., a methacrylic acid copolymer coating (e.g., an Eudragit coating) can comprise, for example, about 85% to about 86%, e.g., about 85.5%, of a methacrylic acid copolymer (e.g., Eudragit) and about 14% to about 15%, e.g., about 14.5% of an enteric coating plasticizer (e.g., PlasACRYL) of the oral formulation by weight.

An oral formulation as provided herein can comprise salcaprozate sodium (i.e., sodium N-(8-(2-hydroxybenzoyl)amino)caprylate (SNAC)).

An oral formulation as provided herein can comprise sodium caprate. The formulation can comprise, for example, about 300 mg sodium caprate to about 2400 mg sodium caprate. The formulation can comprise, for example, about 300 mg sodium caprate. The formulation can comprise, for example, about 600 mg sodium caprate. The formulation can comprise, for example, about 900 mg sodium caprate. The formulation can comprise, for example, about 1200 mg sodium caprate. The formulation can comprise, for example, about 2400 mg sodium caprate.

In a formulation comprising sodium caprate provided herein, the ratio of sodium caprate to GLP-1 peptide analog (e.g., SEQ ID NO:2 or an ammonium acetate salt thereof (MEDI7219)) can be, for example, 10:1 to 150:1. The ratio of sodium caprate to GLP-1 peptide analog (e.g., SEQ ID NO:2 or an ammonium acetate salt thereof (MEDI7219)) can be, for example 15:1. The ratio of sodium caprate to GLP-1 peptide analog (e.g., SEQ ID NO:2 or an ammonium acetate salt thereof (MEDI7219)) can be, for example 50:1. The ratio of sodium caprate to GLP-1 peptide analog (e.g., SEQ ID NO:2 or an ammonium acetate salt thereof (MEDI7219)) can be, for example, 150:1.

A formulation provided herein comprising sodium caprate can comprise an enteric coating, e.g., an enteric coating with a pH of 5.5 or with a pH of 7.0. A formulation comprising sodium caprate can comprise cross-linked polyacrylic acid polymers (e.g., Carbopol), e.g., about 0.9% of cross-linked polyacrylic acid polymers (e.g., Carbopol).

As provided herein, the oral formulation can be a solid, a liquid, or a gel (e.g., a lipid gel).

Solid dosage forms include, for example, tablets and capsules. Tablets include, for example, tablets in acid-resistant capsules, enterically-coated tablets, and mini-tablets. Mini-tablets may be enterically coated or uncoated and loaded in enterically coated capsules of acid-resistant capsules. The solid dosage form (e.g., tablet) can be a multi-unit particulate (MUP) formulation.

Liquid dosage forms include, for example, solutions (e.g., a solution in an aqueous media) and suspensions (e.g., a suspension in an oil-based self-emulsified system).

The oral formulations provided herein can be controlled release formulations.

The oral formulations provided herein can comprise an enteric coat. The oral formulations provided herein can comprise polymer layers, e.g., for controlled release or mucoadhesive properties.

As provided herein, the GLP-1 peptide analog (e.g., SEQ ID NO:2 or an ammonium acetate salt thereof (MEDI7219)) administered in the oral formulation provided herein can be absorbed in the proximal colon. The GLP-1 peptide analog (e.g., SEQ ID NO:2 or an ammonium acetate salt thereof (MEDI7219)) administered in the oral formulation provided herein can be absorbed in the proximal small bowel region. The GLP-1 peptide analog (e.g., SEQ ID NO:2 or an ammonium acetate salt thereof (MEDI7219)) administered in the oral formulation provided herein can be absorbed in the proximal colon and the proximal small bowel region.

Such oral formulations provide high bioavailability of the GLP-1 peptide analog (e.g., SEQ ID NO:2 or an ammonium acetate salt thereof (MEDI7219)) and low pharmacokinetic variability. Furthermore, such oral formulations enable optimum solubility of the peptide thereby enabling better absorption. In one aspect of this invention the pharmaceutical excipients identified herein act as a dual agent in maintaining the solubility of the GLP-1 peptide analog (e.g., SEQ ID NO:2 or an ammonium acetate salt thereof (MEDI7219)) as well as disrupting tight junctions and acting as a permeation enhancer.

Pharmaceutical compositions for oral administration provided herein can comprise excipients that provide optimum solubility of a GLP-1 peptide analog (e.g., SEQ ID NO:2 or an ammonium acetate salt thereof (MEDI7219)) and permeation enhancing action to improve bioavailability and decrease variability. In some embodiments, the GLP-1 peptide analog (e.g., SEQ ID NO:2 or an ammonium acetate salt thereof (MEDI7219)) is released from the pharmaceutical composition after the permeation enhancer(s) is released from the pharmaceutical formulation. Such a sequential release can improve the bioavailability and reduce the variability of the GLP-1 peptide analog (e.g., SEQ ID NO:2 or an ammonium acetate salt thereof (MEDI7219)).

In certain embodiments, a pharmaceutical composition for oral administration provided herein can be about 2 grams or less. In certain embodiments, a pharmaceutical composition for oral administration provided herein can be about 1.9 grams or less, about 1.8 grams or less, about 1.7 grams or less, about 1.6 grams or less, about 1.5 grams or less, about 1.4 grams or less, about 1.3 grams or less, about 1.2 grams or less, 1 about 1.1 grams or less, about 1 gram or less, about 0.9 grams or less, about 0.8 grams or less, about 0.7 grams or less, about 0.6 grams or less, or about 0.5 grams or less.

In certain embodiments, a pharmaceutical composition for oral administration provided herein can be about 400 mg to about 500 mg. In certain embodiments, a pharmaceutical composition for oral administration provided herein can be about 450 mg to about 500 mg. In certain embodiments, a pharmaceutical composition for oral administration provided herein can be about 475 mg to about 500 mg.

In certain embodiments, a pharmaceutical composition for oral administration provided herein can be about 2 grams. In certain embodiments, a pharmaceutical composition for oral administration provided herein can be about 1.5 grams. In certain embodiments, a pharmaceutical composition for oral administration provided herein can be about 1 gram. In certain embodiments, a pharmaceutical composition for oral administration provided herein can be about 0.5 grams.

In certain embodiments, a pharmaceutical composition for oral administration provided herein can be about 488 milligrams.

VI. Methods of Treatment by Orally Administering GLP-1 Peptide Analogs

Methods of orally administering GLP-1 peptide analogs are provided herein.

For example, provided herein are methods of treating a subject comprising administering a GLP-1 peptide analog (e.g., SEQ ID NO:2 or an ammonium acetate salt thereof (MEDI7219)) in an oral formulation provided herein to a subject in need thereof.

As provided herein, oral administration of GLP-1 peptide analogs (e.g., SEQ ID NO:2 or an ammonium acetate salt thereof (MEDI7219)) can be used to treat or prevent a disease or condition caused or characterized by hyperglycemia or impaired insulin release.

In certain embodiments, the methods herein comprise treating diabetes by orally administering a GLP-1 peptide analog (e.g., SEQ ID NO:2 or an ammonium acetate salt thereof (MEDI7219)) to a subject in need thereof.

In certain embodiments, the methods herein comprise treating type-2 diabetes by orally administering a GLP-1 peptide analog (e.g., SEQ ID NO:2 or an ammonium acetate salt thereof (MEDI7219)) to a subject in need thereof.

In certain embodiments, oral administration of GLP-1 peptide analogs (e.g., SEQ ID NO:2 or an ammonium acetate salt thereof (MEDI7219)) improves glycemic control, provides body weight control, improves (3-cell function and/or mass, reduces the rate of gastric acid secretion and gastric emptying, or any combination thereof.

In certain embodiments, a GLP-1 peptide analog (e.g., SEQ ID NO:2 or an ammonium acetate salt thereof (MEDI7219)) can inhibit gastric motility and/or promote insulin release. A GLP-1 peptide analog (e.g., SEQ ID NO:2 or an ammonium acetate salt thereof (MEDI7219)) can therefore act to accelerate elimination of excessive adipose tissue, induce sustainable weight loss, and improve glycemic control.

In certain embodiments, the methods herein comprise treating obesity by orally administering a GLP-1 peptide analog (e.g., SEQ ID NO:2 or an ammonium acetate salt thereof (MEDI7219)) to a subject in need thereof. In certain embodiments, the subject has type 2 diabetes mellitus.

In certain embodiments, the methods herein comprise reducing body weight by orally administering a GLP-1 peptide analog (e.g., SEQ ID NO:2 or an ammonium acetate salt thereof (MEDI7219)) to a subject in need thereof. In certain embodiments, the subject has type 2 diabetes mellitus.

In certain embodiments, the methods herein comprise reducing body fat by orally administering a GLP-1 peptide analog (e.g., SEQ ID NO:2 or an ammonium acetate salt thereof (MEDI7219)) to a subject in need thereof. In certain embodiments, the fat is liver fat. The reduction of liver fat can lead to enhanced insulin sensitivity and/or improved liver function.

In certain embodiments, the methods herein comprise managing weight by orally administering a GLP-1 peptide analog (e.g., SEQ ID NO:2 or an ammonium acetate salt thereof (MEDI7219)) to a subject in need thereof.

In certain embodiments, the methods herein comprise preventing weight gain, preventing fat gain (e.g., liver fat), promoting weight loss, promoting fat loss (e.g., liver fat), reducing excess body weight, reducing fat (e.g., liver fat), or treating obesity (e.g. by control of appetite, feeding, food intake, and/or calorie intake), including morbid obesity by orally administering a GLP-1 peptide analog (e.g., SEQ ID NO:2 or an ammonium acetate salt thereof (MEDI7219)) to a subject in need thereof. In certain embodiments, the methods herein comprise treating or preventing a disease or condition caused or characterized by excess body weight or excess body fat by orally administering a GLP-1 peptide analog (e.g., SEQ ID NO:2 or an ammonium acetate salt thereof (MEDI7219)) to a subject in need thereof.

In certain embodiments, the oral administration is an adjunct to diet and exercise. The administration can also reduce body weight or treat obesity. In certain embodiments, the subject has a BMI of 27 to 40 kg/m$^2$. In certain embodiments, the subject has a BMI of 30 to 39.9 kg/m$^2$. In certain embodiments, the subject has a BMI of at least 40. In certain embodiments, the subject is overweight. In certain embodiments, the subject is obese.

Subjects that can be orally administered the GLP-1 peptide analog (e.g., SEQ ID NO:2 or an ammonium acetate salt thereof (MEDI7219)) in the various methods described herein include mammals, for example, humans, dogs, cats, primates, cattle, sheep, horses, pigs, etc. Thus, in some embodiments, the subject is a human.

The GLP-1 peptide analog (e.g., SEQ ID NO:2 or an ammonium acetate salt thereof (MEDI7219)) can be orally administered as soon as possible after a suitable diagnosis, e.g., within hours or days. In certain embodiments, the pharmaceutical formulation is administered orally once per day. In certain embodiments, the pharmaceutical formulation is administered orally twice per day.

Exemplary Pharmaceutical Compositions and Methods

Pharmaceutical compositions for oral administration are provided herein.

In one instance (I1), a pharmaceutical composition for oral administration comprises (i) a bislipidated GLP-1 peptide analog and (ii) sodium chenodeoxycholate.

In one instance (I2), a pharmaceutical composition for oral administration comprising (i) a bislipidated GLP-1 peptide analog and (ii) propyl gallate.

In one instance (I3) of I2, the pharmaceutical composition further comprises sodium chenodeoxycholate.

In one instance (I4) of I3, the ratio of sodium chenodeoxycholate to propyl gallate is 150:1 to 1:4. In one instance (I5) of I4, the ratio of sodium chenodeoxycholate to propyl gallate is 145:1. In one instance (I6) of I4, the ratio of sodium chenodeoxycholate to propyl gallate is 29:1. In one instance (I7) of I4, the ratio of sodium chenodeoxycholate to propyl gallate is 14:1. In one instance (I8) of I4, the ratio of sodium chenodeoxycholate to propyl gallate is 6.5:1. In one instance (I9) of I4, the ratio of sodium chenodeoxycholate to propyl gallate is 4:1. In one instance (I10) of I4, the ratio of sodium chenodeoxycholate to propyl gallate is 2:1. In one instance (I11) of I4, the ratio of sodium chenodeoxycholate to propyl gallate is 1:1. In one instance (I12) of I3, the ratio of sodium chenodeoxycholate to propyl gallate is 2:1 to 1:4. In one instance (I13) of I12, the ratio of sodium chenodeoxycholate to propyl gallate is 1:2.

In one instance (I14) of any one of I1 and I3-I13, the amount of sodium chenodeoxycholate is about 1 mg to about 1500 mg. In one instance (I15) of I14, the amount of sodium chenodeoxycholate is about 100 mg to about 800 mg. In one instance (I16) of I14, the amount of sodium chenodeoxycholate is about 100 mg, about 200 mg, about 300 mg, about 400 mg, about 500 mg, about 600 mg, about 700 mg, or about 800 mg. In one instance (I17) of I14, the amount of sodium chenodeoxycholate is about 50 mg, about 65 mg, about 120 mg, about 130 mg, about 140 mg, about 150 mg, about 260 mg, about 280 mg, about 290 mg, or about 299 mg. In one instance (I18) of I14, the amount of sodium chenodeoxycholate is about 100 mg.

In one instance (I19) of any one of I1 and I3-I13, sodium chenodeoxycholate is about 15% to about 25% of the pharmaceutical composition by weight. In one instance (I20) of I19, sodium chenodeoxycholate is about 20% to about 21% of the pharmaceutical composition by weight.

In one instance (I21) of any one of I1 and I3-I13, sodium chenodeoxycholate is about 15% to about 65% of the pharmaceutical composition by weight, optionally wherein sodium chenodeoxycholate is about 30% to about 65% of the pharmaceutical composition by weight.

In one instance (I22) of any one of I2-I21, the amount of propyl gallate is about 1 mg to about 3000 mg. In one instance (I23) of I22, the amount of propyl gallate is about 200 mg to about 1600 mg. In one instance (I24) of I22, the amount of propyl gallate is about 2 mg, about 10 mg, about 20 mg, about 30 mg, about 40 mg, about 50 mg, about 100 mg, about 150 mg, or about 200 mg. In one instance (I25) of I22, the amount of propyl gallate is about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, or about 1600 mg. In one instance (I26) of I22, the amount of propyl gallate is about 200 mg.

In one instance (I27) of any one of I2-I21, propyl gallate is about 45% to about 55% of the pharmaceutical composition by weight. In one instance (I28) of I27, propyl gallate is about 40% to about 41% of the pharmaceutical composition by weight.

In one instance (I29) of any one of I1 and I41-I21, the pharmaceutical composition does not comprise propyl gallate.

In one instance (I30) of any one of I1-I29, the pharmaceutical composition further comprises a pH modifier.

In one instance (I31) of any one of I1-I30, the pharmaceutical composition further comprises Tris base. In one instance (I32) of I31, the amount of Tris base is up to 300 mg. In one instance (I33) of I32, the amount of Tris base is about 30 mg to about 40 mg. In one instance (I34) of I32, the amount of Tris base is about 36 mg to about 37 mg. In one instance (I35) of I31, Tris base is about 5% to about 10% of the pharmaceutical composition by weight. In one instance (I36) of I31, Tris base is about 7% to about 8% of the pharmaceutical composition by weight.

In one instance (I37) of any one of I1-I29, the pharmaceutical composition does not comprise a pH modifier. In one instance (I38) of any one of I1-I29, the pharmaceutical composition does not comprise Tris base.

In one instance (I39) of any one of I1-I38, the pharmaceutical composition comprises an enteric coating that dissolves at a pH of about 5 to about 7.5. In one instance (I40) of any one of I1-I38, the pharmaceutical composition comprises an enteric coating that dissolves at a pH of about 5.5 or above. In one instance (I41) of any one of I1-I38, the pharmaceutical composition comprises an enteric coating that dissolves at a pH of about 7.0 or above.

In one instance (I42) of any one of I1-I41, the pharmaceutical composition further comprises a bioadhesive. In one instance (I43) of any one of I1-I41, the pharmaceutical composition further comprises cross-linked polyacrylic polymers. In one instance (I44) of I43, the cross-linked polyacrylic polymers are in a powder form or a granular from. In one instance (I45) of any one of I1-I41, the pharmaceutical composition further comprises Carbopol®. In one instance (I46) of any one of I42-I45, the amount of bioadhesive or cross-linked polyacrylic polymers or Carbopol® is about 1 mg to about 50 mg. In one instance (I47) of any one of I42-I45, the amount of bioadhesive or cross-linked polyacrylic polymers or Carbopol® is about 1 mg to about 2 mg. In one instance (I48) of any one of I42-I45, the amount of bioadhesive or cross-linked polyacrylic polymers or Carbopol® is about 4 mg to about 5 mg. In one instance (I49) of any one of I42-I45, the amount of bioadhesive or cross-linked polyacrylic polymers or Carbopol® is about 14 mg to about 15 mg. In one instance (I50) of any one of I42-I45, the amount of bioadhesive or cross-linked polyacrylic polymers or Carbopol® is about 48 mg to about 49 mg. In one instance (I51) of any one of I42-I45, the bioadhesive or cross-linked polyacrylic polymers or Carbopol® is about 0.3% to about 10% of the pharmaceutical composition by weight. In one instance (I52) of I51, the bioadhesive or cross-linked polyacrylic polymers or Carbopol® is about 0.3% to about 3% of the pharmaceutical composition by weight or about 1% to about 10% of the pharmaceutical composition by weight. In one instance (I53) of I51, the bioadhesive or cross-linked polyacrylic polymers or Carbopol® is about 0.3%, about 1%, about 3%, or about 10% of the pharmaceutical composition by weight. In one instance (I54) of I51, the bioadhesive or cross-linked polyacrylic polymers or Carbopol® is about 0.3%, about 0.9%, or about 1.2% of the pharmaceutical composition by weight.

In one instance (I55) of I45, the Carbopol® is Carbopol® 71G. In one instance (I56) of 155, the amount of Carbopol®

71G is about 4 mg to about 5 mg. In one instance (I57) of 155, the amount of Carbopol® 71G is about 48 mg to about 49 mg. In one instance (I58) of 155, Carbopol® 71G is about 1% to about 10% of the pharmaceutical composition by weight.

In one instance (I59) of I45, the Carbopol® is Carbopol® 971P. In one instance (I60) of 159, the amount of Carbopol® 971P is about 1 mg to about 2 mg. In one instance (I61) of 159, the amount of Carbopol® 971P is about 14 mg to about 15 mg. In one instance (I62) of 159, Carbopol® 971P is about 0.3% to about 3% of the pharmaceutical composition by weight.

In one instance (I63) of any one of I1-I41, the pharmaceutical composition does not comprise a bioadhesive. In one instance (I64) of any one of I1-I41, the pharmaceutical composition does not comprise cross-linked polyacrylic polymers.

In one instance (I65) of any one of I1-I64, the pharmaceutical composition further comprises an enteric coat. In one instance (I66) of any one of I1-I64, the pharmaceutical composition further comprises methacrylic acid copolymers. In one instance (I67) of any one of I1-I64, the pharmaceutical composition, further comprising Eudragit®. In one instance (I68) of any one of I65-I67, the amount of enteric coat or methacrylic acid copolymers or Eudragit® is about 10 mg to about 65 mg. In one instance (I69) of any one of I65-I67, the amount of enteric coat or methacrylic acid copolymers or Eudragit® is about 61 mg to about 62 mg. In one instance (I70) of any one of I65-I67, the amount of enteric coat or methacrylic acid copolymers or Eudragit® is about 10 mg to about 53 mg. In one instance (I71) of any one of I65-I67, the enteric coat or methacrylic acid copolymers or Eudragit® is about 5% to about 15% of the pharmaceutical composition by weight. In one instance (I72) of any one of I65-I67, the enteric coat or methacrylic acid copolymers or Eudragit® dissolves at pH 5.5 or above.

In one instance (I73) of any one of I1-I72, the pharmaceutical composition further comprises a filler. In one instance (I74) of any one of I1-I72, the pharmaceutical composition further comprises a diluent. In one instance (I75) of any one of I1-I72, the pharmaceutical composition further comprises mannitol. In one instance (I76) of any one of I73-I75, the amount of the filler, diluent, or mannitol is about 1 mg to about 150 mg. In one instance (I77) of I76, the amount of the filler, diluent, or mannitol is about 50 mg to about 100 mg. In one instance (I78) of I76, the amount of the filler, diluent, or mannitol is about 75 mg to about 150 mg. In one instance (I79) of any one of I73-I75, the filler, diluent, or mannitol is about 5% to about 30% of the pharmaceutical composition by weight. In one instance (I80) of I79, the filler, diluent, or mannitol is about 5% to about 20% of the pharmaceutical composition by weight. In one instance (I81) of I79, the filler, diluent, or mannitol is about 10% to about 20% of the pharmaceutical composition by weight. In one instance (I82) of I79, the filler, diluent, or mannitol is about 15% to about 30% of the pharmaceutical composition by weight.

In one instance (I83) of any one of I1-I82, the pharmaceutical composition further comprises a disintegrant. In one instance (I84) of any one of I1-I82, the pharmaceutical composition further comprises crospovidone. In one instance (I85) of I83 or I84, the amount of disintegrant or crospovidone is about 25 mg to about 35 mg. In one instance (I86) of I85, the amount of disintegrant or crospovidone is about 28 mg to about 29 mg. In one instance (I87) of I83 or I84, the disintegrant or crospovidone is about 1% to about 10% of the pharmaceutical composition by weight. In one instance (I88) of I87, the disintegrant or crospovidone is about 5% to about 6% of the pharmaceutical composition by weight.

In one instance (I89) of any one of I1-I88, the pharmaceutical composition further comprises a glidant. In one instance (I90) of any one of I1-I88, the pharmaceutical composition further comprises fumed silica. In one instance (I91) of I89 or I90, the amount of glidant or fumed silica is about 1 mg to about 10 mg. In one instance (I92) of I91, the amount of glidant or fumed silica is about 4 mg to about 5 mg. In one instance (I93) of I89 or I90, the glidant or fumed silica is about 1% of the pharmaceutical composition by weight.

In one instance (I94) of any one of I1-I93, the pharmaceutical composition further comprises a lubricant. In one instance (I95) of any one of I1-I93, the pharmaceutical composition further comprises sodium stearyl fumarate. In one instance (I96) of I94 or I95, the amount of lubricant or sodium stearyl fumarate is about 20 mg to about 30 mg. In one instance (I97) of I96, the amount of lubricant or sodium stearyl fumarate is about 24 mg to about 25 mg. In one instance (I98) of I94 or I95, the lubricant or sodium stearyl fumarate is about 5% of the pharmaceutical composition by weight.

In one instance (I99) of any one of I1-I98, further comprising sodium caprate.

In one instance (I100), a pharmaceutical composition for oral administration comprises a bislipidated GLP-1 peptide analog and sodium N-(8-(2-hydroxybenzoyl)amino)caprylate (SNAC).

In one instance (I101), a pharmaceutical composition for oral administration comprises a bislipidated GLP-1 peptide analog and sodium caprate. In one instance (I102) of I101, the composition comprises about 300 mg to about 2400 mg sodium caprate. In one instance (I103) of I102, the composition comprises about 300 mg sodium caprate. In one instance (I104), of I102, the composition comprises about 600 mg sodium caprate. In one instance (I105) of I102, the composition comprises about 900 mg sodium caprate. In one instance (I106) of I102, the composition comprises about 1200 mg sodium caprate. In one instance (I107) of I102, the composition comprises about 2400 mg sodium caprate.

In one instance (I108) of any one of I1-I107, the amount of the GLP-1 peptide analog is about 0.1 mg to about 100 mg. In one instance (I109) of any one of I1-I107, the amount of the GLP-1 peptide analog is about 0.0625 mg to about 36 mg. In one instance (I110) of any one of I1-I107, the amount of the GLP-1 peptide analog is about 0.25 mg to about 36 mg. In one instance (I111), the amount of the GLP-1 peptide analog is about 0.125 mg, about 4.5 mg, or about 36 mg. In one instance (I112) of any one of I1-I107, the GLP-1 peptide analog is about 0.2% to about 10% of the pharmaceutical composition by weight.

In one instance (I113), a pharmaceutical composition for oral administration comprises (i) about 0.1 mg to about 100 mg of a bislipidated GLP-1 peptide analog (ii) about 1 mg to about 1500 mg sodium chenodeoxycholate, (iii) about 1 mg to about 3000 mg propyl gallate, and (iv) 0 to about 300 mg Tris base. In one instance (I114) of I113, the pharmaceutical composition further comprising a filler, disintegrant, glidant, lubricant, bioadhesive and/or enteric coat. In one instance (I115) of I113, the pharmaceutical composition further comprises mannitol, crospovidone, fumed silica, sodium stearyl fumarate, cross-linked polyacrylic acid polymers, and/or methacrylic acid copolymers.

In one instance (I116), a pharmaceutical composition for oral administration comprises (i) about 0.1% to about 10% of a bislipidated GLP-1 peptide analog (ii) about 10% to about 30% sodium chenodeoxycholate, and (iii) about 20% to about 60% propyl gallate.

In one instance (I117), a pharmaceutical composition for oral administration comprises (i) about 0.1% to about 10% of a bislipidated GLP-1 peptide analog (ii) about 15% to about 25% sodium chenodeoxycholate, and (iii) about 30% to about 50% propyl gallate. In one instance (I118) of I116 or I117, the pharmaceutical composition further comprises (iv) about 5% to about 20% mannitol, (v) 0 to about 10% Tris base; (vi) about 2% to about 10% crospovidone, (vii) about 0.5% to about 5% fumed silica, and/or (viii) about 1% to about 15% sodium stearyl fumarate.

In one instance (I119) of any one of I116-I118, the pharmaceutical composition comprises about 3% to about 10% crospovidone. In one instance (I120) of any one of I116-I119, the pharmaceutical composition comprises about 1% to about 5% fumed silica.

In one instance (I121), a pharmaceutical composition for oral administration comprises (i) about 0.256% to about 7.364% of a bislipidated GLP-1 peptide analog (ii) about 20.5% sodium chenodeoxycholate, (iii) about 40.9% propyl gallate, (iv) about 6.833% to about 18.903% mannitol, (v) 0 to about 7.815% Tris base; (vi) about 5.81% crospovidone, (vii) about 1% fumed silica, and (viii) about 2% to about 10% sodium stearyl fumarate.

In one instance (I122), a pharmaceutical composition for oral administration comprises (i) about 0.256% to about 7.364% of a bislipidated GLP-1 peptide analog (ii) about 20.5% sodium chenodeoxycholate, (iii) about 40.9% propyl gallate, (iv) about 6.833% to about 18.903% mannitol, (v) 0 to about 7.815% Tris base; (vi) about 5.81% crospovidone, (vii) about 0.3% to about 10% cross-linked polyacrylic acid polymers, (viii) about 1% fumed silica, and (ix) about 2% to about 10% sodium stearyl fumarate.

In one instance (I123), a pharmaceutical composition for oral administration comprises (i) about 0.1 mg to about 40 mg of a bislipidated GLP-1 peptide analog; (ii) about 75 mg to about 125 mg of sodium chenodeoxycholate, and (iii) about 150 mg to about 250 mg propyl gallate. In one instance (I124) of I123, the pharmaceutical composition further comprises (iv) about 40 mg to about 125 mg mannitol, (v) 0 to about 45 mg Tris base, (vi) about 25 mg to about 35 mg crospovidone, (vii) about 1 mg to about 10 mg fumed silica, and (viii) about 20 mg to about 30 mg sodium stearyl fumarate.

In one instance (I125), a pharmaceutical composition for oral administration comprises (i) about 1.25 mg, about 4.5 mg, or about 36 mg of a bislipidated GLP-1 peptide analog; (ii) about 100 mg of sodium chenodeoxycholate, (iii) about 200 mg propyl gallate, (iv) about 94.7 mg, about 89.6 mg, or about 51.8 mg mannitol, (v) 0 to about 36.2 mg Tris base, (vi) about 28.4 mg crospovidone, (vii) about 4.9 mg fumed silica, and (viii) about 24.4 mg sodium stearyl fumarate.

In one instance (I126), a pharmaceutical composition for oral administration comprises (i) about 1 mg to about 10 mg of a bislipidated GLP-1 peptide analog; (ii) about 50 mg to about 150 mg of sodium chenodeoxycholate, and (iii) about 100 mg to about 300 mg propyl gallate. In one instance (I127) of I126 further comprises (iv) about 50 mg to about 150 mg mannitol, (v) 0 to about 50 mg Tris base (vi) about 10 mg to about 45 mg crospovidone, (vii) about 1 mg to about 10 mg fumed silica, and (viii) about 5 mg to about 25 mg sodium stearyl fumarate.

In one instance (I128), a pharmaceutical composition for oral administration comprises (i) about 4.5 mg of a bislipidated GLP-1 peptide analog; (ii) about 100 mg of sodium chenodeoxycholate, (iii) about 200 mg propyl gallate, (iv) about 101.8 mg to about 138 mg, about 88.1 mg to about 124.3 mg, or about 75 mg or 11.2 mg mannitol, (v) 0 to about 36.2 mg Tris base, (vi) 0 mg, about 1.5 mg, or about 14.6 mg cross-linked polyacrylic acid polymers, (vii) about 28.4 mg crospovidone, (viii) about 4.9 mg fumed silica, and (ix) about 12.2 mg or 24.4 mg sodium stearyl fumarate.

In one instance (I129), a pharmaceutical composition for oral administration comprises (i) about 1 to about 15 mg of a bislipidated GLP-1 peptide analog; (ii) about 100 mg to about 800 mg of sodium chenodeoxycholate, and (iii) about 200 mg to about 1600 mg propyl gallate. In one instance (I130) of I129, the pharmaceutical composition comprises about 300 mg to about 400 mg of sodium chenodeoxycholate and about 600 mg to about 800 mg propyl gallate. In one instance (I131) of I129 or I130, the pharmaceutical composition further comprises mannitol, Tris, fumed silica, and/or sodium stearyl fumarate. In one instance (I132) of any one of I129-I131, the pharmaceutical composition further comprises about 50 mg to about 150 mg mannitol, 0 to about 50 mg Tris base about 10 mg to about 45 mg crospovidone, about 1 mg to about 10 mg fumed silica, and/or about 5 mg to about 25 mg sodium stearyl fumarate. In one instance (I133) of any one of I129-I132, the pharmaceutical composition further comprises cross-linked polyacrylic acid polymers.

In one instance (I134) of any one of I116-I133, the pharmaceutical composition comprises an enteric coat. In one instance (I135) of I134, the enteric coat comprises methacrylic acid copolymers.

In one instance (I136) of any one of I113-I135, the ratio of sodium chenodeoxycholate to propyl gallate is about 1:2. In one instance (I137) of any one of I113-I136, the pharmaceutical composition comprises Tris base. In one instance (I138) of any one of I113-I136, the pharmaceutical composition does not comprise Tris base.

In one instance (I139) of any one of I1-I138, the GLP-1 peptide analog comprises any one of SEQ ID NOs: 2-10 or 12-15 or a salt thereof. In one instance (I140) of I139, the GLP-1 peptide analog comprises SEQ ID NO:2 or a salt thereof. In one instance (I141) of I140, the GLP-1 peptide comprises SEQ ID NO:2 and an ammonium acetate salt thereof. In one instance (I142) of I140, the GLP-1 peptide comprises an ammonium acetate salt of SEQ ID NO:2.

In one instance (I143) of any one of I1-I142, the pharmaceutical composition is a solid dosage form. In one instance (I144) of any one of I1-I142, the pharmaceutical composition is in the form of a tablet, a hard capsule, or a soft capsule.

In one instance (I145) of any one of I1-I144, the pharmaceutical composition is an immediate release, enterically coated, sustained release, or delayed release composition.

In one instance (I146) of any one of I1-I145, the GLP-1 peptide analog is absorbed in the proximal colon. In one instance (I147) of any one of I1-I146, the GLP-1 peptide analog is absorbed in the proximal small bowel region. In one instance (I148) of any one of I1-I147, the GLP-1 peptide analog is absorbed in the proximal colon and the proximal small bowel region.

In one instance (I149) of any one of I1-I148, administration of the pharmaceutical composition to a human results in a bioavailability of about 0.5% to about 35%. In one instance (I150) of any one of I1-I149, administration of the pharmaceutical composition results in a pK variability that does not exceed 100% or above, 50% or above 25% or above and that is decreasing upon repeated daily dosing.

In one instance (I151) of any one of I1-I150, the pharmaceutical composition has a disintegration time of about 5 minutes to about 100 minutes in disintegration test assay. In one instance (I152) of any one of I1-I151, the pharmaceutical composition has a dissolution time of about 10 minutes to about 500 minutes in dissolution test assay.

In one instance (I153) of any one of I1-I152, the pharmaceutical composition is less than 2 grams, less than 1.5 grams, less than 1.0 grams, or less than 0.5 grams. In one instance (I155) of any one of I1-I152, the pharmaceutical composition is about 400 mg to about 500 mg.

Also provided herein are methods.

In one instance (I155), a method of improving glycemic control comprises administering the pharmaceutical composition of any one of I1-I154 to a subject in need thereof. In one instance (I156), a method of treating or preventing a disease or condition caused or characterized by hyperglycemia or impaired insulin release, comprises administering the pharmaceutical composition of any one of I1-I154 to a subject in need thereof. In one instance (I157), a method of treating or preventing diabetes, comprises administering the pharmaceutical composition of any one of I1-I154 to a subject in need thereof. In one instance (I158) of I157, the diabetes is type-2 diabetes.

In one instance (I159), a method of reducing body weight comprises administering the pharmaceutical composition of any one of I1-I154 to a subject in need thereof. In one instance (I160), a method of reducing body fat comprises administering the pharmaceutical composition of any one of I1-I154 to a subject in need thereof. In one instance (I161), a method of treating obesity comprises administering the pharmaceutical composition of any one of I1-I154 to a subject in need thereof. In one instance (I162), a method of treating or preventing a disease or condition caused or characterized by excess body weight comprises administering the pharmaceutical composition of any one of I1-I154 to a subject in need thereof. In one instance (I163), a method of managing weight comprises administering the pharmaceutical composition of any one of I1-I154 to a subject in need thereof. In one instance (I164), a method of increasing lipid oxidation comprises administering the pharmaceutical composition of any one I1-I154 to a subject in need thereof. In one instance (I165) of any one of I156 and I159-I164, the subject has diabetes. In one instance (I166) of I165, the diabetes is type 2 diabetes mellitus. In one instance (I167) of any one of I156-I166, the subject's appetite is reduced. In one instance (I168) of any one of I156-I167, the pharmaceutical composition is administered once per day. In one instance (I169) of any one of I156-I168, the subject is human.

In one instance (I170), a method of making the pharmaceutical composition of any one of I3-I28, I30-I99, and I108-I156 comprises combining the GLP-1 peptide analog, the sodium chenodeoxycholate, and the propyl gallate into an oral pharmaceutical composition.

It will be readily apparent to one of ordinary skill in the relevant arts that other suitable modifications and adaptations to the methods and applications described herein can be made without departing from the scope of any of the embodiments. The following examples are included herewith for purposes of illustration only and are not intended to be limiting.

EXAMPLES

Materials and Methods

The following materials and methods were used for quantitative measurements of GLP-1 peptide analogs in plasma (e.g., rat or dog plasma) in the Examples below. These methods used a SCIEX 6600 TripleTOF mass spectrometer coupled with a Shimadzu ultra-high performance liquid chromatography (UHPLC). The specificity of the method was ensured by the retention time, the selected mass for Single-Reaction-Monitoring (SRM) mode, and the selected fragment mass in MS/MS ($MS^2$) mode. MEDI7219 (SEQ ID NO:2) and variants thereof have a complicated fragmentation pattern. There are over 20 fragment ions with similar signal intensity. However, the ability to collect all fragment ions with Triple time-of-flight (TOF) and sum multiple high resolution fragment ions significantly enhanced assay sensitivity. The analytes of interest were analyzed from plasma, a complex biological matrix. Although protein precipitation using organic solvent can reduce matrix interference, significant background still persists. The high mass accuracy offered by the TripleTOF mass spectrometers further eliminated background noise, thus enhancing signal: noise (S/N) and allowing improved quantification.

The following reagents and materials were used to extract GLP-1 agonist plasma:
Water (HPLC grade)
Acetonitrile (HPLC grade)
Formic Acid (HPLC grade)
Methanol (HPLC grade)
GLP-1 agonist peptide (SEQ ID NO:3, MEDI7219 (SEQ ID NO:2), etc.)
Eppendorf protein lo-bind Tubes
Eppendorf Protein lo-bind 96 well plate (1 mL)
Pooled Plasma (species depends on study, rat and dog plasma tested)
Analytical Column: Waters BEH C18 100 mm 2.1 mm 1.7 µm column
Precipitation Solution Acetonitrile:Water=3:1 (v/v)
Reconstitution solution:Acetonitrile:Water=1:4 (v/v)
The plasma extraction procedure used the following steps:
Samples, standards, and quality controls were incubated until they reached room temperature. They were then incubated at 60° C. for 2 minutes and cooled down to room temperature, vortexed, and spun down.
70 µL of samples, standards, or quality controls were transferred into a 1 mL 96-well plate.
In each well, 420 uL of Precipitation Solution was added. The plate was sealed and shook for 10 minutes on a plate shaker at 600 rpm.
The plate was centrifuged at 18G, 2500 RFC, 20° C. for 10 minutes.
The plate was carefully removed, and the upper clear supernatant was extracted with a 200 uL multichannel pipette into a new 96-well protein lobind plate. The supernatant was extracted twice for each well, and the supernatants were combined.
The Plate was placed in TurboVap and the extracted supernatant was dried completely with heated (65° C.) Nitrogen gas at 60 Fahrenheit (Fh).
After the plate was completely dry, the plates were covered and incubated at room temperature for at least 30 minutes until the plate returned back to ambient temperature.
150 µL of Reconstitution solution was added to each well. The plate was covered with a pierceable place seal and shaken at 600 rpm for 10 minutes.
The samples were submitted to the LC-MS/MS on the same day of Preparation
Liquid chromatography (LC) was performed using the following steps:

Mobile phase A: 0.2% (v/v) Formic Acid in Water
Mobile phase B: 0.2% (v/v) Formic Acid in Acetonitrile
Wash solution:Methanol:Acetonitrile:Water=5:4:1 (v/v/v)
Additional LC parameters are summarized in the following Table:
Liquid Chromatography Conditions Employed

| | |
|---|---|
| Analytical Column | Waters BEH C18 100 mm |
| Column Temperature | 60° C. |
| Flow Rate | 0.7 mL/min |
| Typical starting Pressure | 9700 psi |
| Autosampler Temperature | 20° C. |
| Injection volume (Loop size) | 40 µL (50 µL) |

Data acquisition on the high resolution SCIEX 6600 instrument was performed as follows:
  The samples were injected and separated with reversed phase chromatography as described above before been ionized and analyzed with a TripleTOF mass spectrometer.
  The data file for each sample included two experiments. Experiment 1 was a TOF full scan (m/z 400-1900), and experiment 2 was a product ion scan of the target compound.
  Unlike traditional MRM experiments where only one of the product ions from the target analyte is monitored, in TripleTOF instruments, the entire MS/MS spectrum is monitored and recorded.
  Precursor and fragmentation ions for each GLP-1 peptide analog are tabulated below in the following table:
Precursor and Fragment Ion Mass for GLP-1 Peptide Analogs

| | | | Peptide Name | | |
|---|---|---|---|---|---|
| SEQ ID NO: 5 | SEQ ID NO: 6 | Semaglutide | SEQ ID NO: 9 | MEDI7219 (SEQ ID NO: 2) | SEQ ID NO: 3 |
| | | | Ion analyzed | | |
| [M + 4H] + 4 | [M + 4H] + 4 | [M + 4H] + 4 | [M + 4H] + 4 | [M + 4H] + 4 | [M + 3H] + 3 |
| Precursor Ion Mass | | | | | |
| 1100.6 | 1085.1 | 1029.1 | 1097.8 | 1088.8 | 1310.6 |
| Fragment 1 500.3336 | 500.3336 | 657.4155 | 500.3336 | 500.3336 | 472.3242 |
| Fragment 2 685.4388 | 685.4388 | 758.3468 | 685.4388 | 685.4388 | 633.4083 |
| Fragment 3 960.4058 | 897.1321 | 960.4058 | 960.4058 | 459.2562 | 704.4454 |
| Fragment 4 1059.4742 | 1059.4742 | 1059.4742 | 1059.4742 | 897.1321 | 817.5294 |
| Fragment 5 1440.7237 | 1160.5218 | 1146.5062 | 1160.5218 | 1059.4742 | 1160.5218 |
| Fragment 6 1875.9586 | 1274.1393 | 1237.7045 | 1247.5539 | 1160.5218 | 1521.7220 |
| Fragment 7 1514.2579 | 1409.7159 | 1302.2258 | 1410.6172 | 1188.7086 | 1556.7787 |
| Fragment 8 1570.7999 | 1483.2501 | 1358.7678 | 1508.2397 | 1409.7159 | 1613.3207 |
| Fragment 9 1606.3185 | 1539.7921 | 1483.8155 | 1600.3003 | 1491.2579 | 1729.3813 |

Additional information such as instrument acquisition parameters for Experiments 1 and 2 is provided in appendix A and is specific to MEDI7219 (SEQ ID NO:2).
Quantification of the data obtained using the high resolution SCIEX 6600 instrument was then performed as follows:
  For the quantification, extracted ion chromatograms (XIC) using 0.2 Da m/z extraction window centered on the accurate mass of each fragment ion were generated. Accurate mass was calculated from the structure of the compound. The narrow m/z window assured the specificity of the extracted peak area.
  For each precursor ion, multiple fragment ions were used to generate the XIC based on:
    Strong peak intensity in $MS^2$ spectra;
    m/z range: 400-1900;
    Consistency with predicted fragmentation pattern from the structure.
  The chromatograms were integrated and peak areas were calculated with Signal Finder Algorithm and the standard curve was generated using MultiQuant® Software from SCIEX. Concentrations of the target analyte in unknown samples were obtained by regression analysis using linear fits of peak areas vs. analyte concentration, weighted 1/(concentration).
  The quality of the assay was controlled by the quality control samples.
  Either Experiment 1 or Experiment 2 could be used for the quantification of the GLP-1 peptide analogs in high resolution mode.
Data acquisition on the traditional triple quadrupole instrument (SCIEX 5500) was performed as follows:
  The samples were injected and separated with reversed phase chromatography as described above before being ionized and analyzed with a triple quadrupole mass spectrometer.
  The data file for each sample included one SRM experiment. Two product ions of the target compound were monitored.
Quantification of the data obtained using the traditional triple quadrupole instrument (SCIEX 5500) was then performed as follows:
  The product ion with higher signal intensity out of the two that were monitored was used to generate the chromatograms used for analysis.
  The quantification of the target analyte was achieved by integrating chromatograms generated from SRM scans described above and calculating peak areas. Concentrations of the target analyte in unknown samples were obtained by regression analysis using linear fits of peak areas vs. analyte concentration weighted 1/(concentration).
  The quality of the assay was controlled by the quality control samples.

Example 1

In vitro studies using the Caco-2 cell line model revealed sodium caprate, alkyl saccharides, bile salts, and bile salts with propyl gallate combinations as permeation enhancers of glucagon like peptide-1 (GLP-1) peptide analogs.

The Caco-2 cell line is a continuous cell line of heterogeneous human epithelial colorectal adenocarcinoma cells, which when cultured under specific conditions, become differentiated and polarized such that their phenotype, morphologically and functionally, resembles the enterocytes lining the small intestine. Caco-2 cells express tight junctions, microvilli, and a number of enzymes and transporters that are characteristic of such enterocytes. Caco-2 cells are most commonly used as a tight junction monolayer that provides a physical and biochemical barrier to the passage of drugs and thus serves as an in vitro model of the human small intestinal mucosa to predict the absorption of orally administered drugs. Caco-2 permeability assays were performed by Cyprotex US, LLC (MA, USA) to assess the efficacy of different permeation enhancers. Caco-2 cells were grown on Transwell filters until a transepithelial electric resistance of ~1000 ohms/cm$^2$ was achieved. The cells were incubated for three hours with media containing test samples on the apical (top) side of the cell layer, and with blank media on the basolateral (lower) side of the cell layer. Media from the apical and basolateral sides was collected separately after three hours and evaluated for the amount of peptide present on each side. Table 2 gives the permeability coefficient ($Pa_{pp}$) of the various test samples, which include the SEQ ID NO:3 GLP-1 peptide in the presence of different excipients.

The apparent permeability coefficients (Papp) of all polypeptides were calculated using the following equation:
$Papp = dQ/dt \times 1/A\ C_0$ Where dQ/dt is the amount of solutes transported across the Caco-2 barrier in time dt, $C_0$ is the solute concentration in the apical compartment at time zero, and A is the cross-sectional area of the epithelium in contact with apical solution.

Sodium chenodeoxycholate at 25 mg/mL resulted in the highest permeability of the SEQ ID NO:3 peptide across the Caco-2 cell layer ($P_{app}$=10.3).

TABLE 2

Influence of various permeation enhancers on permeability of SEQ ID NO: 3 peptide in Caco-2.

| Sample Description | Permeability Coefficient ($P_{app}$) |
|---|---|
| 0.1 mg/mL SEQ ID NO: 3 peptide | 0 |
| 12.5 mg/mL Tetradecylmaltoside | 0 |
| 12.5 mg/mL Sodium Octanoate | 0 |
| 25.0 mg/mL Sodium Chenodeoxycholate | 0 |
| 10.0 mg/mL Sodium Decanoate | 0 |
| Lauroglycol FCC:Kolliphor EL:Transcutol HP 5:4:3 (v/v) | 0 |
| 0.1 mg/mL SEQ ID NO: 3 Peptide, 12.5 mg/mL Tetradecylmaltoside | 7.8 |
| 0.1 mg/mL SEQ ID NO: 3 Peptide, 2.5 mg/mL Tetradecylmaltoside | 0.88 |
| 0.1 mg/mL SEQ ID NO: 3 Peptide, 0.5 mg/mL Tetradecylmaltoside | 0.05 |
| 0.1 mg/mL SEQ ID NO: 3 Peptide, 12.5 mg/mL Sodium Octanoate | 0 |
| 0.1 mg/mL SEQ ID NO: 3 Peptide, 2.5 mg/mL Sodium Octanoate | 0 |
| 0.1 mg/mL SEQ ID NO: 3 Peptide, 0.5 mg/ Sodium Octanoate | 0 |
| 0.1 mg/mL SEQ ID NO: 3 Peptide, 25.0 mg/mL Sodium Chenodeoxycholate | 10.3 |
| 0.1 mg/mL SEQ ID NO: 3 Peptide, 5.0 mg/mL Sodium Chenodeoxycholate | 6.2 |

TABLE 2-continued

Influence of various permeation enhancers on permeability of SEQ ID NO: 3 peptide in Caco-2.

| Sample Description | Permeability Coefficient ($P_{app}$) |
|---|---|
| 0.1 mg/mL SEQ ID NO: 3 Peptide, 1.0 mg/mL Sodium Chenodeoxycholate | 0 |
| 0.1 mg/mL SEQ ID NO: 3 Peptide, 10.0 mg/mL Sodium Decanoate | 0.4 |
| 0.1 mg/mL SEQ ID NO: 3 Peptide, 2.0 mg/mL Sodium Decanoate | 0 |
| 0.1 mg/mL SEQ ID NO: 3 Peptide, 0.4 mg/mL Sodium Decanoate | 0 |
| 0.1 mg/mL SEQ ID NO: 3 Peptide, ¼ Lauroglycol FCC:Kolliphor EL:Transcutol HP in the weight ratio 5:4:3 (w/w) | 0.05 |
| 0.05 mg/mL SEQ ID NO: 3 Peptide, ⅛ Lauroglycol FCC:Kolliphor EL:Transcutol HP in the weight ratio 5:4:3 (w/w) | 0.09 |

Example 2

The next Caco-2 study was performed to evaluate the ability of additional excipients to enhance the permeability of the SEQ ID NO:3 peptide across tight junction cell layers. Details of this study are listed in Table 3. A combination of sodium chenodeoxycholate (25 mg/mL) and propyl gallate (12.5 mg/mL) resulted in the highest permeability of the SEQ ID NO:3 peptide ($P_{app}$=43.1).

TABLE 3

Influence of various permeation enhancers on permeability of SEQ ID NO: 3 peptide in Caco-2 study.

| Sample Description | Permeability Coefficient ($P_{app}$) |
|---|---|
| 0.1 mg/mL peptide | 0 |
| 0.1 mg/mL SEQ ID NO: 3 Peptide, 12.5 mg/mL Tetradecylmaltoside | 1.4 |
| 0.1 mg/mL SEQ ID NO: 3 Peptide, 12.5 mg/mL Dodecylmaltoside | 6.4 |
| 0.1 mg/mL SEQ ID NO: 3 Peptide, 2.5 mg/mL Dodecylmaltoside | 0 |
| 0.1 mg/mL SEQ ID NO: 3 Peptide, 0.5 mg/mL Dodecylmaltoside | 0 |
| 0.1 mg/mL SEQ ID NO: 3 Peptide, 12.5 mg/mL Sodium Deoxycholate | 0 |
| 0.1 mg/mL SEQ ID NO: 3 Peptide, 2.5 mg/mL Sodium Deoxycholate | 0 |
| 0.1 mg/mL SEQ ID NO: 3 Peptide, 0.5 mg/mL Sodium Deoxycholate | 0 |
| 0.1 mg/mL SEQ ID NO: 3 Peptide, 25 mg/mL Sodium Taurocholate | 0 |
| 0.1 mg/mL SEQ ID NO: 3 Peptide, 5.0 mg/mL Sodium Taurocholate | 0 |
| 0.1 mg/mL SEQ ID NO: 3 Peptide, 1.0 mg/mL Sodium Taurocholate | 0 |
| 0.1 mg/mL SEQ ID NO: 3 Peptide, 6.25 mg/mL Palmitoyl carnitine | 0 |
| 0.1 mg/mL SEQ ID NO: 3 Peptide, 1.25 mg/mL Palmitoyl carnitine | 0 |
| 0.1 mg/mL SEQ ID NO: 3 Peptide, 0.25 mg/mL Palmitoyl carnitine | 0 |
| 0.1 mg/mL SEQ ID NO: 3 Peptide, 6.25 mg/mL Propyl Gallate | 0 |
| 0.1 mg/mL SEQ ID NO: 3 Peptide, 1.25 mg/mL Propyl Gallate | 0 |

TABLE 3-continued

Influence of various permeation enhancers on permeability of SEQ ID NO: 3 peptide in Caco-2 study.

| Sample Description | Permeability Coefficient ($P_{app}$) |
|---|---|
| 0.1 mg/mL SEQ ID NO: 3 Peptide, 0.25 mg/mL Propyl Gallate | 0 |
| 0.1 mg/mL SEQ ID NO: 3 Peptide, 25.0 mg/mL Sodium Chenodeoxycholate, 12.5 mg/mL Propyl gallate | 43.1 |
| 0.1 mg/mL SEQ ID NO: 3 Peptide, 5.0 mg/mL Sodium Chenodeoxycholate, 2.5 mg/mL Propyl gallate | 0 |
| 0.1 mg/mL SEQ ID NO: 3 Peptide, 1.0 mg/mL Sodium Chenodeoxycholate, 0.5 mg/mL Propyl gallate | 0 |

Example 3

A following Caco-2 study was performed to evaluate the permeability of different peptides in the presence of various permeation enhancers. Table 4 provides details of the study. Permeability (%) was calculated by dividing the cumulative amount of molecules transported with the original loading amount. Concentrations of peptides in starting sample and apical and basal solutions after incubation for pre-determined periods were analyzed by HPLC. Sodium chenodeoxycholate at 25 mg/mL effected the highest permeability of each tested peptide (Table 4).

TABLE 4

Influence of various permeation enhancers on permeability of lipidated peptides in Caco-2 study.

| Sample Description | Permeability (%) |
|---|---|
| 0.1 mg/mL SEQ ID NO: 3 | 0 |
| 0.1 mg/mL SEQ ID NO: 3, 25 mg/mL Sodium Chenodeoxycholate | 12.6 |
| 0.1 mg/mL SEQ ID NO: 3, 5.0 mg/mL Sodium Chenodeoxycholate | 1.7 |
| 0.1 mg/mL SEQ ID NO: 3, 25 mg/mL Chitosan | 0 |
| 0.1 mg/mL SEQ ID NO: 3, 5.0 mg/mL Chitosan | 0 |
| 0.1 mg/mL SEQ ID NO: 3, 25 mg/mL Tri-Me-Chitosan | 0 |
| 0.1 mg/mL SEQ ID NO: 3, 5.0 mg/mL Tri-Me-Chitosan | 0 |
| 0.1 mg/mL SEQ ID NO: 3, 25 mg/mL Octyl β-D-glucopyranoside | 2.0 |
| 0.1 mg/mL SEQ ID NO: 3, 5.0 mg/mL Octyl β-D-glucopyranoside | 0 |
| 0.1 mg/mL SEQ ID NO: 4, 25 mg/mL Sodium Chenodeoxycholate | 14.3 |
| 0.1 mg/mL SEQ ID NO: 4, 5.0 mg/mL Sodium Chenodeoxycholate | 0 |
| 0.1 mg/mL SEQ ID NO: 5, 25 mg/mL Sodium Chenodeoxycholate | 10.4 |
| 0.1 mg/mL SEQ ID NO: 5, 5.0 mg/mL Sodium Chenodeoxycholate | 3.2 |
| 0.1 mg/mL SEQ ID NO: 6, 25 mg/mL Sodium Chenodeoxycholate | 13.3 |
| 0.1 mg/mL SEQ ID NO: 6, 5.0 mg/mL Sodium Chenodeoxycholate | 1.21 |
| 0.1 mg/mL SEQ ID NO: 7, 25 mg/mL Sodium Chenodeoxycholate | 10.3 |
| 0.1 mg/mL SEQ ID NO: 7, 5.0 mg/mL Sodium Chenodeoxycholate | 2.1 |
| 0.1 mg/mL SEQ ID NO: 8, 25 mg/mL Sodium Chenodeoxycholate | 11.6 |
| 0.1 mg/mL SEQ ID NO: 8, 5.0 mg/mL Sodium Chenodeoxycholate | 1.7 |
| 0.1 mg/mL SEQ ID NO: 9, 25 mg/mL Sodium Chenodeoxycholate | 13.9 |
| 0.1 mg/mL SEQ ID NO: 9, 5.0 mg/mL Sodium Chenodeoxycholate | 3.1 |

In summary, the in vitro Caco-2 studies revealed the synergistic efficacy of propyl gallate and sodium chenodeoxycholate. Propyl gallate alone showed no peptide permeability across the cell layer (and thus no bioavailability) (Table 3). Sodium chenodeoxycholate alone demonstrated a maximum of 14.3% peptide permeability (Table 4). However, in combination, propyl gallate and sodium chenodeoxycholate demonstrated a peptide permeation of 43.1% (Table 3).

Example 4

Intraduodenal (ID) studies were performed in rats as an in vivo system to demonstrate the efficacy of permeation enhancers attained in the Caco-2 studies. Solution formulations comprising GLP-1 peptide analogs were injected into rats in the duodenum segment of the small intestine. The first ID study involved the use of sodium caprate as the permeation enhancer and the SEQ ID NO:3 GLP-1 peptide analog. Table 5 provides details of this rat ID study. Absolute bioavailability (% F) is a percentage-expressed measure of systemic drug exposure after oral, or in the current example intraduodenal, administration to the systemic exposure generated with intravenous (IV) administration of drug solution. Absolute bioavailability, (% F), is calculated as a percentage of systemic, or blood, drug concentration area under curve (AUC) of the AUC of IV administration adjusted to the amounts of drug given via these routes of administration. Formulation details and pharmacokinetic parameters attained are listed in Table 5. Although SEQ ID NO:3 has low absolute bioavailability (% F) with intraduodenal administration (0.035%) without any formulation intervention, the bioavailability of SEQ ID NO:3 peptide was increased ~20-fold (to 0.71%) by addition of 50 mg/kg sodium caprate (see Table 5.) Gastrointestinal (GI) tract tissues looked normal upon microscopic evaluation following administration of 50 mg/kg sodium caprate.

TABLE 5

Design and outcomes of rat intraduodenal study to test the in vivo efficacy of sodium caprate as a permeation enhancer.

| Test Article | Dosing Route | SEQ ID NO: 3 Dose (mg/kg) | Sodium Caprate Dose (mg/kg) | T max, (hr) | C max, (ng/mL) | AUC, (hr*ng/mL) | T ½, (hr) | F, (%) |
|---|---|---|---|---|---|---|---|---|
| 0.5 mg/mL SEQ ID NO: 3, PBS, pH 8.0 | Intraduodenal | 1 | 0 | 2.30 | 5.1 | 45 | 8.8 | 0.035 |

TABLE 5-continued

Design and outcomes of rat intraduodenal study to test the in vivo efficacy of sodium caprate as a permeation enhancer.

| Test Article | Dosing Route | SEQ ID NO: 3 Dose (mg/kg) | Sodium Caprate Dose (mg/kg) | T max, (hr) | C max, (ng/mL) | AUC, (hr*ng/mL) | T ½, (hr) | F, (%) |
|---|---|---|---|---|---|---|---|---|
| 0.5 mg/mL SEQ ID NO: 3 PBS, 25 mg/mL Sodium Caprate, PBS pH 8.5 | Intraduodenal | 1 | 50 | 0.38 | 34 | 200 | 9.3 | 0.15 |
| 5 mg/mL SEQ ID NO: 3 in PBS, 25 mg/mL Sodium Caprate, PBS pH 8.5 | Intraduodenal | 10 | 50 | 0.44 | 470 | 3800 | 10.0 | 0.29 |
| 25 mg/mL SEQ ID NO: 3 in PBS, 25 mg/mL Sodium Caprate, PBS pH 8.5 | Intraduodenal | 50 | 50 | 0.44 | 6300 | 46000 | 8.3 | 0.71 |
| 0.01 mg/mL SEQ ID NO: 3 in PBS, pH 8.0 | Intravenous | 0.01 | 0 | 0.12 | 210 | 1300 | 10.0 | 100 |
| 0.059 mg/mL SEQ ID NO: 3 in 0.1% BSA-PBS | Subcutaneous | 0.118 | 0 | 9.00 | 460 | 11000 | 11.0 | 71 |

Example 5

Following the initial rat ID study, a second rat ID administration study was performed to evaluate the influence of permeation enhancers identified from the Caco-2 model study. That is, tetradecyl maltoside, sodium chenodeoxycholate, and combination of sodium chenodeoxycholate and propyl gallate were tested for their effect on oral bioavailability of the SEQ ID NO:3 peptide (Table 6).

The second rat ID study revealed that the most effective permeation enhancer (PE) tested for a 1 mg/kg dose of the SEQ ID NO:3 peptide was a combination of 50 mg/kg sodium chenodeoxycholate and 25 mg/kg propyl gallate, which increased the SEQ ID NO:3 peptide oral bioavailability ~20-fold to 0.39% (Table 6). In comparison, the best improvement in permeation of a 1 mg/kg SEQ ID NO:3 peptide dose in the first rat ID study was only ~5-fold (to 0.15%), which was achieved with 50 mg/kg sodium caprate (Table 5).

TABLE 6

Design and pharmacokinetic parameters of SEQ ID NO: 3 peptide solution formulations in intraduodenal study to evaluate the in vivo efficacy of permeation enhancers identified in the Caco-2 studies.

| Test Article | Dosing Route | SEQ ID NO: 3 Dose (mg/kg) | Permeation Enhancer Dose (mg/kg) | T max, (hr) | C max, (ng/mL) | AUC, (hr*ng/mL) | T ½, (hr) | F, (%) |
|---|---|---|---|---|---|---|---|---|
| 0.5 mg/mL SEQ ID NO: 3, PBS, pH 8.0 | ID | 1 | 0 | 8 | 3.16 | 19.4 | NC | 0.02 |
| 0.5 mg/mL SEQ ID NO: 3, 12.5 mg/mL Tetradecylmaltoside, in PBS pH 8.0 | ID | 1 | 25 | 1 | 5.4 | 87.3 | 17.4 | 0.08 |
| 0.5 mg/mL SEQ ID NO: 3 in PBS, 25 mg/mL Tetradecylmaltoside, in PBS pH 8.0 | ID | 1 | 50 | 1 | 5.8 | 63.2 | 10.3 | 0.06 |
| 5 mg/mL SEQ ID NO: 3 in PBS, 25 mg/mL | ID | 10 | 50 | 0.5 | 51.5 | 705 | 8.19 | 0.07 |

TABLE 6-continued

Design and pharmacokinetic parameters of SEQ ID NO: 3 peptide solution formulations in intraduodenal study to evaluate the in vivo efficacy of permeation enhancers identified in the Caco-2 studies.

| Test Article | Dosing Route | SEQ ID NO: 3 Dose (mg/kg) | Permeation Enhancer Dose (mg/kg) | T max, (hr) | C max, (ng/mL) | AUC, (hr*ng/mL) | T ½, (hr) | F, (%) |
|---|---|---|---|---|---|---|---|---|
| Tetradecylmaltoside, in PBS pH 8.0 | | | | | | | | |
| 0.5 mg/mL SEQ ID NO: 3 in PBS, 12.5 mg/mL Sodium Chenodeoxycholate, in PBS pH 8.0 | ID | 1 | 25 | 0.3 | 21.3 | 121.3 | 7.16 | 0.12 |
| 0.5 mg/mL SEQ ID NO: 3 in PBS, 12.5 mg/mL Sodium Chenodeoxycholate, in PBS pH 8.0 | ID | 1 | 50 | 0.5 | 30.9 | 212.3 | 9.3 | 0.21 |
| 0.5 mg/mL SEQ ID NO: 3 in PBS, 12.5 mg/mL Sodium Chenodeoxycholate, in PBS pH 8.0 | ID | 10 | 50 | 0.5 | 379.5 | 2920 | 9.4 | 0.28 |
| 0.5 mg/mL SEQ ID NO: 3 in PBS, 12.5 mg/mL Sodium Chenodeoxycholate, 6.25 mg/mL Propyl Gallate, in PBS pH 8.0 | ID | 1 | 25 + 12.5 | 0.3 | 39.0 | 293 | 9.1 | 0.28 |
| 0.5 mg/mL SEQ ID NO: 3 in PBS, 12.5 mg/mL Sodium Chenodeoxycholate, 6.25 mg/mL Propyl Gallate, in PBS pH 8.0 | ID | 1 | 50 + 25 | 0.5 | 58.1 | 402.5 | 9.9 | 0.39 |
| 0.5 mg/mL SEQ ID NO: 3 in PBS, 12.5 mg/mL Sodium Chenodeoxycholate, 6.25 mg/mL Propyl Gallate, in PBS pH 8.0 | ID | 10 | 50 + 25 | 0.5 | 669.5 | 4332.7 | 10.96 | 0.42 |
| 0.01 mg/mL SEQ ID NO: 3 in PBS, pH 8.0 | Intravenous | 0.01 | 0 | NC | 96.2 | 1028 | 2.9 | 100 |

Example 6

Proteolytic-resistance of mono- or bis-lipidated peptides was evaluated in fasted-state simulated intestinal fluid (FAS-SIF) with Pancreatin®. A fresh suspension of FASSIF/P (Fasted-State Simulated Intestinal Fluid+USP Pancreatin®) was prepared as described by Galia, Nicolaides, Hörter, Lobenberg, Reppas and Dressman: Pharm. Res. 15 (1998) 698-705. The resulting preparation is proteolytically equivalent to ~375 units/mL (375 kU/L) and was used immediately without storage. Peptides for evaluation (1.0 mg, ~250 nmoles) were initially dissolved in pre-warmed FASSIF without Pancreatin® (200 µL) to which was added pre-warmed fresh FASSIF/Pancreatin® (100 µL) to initiate potential digestion. Following momentary vortexing of the Eppendorf reaction tube, the mixture was incubated at 37° C. in a thermostatic water-bath for the duration of the experiment. 25 µL aliquots of the co-incubated peptide-enzyme mixture were periodically withdrawn (t=0, 5 m, 10 m, 15 m, 30 m, 1 h, 2 h) and quenched immediately by addition to a solution of 10% TFA in 1:1 water/acetonitrile (75 µL) to arrest proteolytic activity. Quenched samples were centrifuged (7800 RPM, 3 mins) to pellet solids and 30 µL aliquots of the supernatant solution were analyzed by LC/MS and/or analytical RP-HPLC as follows.

LC/MS method: Agilent Polaris C8-A column (4.6×100 mm, 3 micron) was eluted with a linear binary gradient of 10-90% MeCN (0.1% TFA v/v) in water (0.1% TFA v/v) over 30 mins at 1.5 mL min-1 at ambient temperature with detection by both UV absorption at 210 nm and ionization using a Waters 3100 mass detector (ESI+ mode). Peptide fragments deriving from enzymatic hydrolysis were identified by molecular weight, allowing location of the site of cleavage.

Figure 2A:
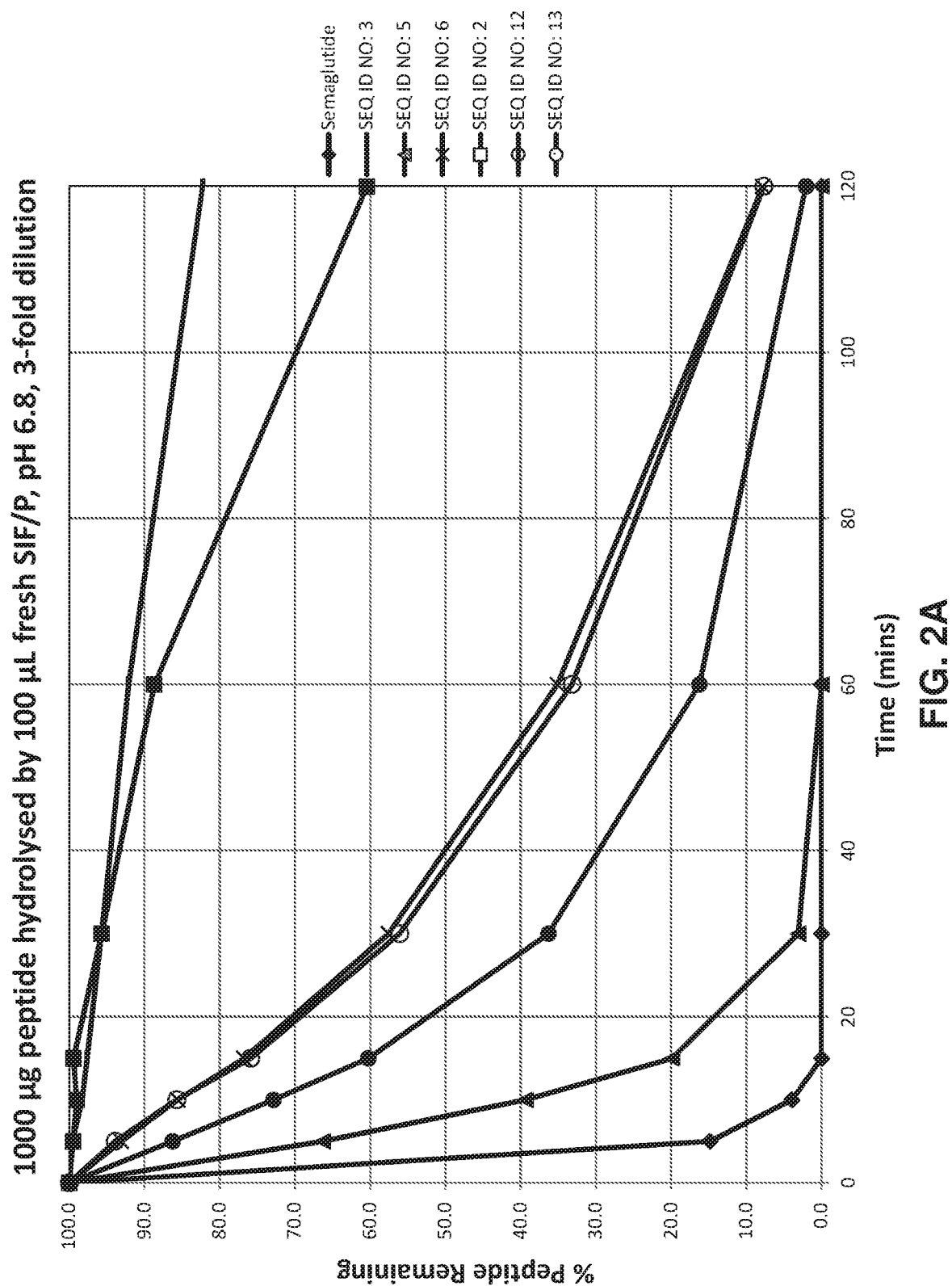
FIG. 2 shows (A) the in vitro stability of GLP-1 peptide analogs and semaglutide in the presence of simulated intestinal fluid with Pancreatin and (B) the in vivo concentration vs. time profile for SEQ ID NO:2 (MEDI7219), SEQ ID NO:6, and semaglutide (SEQ ID NO:11). (See Example 6.)

Analytical RP-HPLC method: Agilent Polaris C8-A column (4.6×100 mm, 3 micron) was eluted with a linear binary gradient of 10-90% MeCN (0.1% TFA v/v) in water (0.1% TFA v/v) over either 10 or 15 mins at 1.5 mL min-1 at 40° C. with detection by UV absorption at 210 nm Manual integration (AUC) allowed estimation of remaining intact peptide over the time course of the experiment (FIG. 2A).

Figure 2B:
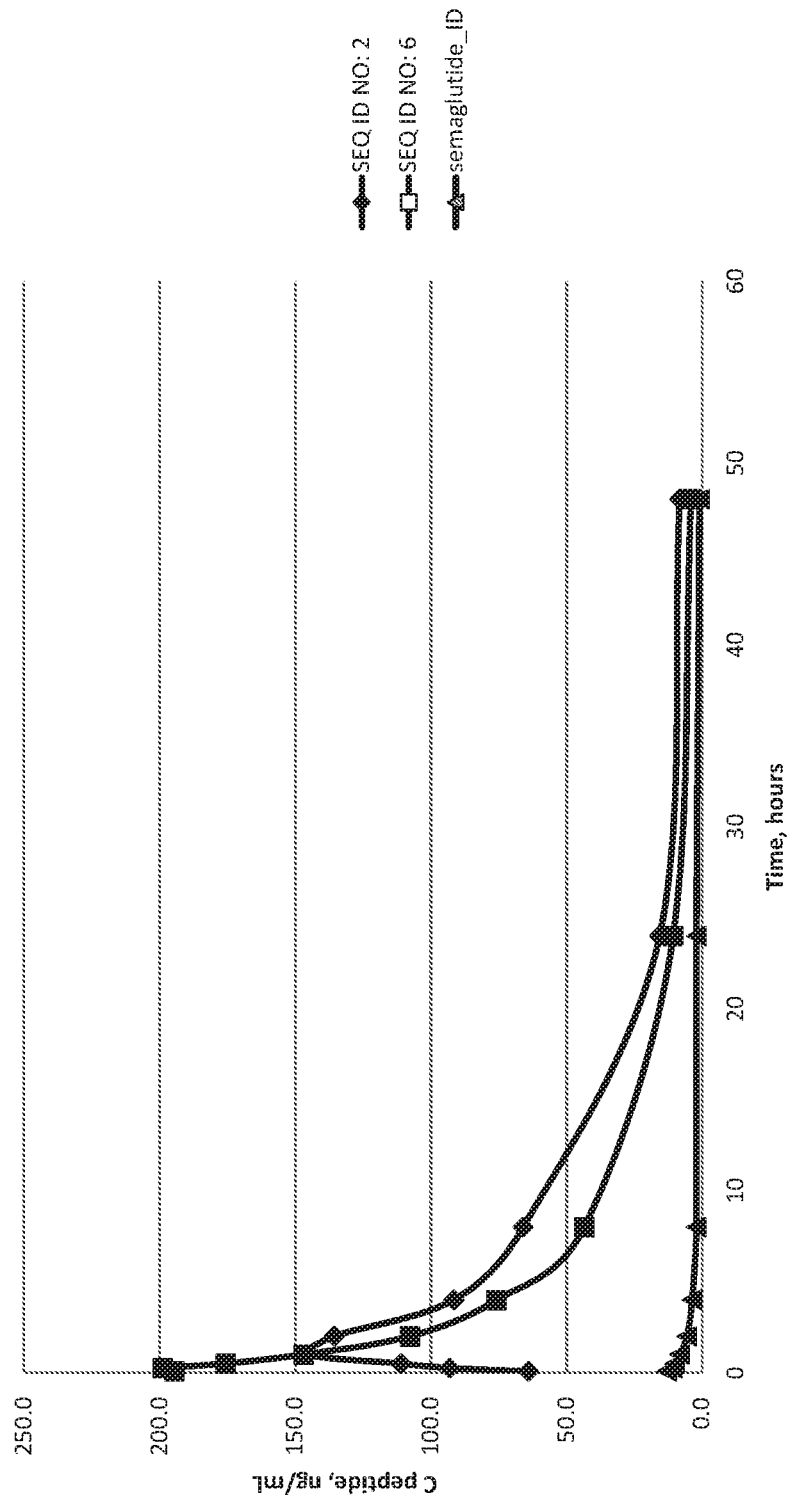

The third rat ID infusion study was performed to compare bioavailability of stabilized peptides MEDI7219 (SEQ ID NO:2) and SEQ ID NO:6 with that of semaglutide, H-His-Aib-Glu-Gly-Thr-Phe-Thr-Ser-Asp-Val-Ser-Ser-Tyr-Leu-Glu-Gly-Gln-Ala-Ala-Lys(AEEAc-AEEAc-γ-Glu-17-carboxyheptadecanoyl)-Glu-Phe-Ile-Ala-Trp-Leu-Val-Arg-Gly-Arg-Gly-OH (SEQ ID NO:11), (Novo Nordisk), an un-stabilized GLP-1 peptide analog, that only has Aib in its sequence for protection from circulating DPP-IV peptidases, (Table 7 and FIG. 2B). Both SEQ ID NO:6 and MEDI7219 (SEQ ID NO:2) stabilized peptides had significantly higher absolute bioavailability via ID route than semaglutide under similar conditions, most likely as a consequence of their improved gastrointestinal proteases stability.

TABLE 7

Design and outcomes of rat intraduodenal study to compare bioavailability of MEDI7219 (SEQ ID NO: 2) and SEQ ID NO: 6 peptide formulations with that of semaglutide formulations.

| Test Article | Dosing Route | GLP-1 Peptide Analog Dose (mg/kg) | Permeation enhancer Dose (mg/kg) | C max, (ng/mL) | AUC, (hr*ng/mL) | T ½, (hr) | F, (%) |
|---|---|---|---|---|---|---|---|
| 0.01 mg/kg MEDI7219 (SEQ ID NO: 2) in 50 mM Tris, 150 mM mannitol buffer, 0.02% Polysorbate 80 | IV | 0.01 | 0 | 264 | 1593 | 17.0 | 100 |
| 0.01 mg/kg SEQ ID NO: 6 in 50 mM Tris, 150 mM mannitol buffer, 0.02% Polysorbate 80 | IV | 0.01 | 0 | 211 | 1075 | 9.2 | 100 |
| 0.01 mg/kg semaglutide (SEQ ID NO: 11) in 50 mM Tris, 150 mM mannitol buffer, 0.02% Polysorbate 80 | IV | 0.01 | 0 | 181 | 955 | 8.8 | 100 |
| 1 mg/kg MEDI7219 (SEQ ID NO: 2) in 50 mg/kg Sodium Chenodeoxycholate, 25 mg/kg Propyl Gallate | ID | 1 | 75 | 154 | 1677 | 10.4 | 1.01 |
| 1 mg/kg SEQ ID NO: 6 in 50 mg/kg Sodium Chenodeoxycholate, 25 mg/kg Propyl Gallate | ID | 1 | 75 | 223 | 1293 | 9.0 | 1.20 |

TABLE 7-continued

Design and outcomes of rat intraduodenal study to compare
bioavailability of MEDI7219 (SEQ ID NO: 2) and SEQ ID NO: 6
peptide formulations with that of semaglutide formulations.

| Test Article | Dosing Route | GLP-1 Peptide Analog Dose (mg/kg) | Permeation enhancer Dose (mg/kg) | C max, (ng/mL) | AUC, (hr*ng/mL) | T ½, (hr) | F, (%) |
|---|---|---|---|---|---|---|---|
| 1 mg/kg semaglutide (SEQ ID NO: 11) in 50 mg/kg Sodium Chenodeoxycholate, 25 mg/kg Propyl Gallate | ID | 1 | 75 | 14.2 | 81 | 15.9 | 0.08 |

Example 7

The following rat ID study compared oral bioavailability of the MEDI7219 (SEQ ID NO:2) peptide formulated with new permeation enhancer formulations after intraduodenal administration in rats. All test articles were prepared as solutions in 50 mM Tris, 150 mM mannitol, 0.02% polysorbate 80, pH 8.5. Table 8 gives the formulation and pharmacokinetic analysis details. Of the permeation enhancers tested, the combination of chenodeoxycholic acid and ethyl gallate works as well or better than the combination of sodium chenodeoxycholate and propyl gallate, providing 2.14% and 1.96% bioavailability, respectively. The control of sodium chenodeoxycholate with propyl gallate resulted in 1.45% bioavailability.

TABLE 8

Study design and pharmacokinetic parameters of rat intraduodenal study to assess oral
bioavailability of the MEDI7219 (SEQ ID NO: 2) peptide formulated with
various permeation enhancers.

| Group | Test Article | Dosing Route | MEDI7219 (SEQ ID NO: 2) Dose (mg/kg) | T max, (hr) | C max, (ng/mL) | AUC-last, (hr*ng/mL) | T ½, (hr) | F, (%) |
|---|---|---|---|---|---|---|---|---|
| 1 | Control Test Article 0.01 mg/mL MEDI7219 (SEQ ID NO: 2) | IV | 0.01 | 0.083 | 187 (5.1) | 1030 (12.5) | 8.90 | 100 |
| 2 | 0.5 mg/mL MEDI7219 (SEQ ID NO: 2), 25 mg/mL Sodium Chenodeoxycholate, 12.5 mg/mL Ethyl Gallate | ID | 1 | 0.25 | 175 (46.9) | 1110 (49.3) | 10.3 | 1.11 |
| 3 | 0.5 mg/mL MEDI7219 (SEQ ID NO: 2), 12.5 mg/mL Sodium Chenodeoxycholate, 25 mg/mL Ethyl Gallate | ID | 1 | 0.25 | 282 (30.3) | 1970 (37.7) | 7.96 | 2.14 |
| 4 | 0.5 mg/mL MEDI7219 (SEQ ID NO: 2), 25 mg/mL Sodium Chenodeoxycholate, 12.5 mg/mL Octyl Gallate | ID | 1 | 0.25 | 240 (47.2) | 1170 (32.8) | 7.97 | 1.12 |
| 5 | 0.5 mg/mL MEDI7219 (SEQ ID NO: 2), 25 mg/mL Chenodeoxycholic acid, 12.5 mg/mL Propyl Gallate | ID | 1 | 0.25 | 546 (53.6) | 1890 (42.5) | 8.60 | 1.92 |
| 6 | 0.5 mg/mL MEDI7219 (SEQ ID NO: 2), 25 mg/mL Ursodeoxycholic acid, 12.5 mg/mL Propyl Gallate | ID | 1 | NA | NA | NA | NA | 0 |

TABLE 8-continued

Study design and pharmacokinetic parameters of rat intraduodenal study to assess oral bioavailability of the MEDI7219 (SEQ ID NO: 2) peptide formulated with various permeation enhancers.

| Group | Test Article | Dosing Route | MEDI7219 (SEQ ID NO: 2) Dose (mg/kg) | T max, (hr) | C max, (ng/mL) | AUC-last, (hr*ng/mL) | T ½, (hr) | F, (%) |
|---|---|---|---|---|---|---|---|---|
| 7 | 0.5 mg/mL MEDI7219 (SEQ ID NO: 2), 25 mg/mL Sodium Chenodeoxycholate, 12.5 mg/mL Propyl Gallate, 25 mg/mL N-Acetyl Cysteine | ID | 1 | NA | NA | NA | NA | 0 |
| 8 | 0.5 mg/mL MEDI7219 (SEQ ID NO: 2), 25 mg/mL Sodium Chenodeoxycholate, 12.5 mg/mL Propyl Gallate | ID | 1 | 2.00 | 140 (21.5) | 1540 (36.1) | 8.83 | 1.45 |

This study compared oral bioavailability of MEDI7219 (SEQ ID NO:2) peptides formulated in additional permeation enhancer formulations after intraduodenal administration in rats. Chenodeoxycholic acid and ethyl gallate works as well or better than sodium chenodeoxycholate and propyl gallate, providing F=2.14% and 1.96% compared to F=1.45% in the control sodium chenodeoxycholate, propyl gallate group.

Example 8

The next rat ID administration study was performed to assess the oral bioavailability and pharmacokinetics of MEDI7219 (SEQ ID NO:2) formulations containing new gallate derivatives, sodium 2-(3,4,5-trihydroxybenzoyloxy) acetate and butanoate, sodium cholate with propyl gallate, sodium caprate with propyl gallate, sodium caprate with propyl gallate and citric acid, and sucrose monododecanoate.

TABLE 9

Design and outcomes of rat intraduodenal study to assess oral bioavailability of the MEDI7219 (SEQ ID NO: 2) peptide formulated with various permeation enhancers.

| Group | Test Article | Dosing Route | Peptide Dose (mg/kg) | PE Dose (mg/kg) | E, (%) and (CV, (%) at Cmax) |
|---|---|---|---|---|---|
| 1 | Control Test Article 0.01 mg/mL MEDI7219 (SEQ ID NO: 2) in 50 mM Tris, 150 mM Mannitol, 0.02% Polysorbate 80, pH 8.5 | IV | 0.01 | 0 | 100 (11.4) |
| 2 | 5 mg/mL MEDI7219 (SEQ ID NO: 2), 25 mg/mL Sodium 2-(3,4,5-trihydroxybenzoyloxy) acetate in 50 mM Tris, 150 mM Mannitol, 0.02% Polysorbate 80, pH 8.5 | ID | 1 | 50 | 0.004 (NA) |
| 3 | 0.5 mg/mL MEDI7219 (SEQ ID NO: 2), 12.5 mg/mL Sodium Chenodeoxycholate, 25 mg/mL Sodium 2-(3,4,5-trihydroxybenzoyloxy) acetate in 50 mM Tris, 150 mM Mannitol, 0.02% Polysorbate 80, pH 8.5 | ID | 1 | 25 + 50 | 0.257 (26.6) |
| 4 | 0.5 mg/mL MEDI7219 (SEQ ID NO: 2), 25 mg/mL Sodium 2-(3,4,5-trihydroxybenzoyloxy) butanoate in 50 mM Tris, 150 mM Mannitol, 0.02% Polysorbate 80, pH 8.5 | ID | 1 | 50 | 0.001 (8.7) |
| 5 | 0.5 mg/mL MEDI7219 (SEQ ID NO: 2), 12.5 mg/mL Sodium Chenodeoxycholate, 25 mg/mL Sodium 2-(3,4,5-trihydroxybenzoyloxy) butanoate in 50 mM Tris, 150 mM Mannitol, 0.02% Polysorbate 80, pH 8.5 | ID | 1 | 25 + 50 | 0.319 (32.9) |

TABLE 9-continued

Design and outcomes of rat intraduodenal study to assess oral bioavailability of the MEDI7219 (SEQ ID NO: 2) peptide formulated with various permeation enhancers.

| Group | Test Article | Dosing Route | Peptide Dose (mg/kg) | PE Dose (mg/kg) | E, (%) and (CV, (%) at Cmax) |
|---|---|---|---|---|---|
| 6 | 0.5 mg/mL MEDI7219 (SEQ ID NO: 2), 12.5 mg/mL Sodium Cholate, 25 mg/mL Propyl Gallate in 50 mM Tris, 150 mM Mannitol, 0.02% Polysorbate 80, pH 8.5 | ID | 1 | 25 + 50 | 0.064 (46.5) |
| 7 | 0.5 mg/mL MEDI7219 (SEQ ID NO: 2), 12.5 mg/mL Sodium Caprate, 25 mg/mL Propyl Gallate in 50 mM Tris, 150 mM Mannitol, 0.02% Polysorbate 80, pH 8.5 | ID | 1 | 25 + 50 | 0.581 (35.2) |
| 8 | 0.5 mg/mL MEDI7219 (SEQ ID NO: 2), 12.5 mg/mL Sodium Caprate, 25 mg/mL Propyl Gallate, 10 mg/mL Citric Acid in 50 mM Tris, 150 mM Mannitol, 0.02% Polysorbate 80, pH 8.5 | ID | 1 | 25 + 50 | 0 (NA) |
| 9 | 0.5 mg/mL MEDI7219 (SEQ ID NO: 2), 25 mg/mL Sucrose monododecanoate in 50 mM Tris, 150 mM Mannitol, 0.02% Polysorbate 80, pH 8.5 | ID | 1 | 50 | 0.023 (39.7) |
| 10 | 0.5 mg/mL MEDI7219 (SEQ ID NO: 2), 12.5 mg/mL Sucrose monododecanoate, 25 mg/mL Propyl Gallate in 50 mM Tris, 150 mM Mannitol, 0.02% Polysorbate 80, pH 8.5 | ID | 1 | 25 + 50 | 0.051 (57.6) |

New gallate derivatives and sodium 2-(3,4,5-trihydroxybenzoyloxy) acetate and butanoate did not work as permeation enhancers for the peptides tested. Addition of sodium chenodeoxycholate increases bioavailability with these excipients. Propyl gallate in combination with sodium cholate results in no bioavailability as opposed to the highest observed bioavailability achieved with propyl gallate in combination with sodium chenodeoxycholate. Combination of sodium caprate and propyl gallate results in moderate bioavailability of ~0.6%. Thus, sodium caprate may improve bioavailability of orally administered peptides. Addition of citric acid reduces MEDI7219 (SEQ ID NO:2) exposure to below level of quantification.

Example 9

Figure 3:
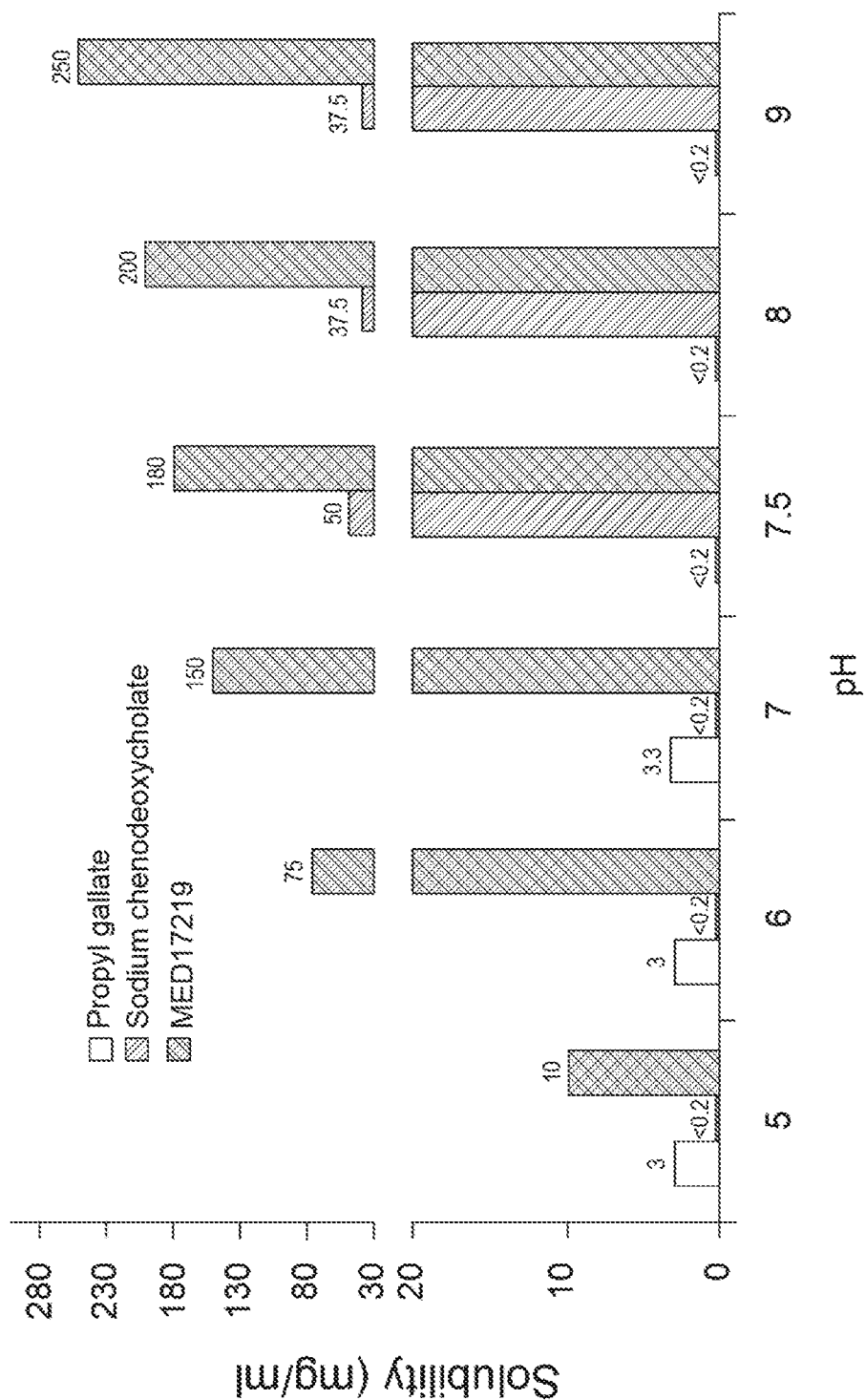
FIG. 3 shows the solubility of propyl gallate, sodium chenodeoxycholate, and SEQ ID NO:2 (MEDI7219) at various pHs. (See Example 9.)

The solubility of the permeation enhancers sodium chenodeoxycholate and propyl gallate, as well as the MEDI7219 (SEQ ID NO:2) GLP-1 peptide analog, were studied independently and also in combinations in phosphate buffer with a pH range of 5.0 to 9.0. A known amount of the permeation enhancer, the peptide, or both were combined with increasing amounts of buffer until the permeation enhancer and/or the peptide were completely solubilized. FIG. 3 and Tables 9-13 show the solubility data. Propyl gallate has low solubility at pH 7.5 and above. The optimal solubility for sodium chenodeoxycholate is in the range of pH 7.5 and above. The combination of sodium chenodeoxycholate and propyl gallate was soluble above pH 7.0. The solubility of MEDI7219 (SEQ ID NO:2) peptide increased in the range of pH 7.0 to 9.0. The addition of sodium chenodeoxycholate and propyl gallate did not change solubility profile of the MEDI7219 (SEQ ID NO:2) peptide, which remained in the range of pH 7.0 to 9.0.

Thus, in order to have optimal MEDI7219 (SEQ ID NO:2) peptide absorption, the pH of solution upon stabilization of dosage form should be in the range of 7.0 to 9.0. This optimal pH may be achieved by the addition of buffer salts that create and maintain the correct pH range at the site of dosage form disintegration/dissolution in the gastrointestinal (GI) tract. The excipients identified in this composition enable optimum solubility of the peptide thereby enabling better absorption. In one aspect of this invention the pharmaceutical excipients identified herein act as a dual agent in maintaining the solubility of the peptide as well as disrupting the tight junctions and providing the action of a permeation enhancer.

TABLE 10

Solubility of propyl gallate in phosphate buffer.

| pH values | Propyl Gallate | Observations |
|---|---|---|
| 5.0 phosphate buffer | 3.0 mg/mL | |
| 6.0 phosphate buffer | 3.0 mg/mL | |
| 7.0 phosphate buffer | 3.3 mg/mL | |
| 7.5 phosphate buffer | <250 µg/mL | Low solubility in neutral pH range |
| 8.0 phosphate buffer | <250 µg/mL | |
| 9.0 phosphate buffer | <250 µg/mL | |

TABLE 11

Solubility of sodium chenodeoxycholate in phosphate buffer.

| pH values | Sodium Chenodeoxycholate | Observations |
|---|---|---|
| 5.0 phosphate buffer | <250 µg/mL | No change in solubility from 10 mg/m mL to 250 µg/mL. |
| 6.0 phosphate buffer | <250 µg/mL | |
| 7.0 phosphate buffer | <250 µg/mL | |
| 7.5 phosphate buffer | 50 mg/mL | Initial gel formation occurs but the gel solubilizes following mixing. |
| 8.0 phosphate buffer | 37.5 mg/mL | |
| 9.0 phosphate buffer | 37.5 mg/mL | |

TABLE 11-continued

Solubility of sodium chenodeoxycholate in phosphate buffer.

| pH values | Sodium Chenodeoxycholate | Observations |
|---|---|---|
| Water USP (pH 5.5) | >200 mg/mL | Initial gel formation occurs but the gel solubilizes following mixing. Solubilization is much faster than for pH 7.5-9.0 |

TABLE 12

Solubility of propyl gallate and sodium chenodeoxycholate in phosphate buffer.

| pH values | 3.125/6.25 mg/mL sodium chenodeoxycholate/propyl gallate | Observations |
|---|---|---|
| 5.0 phosphate buffer | Insoluble | |
| 6.0 phosphate buffer | | |
| 7.0 phosphate buffer | Soluble | Soluble at pH 7.0 and above |
| 7.5 phosphate buffer | | |
| 8.0 phosphate buffer | | |
| 9.0 phosphate buffer | | |
| Water USP (pH 5.5) | Insoluble | |

TABLE 13

Solubility of MEDI7219 (SEQ ID NO: 2) peptide in phosphate buffer.

| pH values | MEDI7219 (SEQ ID NO: 2) | Observations |
|---|---|---|
| 5.0 phosphate buffer | <10 mg/mL | White insoluble residue is present |
| 6.0 phosphate buffer | 75 mg/mL | |
| 7.0 phosphate buffer | 150 mg/mL | Solubility is high with gel formation at high concentrations. |
| 7.5 phosphate buffer | 180 mg/mL | |
| 8.0 phosphate buffer | 200 mg/mL | |
| 9.0 phosphate buffer | >200 mg/mL | |
| Water USP (pH 5.5) | <10 mg/mL | |

TABLE 14

Solubility of MEDI7219 (SEQ ID NO: 2) peptide in the presence of propyl gallate and sodium chenodeoxycholate in phosphate buffer.

| pH values | Peptide solubility in presence of 3.125/6.25 mg/mL sodium chenodeoxycholate/propyl gallate | Observations |
|---|---|---|
| 5.0 phosphate buffer | Insoluble | |
| 6.0 phosphate buffer | | |
| 7.0 phosphate buffer | 160 mg/mL | |
| 7.5 phosphate buffer | 190 mg/mL | |
| 8.0 phosphate buffer | 210 mg/mL | |
| 9.0 phosphate buffer | >200 mg/mL | |
| Water USP (pH 5.5) | Insoluble | |

Example 10

The IntelliCap® system, an electronic oral drug delivery and monitoring device, was used to determine regional absorption for solution formulations. In the form of a capsule, the IntelliCap® incorporates a microprocessor, battery, pH sensor, temperature sensor, radio frequency (RF) wireless transceiver, fluid pump, and drug reservoir. The IntelliCap® system can determine the drug's position in the gastrointestinal (GI) tract by a pH monitoring sensor in the capsule, thereby eliminating the need for in vivo imaging. This system was employed to assess the site of absorption of GLP-1 peptide analogs in the GI tract following oral delivery to canines (Beagle dogs). Solution formulations without permeation enhancer excipients were used as intravenous (IV) and subcutaneous (SC) controls in the study. The design and pharmacokinetic parameters details of this study are provided in Table 15. In brief, solution formulations were prepared and transferred to the IntelliCap® capsule which was dosed to canines, wherein the formulation was released at a specific site in the GI tract.

TABLE 15

Design and pharmacokinetic parameters of SEQ ID NO: 3 in canine site of absorption study.

| Group | Dose (mg/Kg) | Formulation | Dosing route | Tmax (hr) | Cmax (ng/mL) | $AUC_{last}$ (ng · hr/mL) | F, (%) |
|---|---|---|---|---|---|---|---|
| 1 | 0.74 | 8 mg/mL SEQ ID NO: 3, PBS, 10 mg/mL, Sodium Chenodeoxycholate, 2 mg/mL Sodium Caprate, pH 8.0 | PO gavage | 4 | 7.1 | 228.3 | 0.19 |
| 2 | 0.74 | 8 mg/mL SEQ ID NO: 3, PBS, 10 mg/mL Sodium Chenodeoxycholate, 2 mg/mL Sodium Caprate, pH 8.0 | PO IntelliCap ® capsule-proximal small bowel | 0.5 | 60.7 | 1390.5 | 1.14 |
| 3 | 0.74 | 8 mg/mL SEQ ID NO: 3, PBS, 10 mg/mL Sodium Chenodeoxycholate, 2 mg/mL Sodium Caprate, pH 8.0 | PO IntelliCap ® proximal colon | 0.25 | 386.0 | 4836.2 | 3.95 |

TABLE 15-continued

Design and pharmacokinetic parameters of SEQ ID NO: 3 in canine site of absorption study.

| Group | Dose (mg/Kg) | Formulation | Dosing route | Tmax (hr) | Cmax (ng/mL) | AUC$_{last}$ (ng · hr/mL) | F, (%) |
|---|---|---|---|---|---|---|---|
| 4 | 0.01 | 0.1 mg/mL SEQ ID NO: 3 in PBS, pH 8.0 | IV | 0.50 | 140.00 | 1654.72 | 100 |
| 5 | 0.01 | 0.1 mg/mL SEQ ID NO: 3 in PBS, pH 8.0 | SC | 24 | 45.1 | 1751.4 | 105.84 |

This study utilizing the IntelliCap® dosing capsule revealed the highest SEQ ID NO:3 peptide absorption in the proximal colon, followed by the proximal small bowel regions of the GI tract in canines. Therefore, the proximal colon and proximal small bowel represent the best regions for SEQ ID NO:3 peptide delivery to achieve high bioavailability of the peptide. In contrast, significantly lower bioavailability was observed when the animals were dosed via oral gavage into the stomach.

Example 11

An additional site of absorption study was performed to evaluate the best site of absorption of the SEQ ID NO:5 GLP-1 peptide analog solution formulations after oral administration of IntelliCap capsules to canines (Beagle dogs). Delivery of the SEQ ID NO:5 peptide to the proximal small bowel (after pylorus passage), distal small bowel (before ileocecal passage), and proximal colon (after ileocecal passage) were studied. Details of the study are provided in Table 16. The results of this study corroborated the findings from the first site of absorption study performed with the SEQ ID NO:3 peptide (Example 10), wherein the maximum absorption was observed in the proximal colon, followed by the proximal small bowel region of the GI tract in beagle dogs.

TABLE 16

Design and pharmacokinetic parameters of the SEQ ID NO: 5 peptide after solution formulations dosing in canine site of absorption study.

| Group | Dose (mg/Kg) | Formulation | Dosing route | Tmax (hr) | Cmax (ng/mL) | AUClast (ng · hr/mL) | F, (%) |
|---|---|---|---|---|---|---|---|
| 1 | 0.03 | 0.3 mg/mL SEQ ID NO: 5 in 50 mM Tris, 150 mM Mannitol, 0.02% PS80, pH 8.0 | Intravenous | 0.25 | 449 | 1995 | 100 |
| 2 | 0.03 | | Subcutaneous | 4 | 144 | 1772 | 87 |
| 3 | 0.86 | 12 mg/mL SEQ ID NO: 5, 25 mg/mL Sodium Chenodeoxycholate, 12.5 mg/mL Propyl Gallate, 50 mM Tris, 150 mM Mannitol, pH 8.0 filled into MediMetrics IntelliCap ® | Proximal small bowel | 0.25 | 75 | 297 | 0.5 |
| 4 | 0.85 | | Proximal colon | 0.25 | 301 | 1499 | 2.6 |
| 5 | 0.81 | | Distal small bowel | 0.25 | 51 | 166 | 0.3 |

Maximum SEQ ID NO:5 peptide absorption was observed in proximal colon followed by proximal small bowel regions of GI tract in beagle dogs.

Example 12

Figure 6:
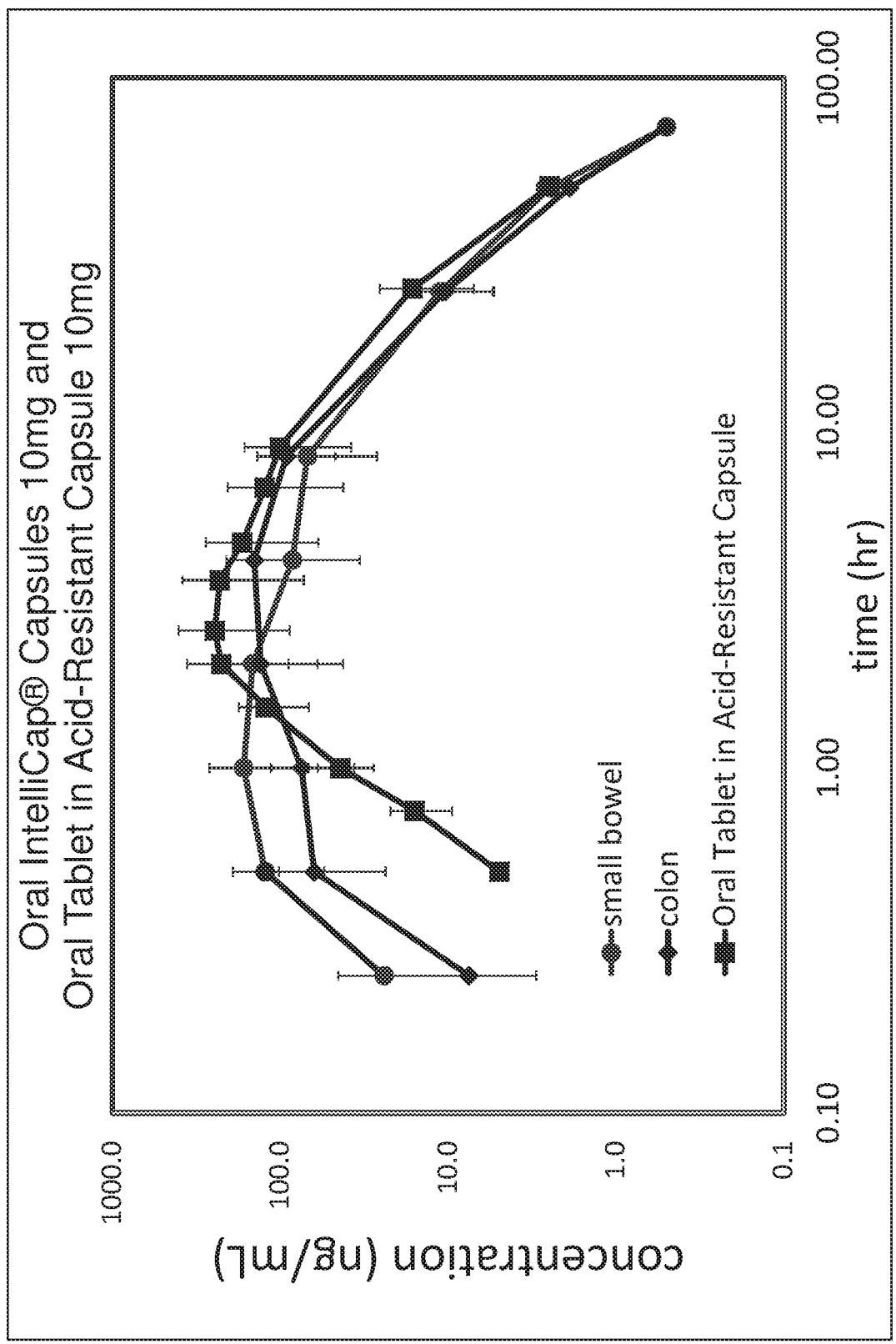
FIG. 6 shows concentration vs. time profile for two 10 mg active pharmaceutical ingredient (API) content tablet formulations: tablets in oral IntelliCap® capsules and oral tablets in acid-resistant capsules (see Example 12).
Figure 7:
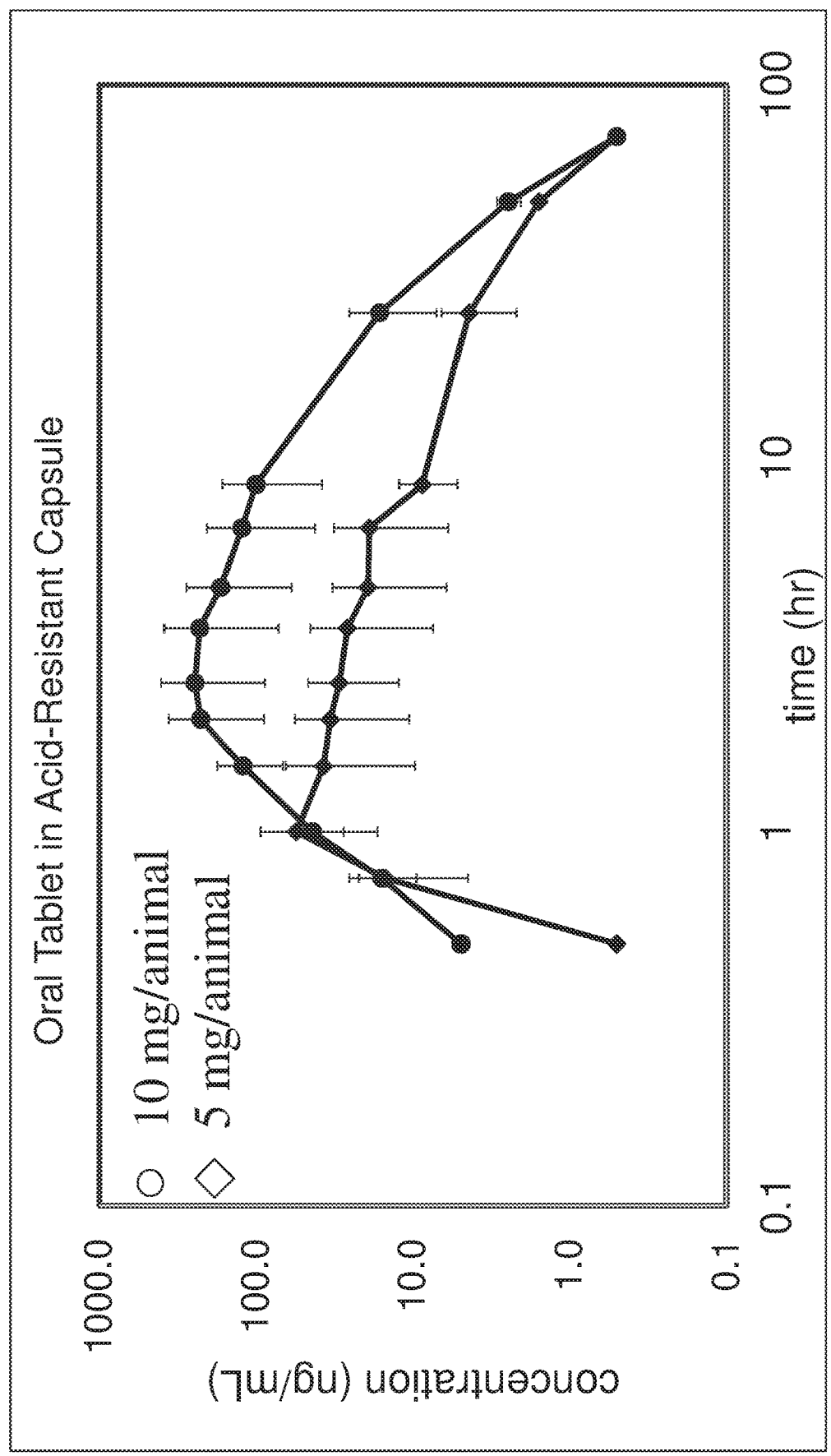
FIG. 7 shows concentration vs. time profile for tablet formulations for 5 mg and 10 mg active pharmaceutical ingredient (API) content tablet formulations. (See Example 12.)
Figure 8:
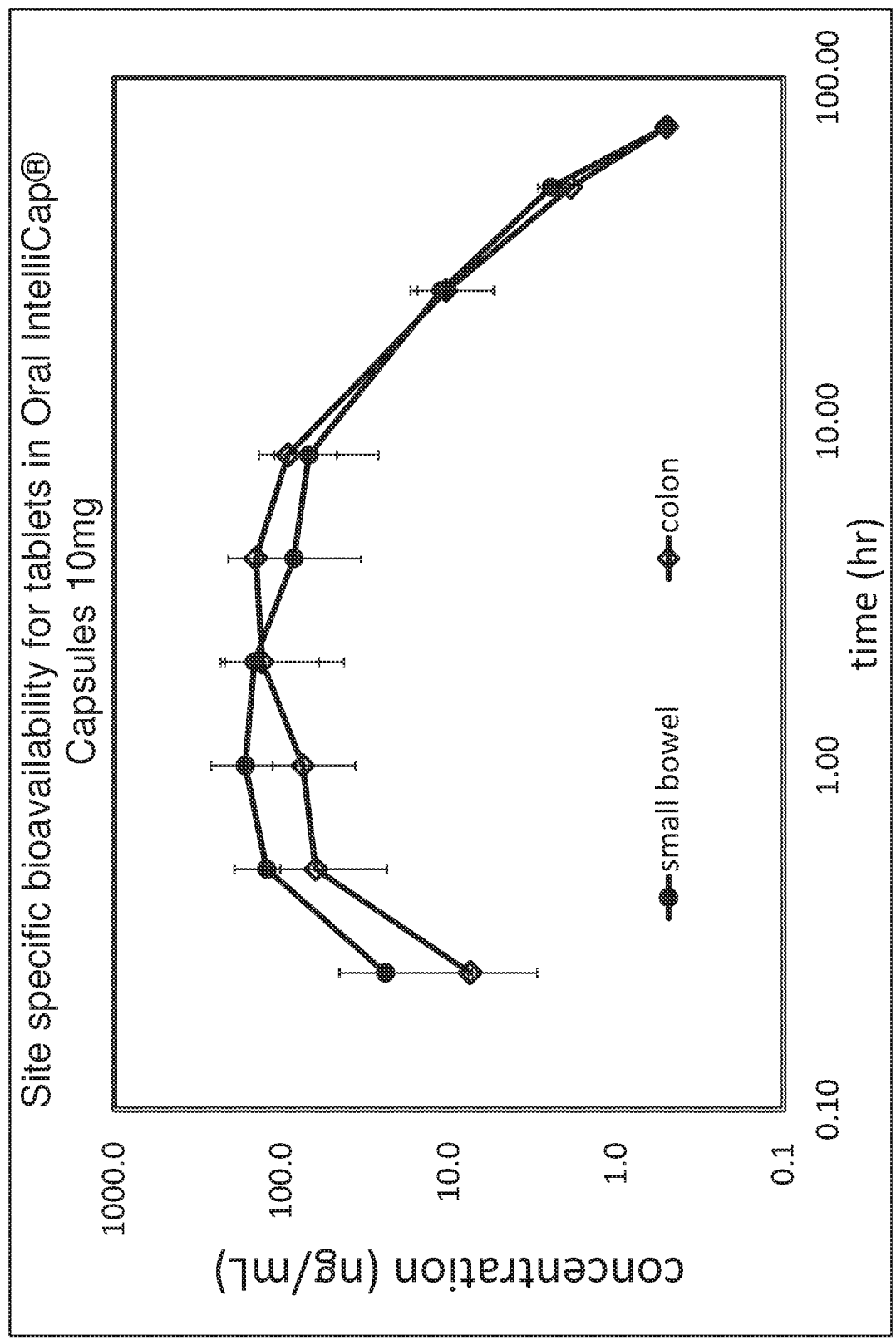
FIG. 8 shows concentration vs. time profile for tablet formulations of group 3 (small bowel) and 4 (colon) from second canine study. (See Example 12.)

A third site of absorption study was performed to evaluate the absorption sites and tablet formulations in acid-resistant capsules in canines. Tablet formulation compositions dosed to dogs are provided in Table 17. The tablet manufacturing process was as follows: All ingredients were passed through a US sieve #35 (0.5 mm opening), and the resultant powder was compacted using a pellet press. Compacted material was again passed through a US sieve #35 (0.5 mm opening) to form granules. Tablets were then compressed at a load of 0.30 to 0.45 ton and a hardness of 34 to 42 N to determine tablet disintegration time, which was found to be 4.40 to 6.30 minutes under these conditions. Tablets in this study were either placed in acid-resistant capsules (Table 18, Groups 1 and 2) or in IntelliCap® (Table 18, Groups 3 and 4). PK parameters are described in Table 18, and PK profiles are provided in FIGS. 6-8. Table 17 provides gastrointestinal transit times obtained using IntelliCap®.

TABLE 17

Tablet formulations compositions tested in site of absorption canine study.

| Ingredient | Function | Amount (mg/tab) |
|---|---|---|
| SEQ ID NO: 6 Peptide | API | 10 or 5 |
| Sodium Chenodeoxycholate | Permeation enhancer, PG solubilizer | 100 |

TABLE 17-continued

Tablet formulations compositions tested in site of absorption canine study.

| Ingredient | Function | Amount (mg/tab) |
|---|---|---|
| Propyl Gallate | Permeation enhancer, enzyme inhibitor | 50 |

TABLE 17-continued

Tablet formulations compositions tested in site of absorption canine study.

| Ingredient | Function | Amount (mg/tab) |
|---|---|---|
| Tris base | pH modifier | 40 |
| Crospovidone | Disintegrant | 50 |
| Total tablet weight (mg) | | 250 |

(CV) for $C_{max}$ was 83 to 138.7% across all oral dose groups. $T_{max}$ appears delayed for colon-targeting IntelliCap® delivery. Administration of SEQ ID NO:6 peptide tablets results in increased transit times at the site of administration and down the gastrointestinal (GI) tract, which is consistent with the known mechanism of action of GLP-1 class drugs.

Example 13

The tablet formulation was optimized using pharmacokinetic data obtained from the above formulations tested in

TABLE 18

Design and pharmacokinetic parameters of SEQ ID NO: 6 peptide after tablet site of absorption canine study.

| Group | No. of animals | Dose (mg/Kg) | Formulation | Dosing route | Tmax, hr (CV) | Cmax, ng/mL (CV) | AUClast, ng · hr/mL (CV) | T1/2, hr | F, (%) |
|---|---|---|---|---|---|---|---|---|---|
| 1 | 7 | 1.08 | 10 mg SEQ ID NO: 6, 100 mg Sodium Chenodeoxycholate, 50 mg Propyl Gallate tablet in Acid-resistant capsule | Oral | 1.79 ± 0.906 (50.8) | 279 ± 334 (119.7) | 1970 ± 2470 (125.2) | 6.31 ± 1.44 (22.9) | 3.63 |
| 2 | 7 | 0.54 | 5 mg SEQ ID NO: 6, 100 mg Sodium Chenodeoxycholate, 50 mg Propyl Gallate tablet in Acid-resistant capsule | Oral | 1.64 ± 0.627 (38.2) | 47.3 ± 65.6 (138.7) | 325 ± 467 (143.6) | 6.99 ± 1.69 (24.2) | 1.30 |
| 3 | 7 | 1.02 | 10 mg SEQ ID NO: 6, 100 mg Sodium Chenodeoxycholate, 50 mg Propyl Gallate tablet in IntelliCap® | Oral IntelliCap® released in proximal small bowel (after pylorus passage) | 0.857 ± 0.556 (64.9) | 185 ± 197 (106.7) | 1340 ± 1610 (120.5) | 6.76 ± 0.454 (6.7) | 2.46 |
| 4 | 7 | 0.96 | 10 mg SEQ ID NO: 6, 100 mg Sodium Chenodeoxycholate, 50 mg Propyl Gallate tablet in IntelliCap® | Oral IntelliCap® released in proximal colon (after ileocecal valve passage) | 2.14 ± 1.35 (62.8) | 210 ± 175 (83.0) | 1490 ± 1310 (87.5) | 5.37 ± 0.921 (17.1) | 2.79 |
| 5 | 3 | 0.031 | 0.031 mg/mL SEQ ID NO: 6 in Tris Mannitol, pH 8.0 | Intravenous | 0.444 ± 0.488 | 27.3 ± 3.47 (27.1) | 147 ± 19.9 (13.5) | 7.21 ± 0.847 (11.7) | N/A |

TABLE 19

Average gastrointestinal transit times measured with IntelliCap, hh:mm and ranges (min-max hh:mm)

| Capsule Actuation Site | Gastric | Small Bowel | Colon | Whole gut |
|---|---|---|---|---|
| Proximal Small Bowel | 01:19 (01:03-1:46) | 10:22 (05:36-14:30) | 09:55 (05:04-21:02) | 21:37 (13:05-32:43) |
| Proximal Colon | 00:52 (00:37-00:59) | 1:45 (00:57-02:26) | 10:31 (03:01-21:56) | 13:09 (06:06-23:30) |

It was found that IntelliCap® Capsules targeting small bowel and colon result in similar bioavailability (Table 18). Comparable exposures ($C_{max}$ and AUC) were observed for all oral formulations at the same dose level. Oral bioavailability ranged from 1.3-3.63%. The coefficient of variation canines, which indicated that a combination of sodium chenodeoxycholate and propyl gallate provides favorable results (Table 20). The formulations tested in this study contained the MEDI7219 (SEQ ID NO:2) peptide, whereas the SEQ ID NO:6 peptide was used in tablet formulations for the previous canine study in Example 12. Tablets were placed in acid-resistant capsules (one tablet/capsule) prior to dosing. Bioavailability was highest for the Group 8 formulation at 10.7% with minimal PK variability of 26%. (Table 20). This formulation contained 0.1 mg/kg MEDI7219 (SEQ ID NO:2) peptide and 300 mg total permeation enhancer (PE) consisting of a 1:2 ratio of sodium chenodeoxycholate to propyl gallate. This ratio worked better compared to a 2:1 ratio of these permeation enhancers (Group 9, Table 20). This study also confirmed the utility of Tris base as a pH stabilizer.

TABLE 20

Design and pharmacokinetic parameters of MEDI7219 (SEQ ID NO: 2) after tablet in acid resistant capsules dosing in canine study.

| Group | No. of animals | Test Article | Dosing Route | MEDI7219 (SEQ ID NO: 2) Dose level | F, (%) | CV at Cmax, (%) |
|---|---|---|---|---|---|---|
| 1 | 3 | 0.1 mg/mL MEDI7219 (SEQ ID NO: 2) in 50 mM Tris, 150 mM Mannitol, 0.02% Polysorbate 80, pH8.0 buffer | Intravenous | 0.01 mg/kg | 100 | — |
| 2 | 5 | 1 mg MEDI7219 (SEQ ID NO: 2), 33.3 mg Sodium Chenodeoxycholate, 16.6 mg Propyl Gallate | Oral tablet in capsule | 1 mg/animal | 0.1 | 36 |
| 3 | 5 | 1 mg MEDI7219 (SEQ ID NO: 2), 16.6 mg Sodium Chenodeoxycholate, 33.3 mg Propyl Gallate | Oral tablet in capsule | 1 mg/animal | 0.03 | 67 |
| 4 | 5 | 10 mg MEDI7219 (SEQ ID NO: 2), 33.3 mg Sodium Chenodeoxycholate, 16.6 mg Propyl Gallate | Oral tablet in capsule | 10 mg/animal | 0.3 | 110 |
| 5 | 5 | 10 mg MEDI7219 (SEQ ID NO: 2), 16.6 mg Sodium Chenodeoxycholate, 33.3 mg Propyl Gallate | Oral tablet in capsule | 10 mg/animal | 1.8 | 63 |
| 6 | 5 | 10 mg MEDI7219 (SEQ ID NO: 2), 100 mg Sodium Chenodeoxycholate, 200 mg Propyl Gallate | Oral tablet in capsule | 10 mg/animal | 6.3 | 74 |
| 7 | 5 | 10 mg MEDI7219 (SEQ ID NO: 2), 200 mg Sodium Chenodeoxycholate, 100 mg Propyl Gallate | Oral tablet in capsule | 10 mg/animal | 4.8 | 35 |
| 8 | 5 | 1 mg MEDI7219 (SEQ ID NO: 2), 100 mg Sodium Chenodeoxycholate, 200 mg Propyl Gallate | Oral tablet in capsule | 1 mg/animal | 10.7 | 26 |
| 9 | 5 | 1 mg MEDI7219 (SEQ ID NO: 2), 200 mg Sodium Chenodeoxycholate, 100 mg Propyl Gallate | Oral tablet in capsule | 1 mg/animal | 5.0 | 42 |
| 10 | 5 | 5 mg MEDI7219 (SEQ ID NO: 2), 75 mg Sodium Chenodeoxycholate, 75 mg Propyl Gallate | Oral tablet in capsule | 5 mg/animal | 3.2 | 97 |
| 11 | 5 | 1 mg MEDI7219 (SEQ ID NO: 2), 500 mg Sodium Chenodeoxycholate, 250 mg Propyl Gallate | Oral tablet in capsule | 1 mg/animal | 11.2 | 27 |
| 12 | 5 | 1 mg MEDI7219 (SEQ ID NO: 2), 33.3 mg Sodium Chenodeoxycholate, 16.6 mg Propyl Gallate (NO TRIS) | Oral tablet in capsule | 1 mg/animal | 0 | 0 |

Example 14

Figure 9:
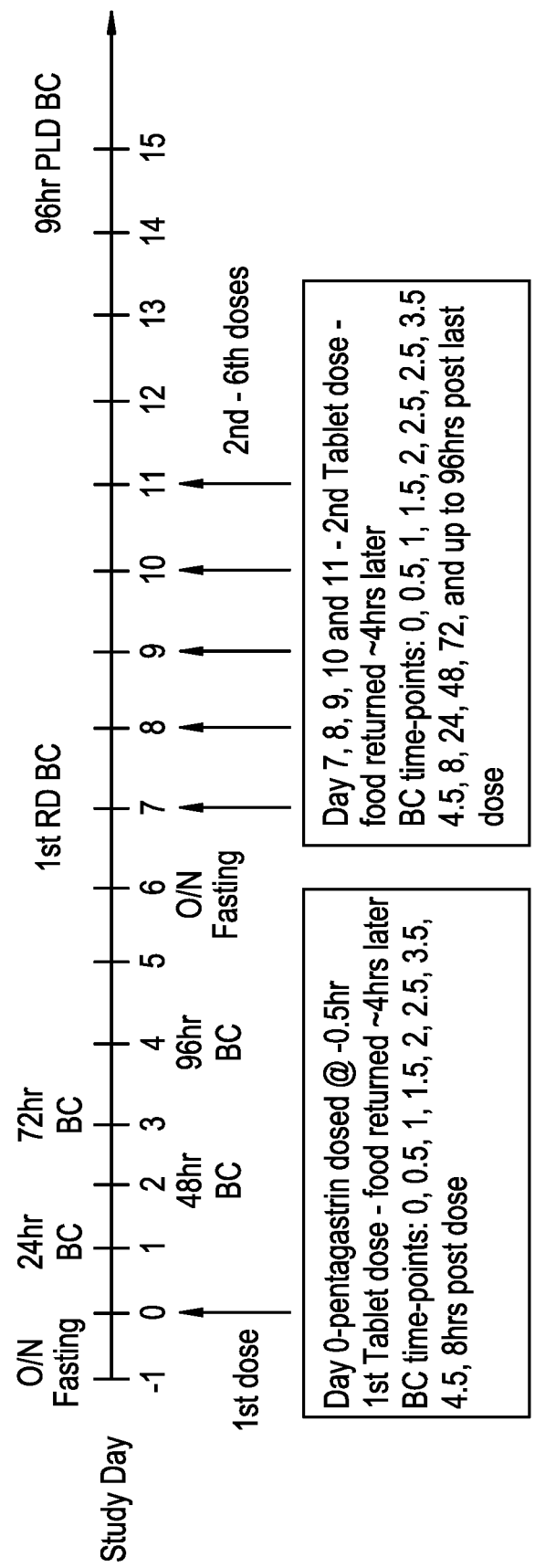
FIG. 9 shows repeated dose design for tablets from group 2 in Table 7. (See Example 14.)
Figure 10:
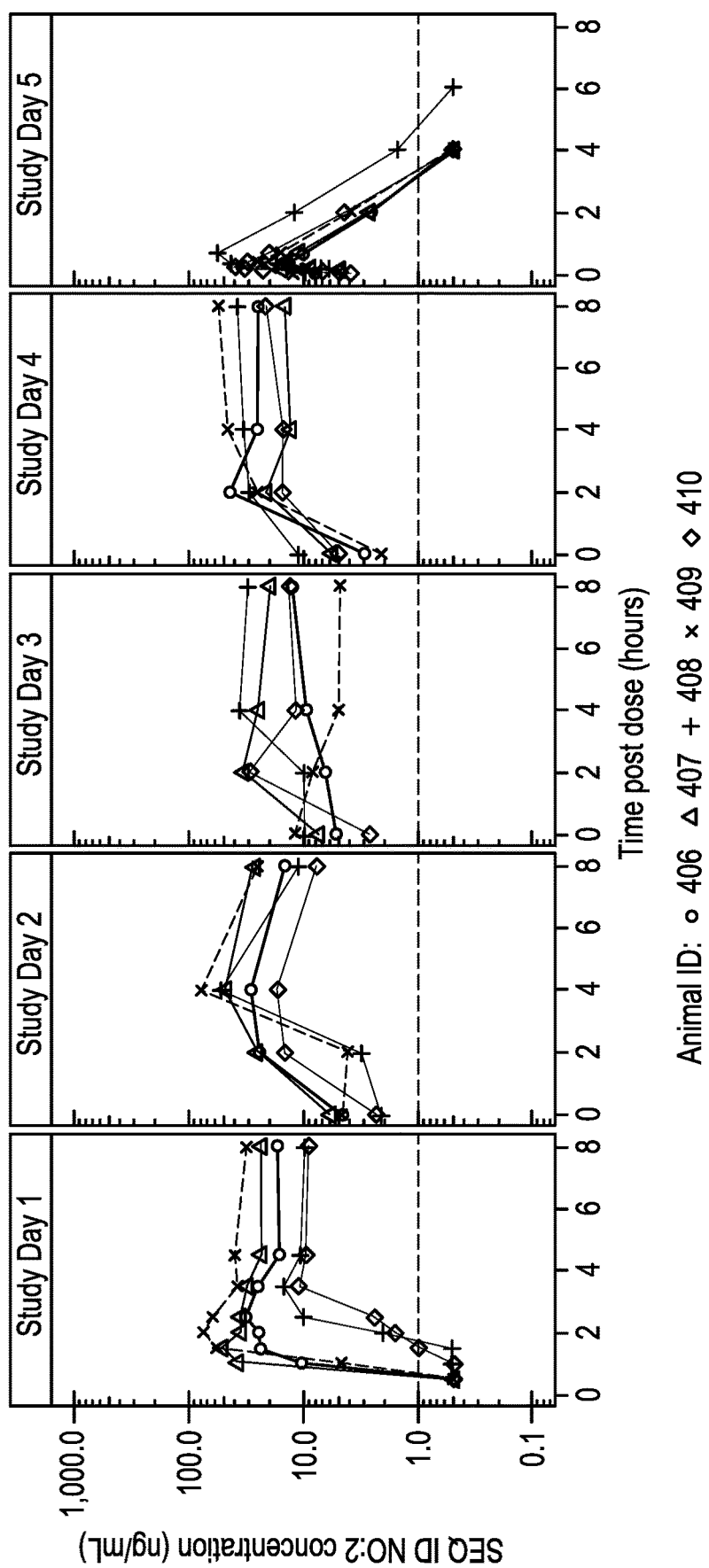
FIG. 10 shows SEQ ID NO:2 (MEDI7219) concentration for repeated tablet dose up to day 5. (See Example 14.)

Tablet optimization was further established in the following canine study. The goals of this study were to evaluate the performance of the group 8 tablet formulation (Example 13, Table 20) as an enterically-coated (EC) tablet and to evaluate repeated dosing of this formulation. A Eudragit formula dissolving at pH 5.5 or above was applied to the tablets as enteric coating. Formulations tested in this canine study are listed in Table 21. Repeated dosing schedule is shown in FIG. 9. Enterically-coated tablets were administered on day 0 followed by a 1 week wash-out. Following wash-out, animals received additional doses on days 7, 8, 9, 10 and 11. Pharmacokinetic profiles of MEDI7219 (SEQ ID NO:2) in multiple dosing arm of the study are shown in FIG. 10.

TABLE 21

Design and pharmacokinetic parameters of MEDI7219 (SEQ ID NO: 2) enterically coated tablets after dosing in canines.

| Group | No. of animals | Test Article | Dosing Route | MEDI7219 (SEQ ID NO: 2) Dose level | F, (%) | CV at Cmax, (%) |
|---|---|---|---|---|---|---|
| 1 | 5 | 0.5 mg/mL MEDI7219 (SEQ ID NO: 2) in 50 mM Tris, 150 mM mannitol, 0.02% Polysorbate 80, pH8.0 buffer | Intravenous | 0.05 mg/kg | 100 | — |
| 2 | 5 | Enterically coated tablet with 1 mg MEDI7219 (SEQ ID NO: 2), 100 mg Sodium Chenodeoxycholate, 200 mg Propyl Gallate | Enterically Coated Oral tablet | 1 mg/animal | 4.6 | 92 |

Enterically-coated group 2 tablet formulation (Table 21), which included 1 mg MEDI7219 (SEQ ID NO:2), 100 mg sodium chenodeoxycholate, and 200 mg propyl gallate, resulted in absolute bioavailability of 4.6%, but with high PK variability of 92%. Repeated dosing of enterically coated tablet resulted in consistent bioavailability with reduced PK variability in subsequent dosing days.

Example 15

The next canine study (Table 22) was executed to confirm the performance of the formulation from the previous study (Example 14, Group 2 formulation, Table 21) at 1, 3 and 10 mg MEDI7219 (SEQ ID NO:2) peptide doses. The second goal was to explore the influence of formulation compositions designed around the Group 2 formulation with varying ratios and amounts of permeation enhancers in an enterically-coated tablet form on bioavailability and pharmacokinetic variability. The following formulation variables were tested: sodium chenodeoxycholate:propyl gallate ratios of 1:1, 1:2, and 1:3; 150, 300 and 450 mg of permeation enhancers at a 1:2 ratio; and 1, 3 and 10 mg peptide doses. All tablets were enterically coated with Eudragit formula dissolving at pH 5.5 and above.

The design and outcomes of this study are described in Table 22. Absolute oral bioavailability >4% for the Group 2 formulation (1 mg MEDI7219 (SEQ ID NO:2) peptide, 100 mg sodium chenodeoxycholate, and 200 mg propyl gallate) in an enterically-coated tablet has been confirmed. The results show that peptide bioavailability was dependent on dose, at 4.2% for a 1 mg dose, 15.5% for a 3 mg dose, and 7.5% for a 10 mg dose. A lower amount of permeation enhancers compared to the Group 2 formulation (that is, 50 mg sodium chenodeoxycholate and 100 mg propyl gallate) still resulted in very high bioavailability of 11.1% for a 3 mg dose and 13.5% for a 10 mg dose. Thus, lower amounts of permeation enhancer enhanced the bioavailability of 10 mg MEDI7219 (SEQ ID NO:2).

TABLE 22

Design and pharmacokinetic parameters of MEDI7219 (SEQ ID NO: 2) enterically coated tablets after dosing in canines.

| Group | No. of animals | Test Article | Dosing Route | MEDI7219 (SEQ ID NO: 2) Dose Level | F, (%) | CV at Cmax, (%) |
|---|---|---|---|---|---|---|
| 1 | 3 | MEDI7219 (SEQ ID NO: 2) | Intravenous | 0.05 mg/kg | 100 | — |
| 2 | 5 | Enterically Coated tablet: 3 mg MEDI7219 (SEQ ID NO: 2), 100 mg Sodium Chenodeoxycholate, 200 mg Propyl Gallate | Oral tablet | 3 mg/animal | 15.5 | 86 |
| 3 | 5 | Enterically Coated tablet: 10 mg MEDI7219 (SEQ ID NO: 2), 100 mg Sodium Chenodeoxycholate, 200 mg Propyl Gallate | Oral tablet | 10 mg/animal | 7.53 | 118.9 |
| 4 | 5 | Enterically Coated tablet: 3 mg MEDI7219 (SEQ ID NO: 2), 75 mg Sodium Chenodeoxycholate, 225 mg Propyl Gallate | Oral tablet | 3 mg/animal | 7.52 | 88.8 |
| 5 | 7 | Enterically Coated tablet: 3 mg MEDI7219 (SEQ ID NO: 2), 50 mg Sodium Chenodeoxycholate, 100 mg Propyl Gallate | Oral tablet | 3 mg/animal | 11.1 | 100.1 |

TABLE 22-continued

Design and pharmacokinetic parameters of MEDI7219 (SEQ ID NO: 2) enterically coated tablets after dosing in canines.

| Group | No. of animals | Test Article | Dosing Route | MEDI7219 (SEQ ID NO: 2) Dose Level | F, (%) | CV at Cmax, (%) |
|---|---|---|---|---|---|---|
| 6 | 7 | Enterically Coated tablet: 10 mg MEDI7219 (SEQ ID NO: 2), 50 mg Sodium Chenodeoxycholate, 100 mg Propyl Gallate | Oral tablet | 10 mg/animal | 13.5 | 94.1 |
| 7 | 5 | Enterically Coated tablet: 3 mg MEDI7219 (SEQ ID NO: 2), 150 mg Sodium Chenodeoxycholate, 300 mg Propyl Gallate | Oral tablet | 3 mg/animal | 7.53 | 80.9 |
| 8 | 5 | Enterically Coated tablet: 3 mg MEDI7219 (SEQ ID NO: 2), 150 mg Sodium Chenodeoxycholate, 150 mg Propyl Gallate | Oral tablet | 3 mg/animal | 6.62 | 73.7 |
| 9 | 5 | Enterically Coated tablet: 1 mg MEDI7219 (SEQ ID NO: 2), 100 mg Sodium Chenodeoxycholate, 200 mg Propyl Gallate | Oral tablet | 1 mg/animal | 4.22 | 14.1 |
| 10 | 5 | 1 mg MEDI7219 (SEQ ID NO: 2), 100 mg Sodium Chenodeoxycholate, 200 mg Propyl Gallate | Oral tablet | 1 mg/animal | 1.11 | 94.7 |
| 11 | 5 | 1 mg MEDI7219 (SEQ ID NO: 2), 100 mg Sodium Chenodeoxycholate, 200 mg Propyl Gallate | Oral tablet | 1 mg/animal | 4.78 | 57.6 |

Example 16

Ten different Multi-unit particulate (MUPS) formulations were prepared (Table 23) using the MEDI7219 (SEQ ID NO:2) peptide and permeation enhancers. The manufacturing process for the MUPS formulation was as follows. A solution of MEDI7219 (SEQ ID NO:2) peptide, sodium chenodeoxycholate and propyl gallate was prepared in water and sprayed onto sugar spheres in a Glatt Mini fluid bed coater. Following drying, sugar spheres coated with peptide and permeation enhancers were coated to result in the compositions described in Table 23. Details of the design and outcomes of this canine study are provided in Table 23.

TABLE 23

Design and pharmacokinetic parameters of MEDI7219 (SEQ ID NO: 2) MUPS formulations dose orally in canines.

| Group | No. of animals | Test Article | Dose Route | MEDI7219 (SEQ ID NO: 2) Dose level | F, (%) | CV at Cmax, (%) |
|---|---|---|---|---|---|---|
| 1 | 5 | MEDI7219 (SEQ ID NO: 2), MUPS 9 mg MEDI7219 (SEQ ID NO: 2), 88 mg Sodium Chenodeoxycholate, 190 mg Propyl Gallate, pH 5.5 EC | Oral capsule | 9 mg/animal | 1.30 | 126.5 |
| 2 | 5 | MEDI7219 (SEQ ID NO: 2), MUPS 9 mg MEDI7219 (SEQ ID NO: 2), 88 mg Sodium Chenodeoxycholate, 190 mg Propyl Gallate, pH 7.0 EC | Oral capsule | 9 mg/animal | 2.54 | 98.4 |
| 3 | 5 | MEDI7219 (SEQ ID NO: 2), MUPS 9 mg MEDI7219 (SEQ ID NO: 2), 88 mg Sodium Chenodeoxycholate, 190 mg Propyl Gallate MUPS, 10% Carbopol 71G Mucoadhesive polymer + 25% pH 5.5 EC | Oral capsule | 9 mg/animal | 0.393 | 91.9 |
| 4 | 5 | MEDI7219 (SEQ ID NO: 2), MUPS 9 mg MEDI7219 (SEQ ID NO: 2), 88 mg Sodium Chenodeoxycholate, 190 mg Propyl Gallate, 10% Carbopol 71G | Oral capsule | 9 mg/animal | 0.582 | 87.4 |

TABLE 23-continued

Design and pharmacokinetic parameters of MEDI7219 (SEQ ID NO: 2) MUPS formulations dose orally in canines.

| Group | No. of animals | Test Article | Dose Route | MEDI7219 (SEQ ID NO: 2) Dose level | F, (%) | CV at Cmax, (%) |
|---|---|---|---|---|---|---|
| 5 | 5 | MEDI7219 (SEQ ID NO: 2), MUPS 9 mg MEDI7219 (SEQ ID NO: 2), 88 mg Sodium Chenodeoxycholate, 190 mg Propyl Gallate, 10% Polycarbophill AA Mucoadhesive polymer + 25% pH 7.0 EC | Oral capsule | 9 mg/animal | 0.124 | 30.2 |
| 6 | 5 | MEDI7219 (SEQ ID NO: 2), MUPS 9 mg MEDI7219 (SEQ ID NO: 2), 88 mg Sodium Chenodeoxycholate, 190 mg Propyl Gallate, 10% Polycarbophill AA Mucoadhesive polymer + 25% pH 5.5 EC | Oral capsule | 9 mg/animal | 0.572 | 64.1 |
| 7 | 5 | MEDI7219 (SEQ ID NO: 2), MUPS 9 mg MEDI7219 (SEQ ID NO: 2), 88 mg Sodium Chenodeoxycholate, 190 mg Propyl Gallate, + 10% Eudragit(RL + RS) + 25% pH 5.5 EC | Oral capsule | 9 mg/animal | 0.537 | NA |

Example 17

In the next canine study, a bioadhesive and controlled release formulation composition of MEDI7219 (SEQ ID NO:2) peptide was evaluated for its bioperformance Table 24 provides the formulation details of this study. Intravenous exposure data were found to be consistent in the prior studies and were used for calculation of absolute oral bioavailability

TABLE 24

Design and pharmacokinetic parameters of MEDI7219 (SEQ ID NO: 2) controlled release and bioadhesive tablet formulations in canines.

| Group | No. of animals | Test Article | Dose route | MEDI7219 (SEQ ID NO: 2) dose level | F, (%) | CV, at Cmax (%) |
|---|---|---|---|---|---|---|
| 1 | 5 | 3 mg MEDI7219 (SEQ ID NO: 2), 100 mg Na CDC, 200 mg PG, 2.5% Carbopol 71G, pH5.5 enteric coating | Oral | 3 mg/dog | 9.86 | 80.2 |
| 2 | 5 | 3 mg MEDI7219 (SEQ ID NO: 2), 100 mg Na CDC, 200 mg PG, 5% Carbopol 71G, pH5.5 enteric coating | Oral | 3 mg/dog | 8.86 | 75.6 |
| 3 | 5 | 3 mg MEDI7219 (SEQ ID NO: 2), 100 mg N CDC, 200 mg PG, 2.5% Carbopol 71G, pH 7.0 enteric coating | Oral | 3 mg/dog | 4.23 | 114.4 |
| 4 | 5 | 3 mg MEDI7219 (SEQ ID NO: 2), 100 mg Na CDC, 200 mg PG, 5% Carbopol 71G, pH 7.0 enteric coating | Oral | 3 mg/dog | 7.93 | 88.6 |
| 5 | 5 | 3 mg MEDI7219 (SEQ ID NO: 2), 100 mg Na CDC, 200 mg PG, 12% Eudragit RSPO, pH 5.5 enteric coating | Oral | 3 mg/dog | 2.87 | 97.7 |
| 6 | 5 | 3 mg MEDI7219 (SEQ ID NO: 2), 100 mg Na CDC, 200 mg PG, 18% Eudragit RSPO, pH 5.5 enteric coating | Oral | 3 mg/dog | 2.25 | 42.5 |
| 7 | 5 | 3 mg MEDI7219 (SEQ ID NO: 2), 100 mg Na CDC, 200 mg PG, pH 5.5 enteric coating (Formulation A from Study # 1468-067) | Oral | 3 mg/dog | 7.81 | 88.8 |

As shown in Table 24, formulations containing Carbopol 71G performed comparably well to immediate release enterically-coated tablets, whereas Eudragit RSPO sustained release formulations did not perform well.

Controlled release may also be achieved via addition of other controlled release excipients. As example Carbopol 971P may be used in tablets at the levels of 0.3# to 3.0%. Enteric coating dissolving at pH 5.5 or pH 7.0, as example, may be utilized to finely control intestinal site where dissolution of enteric coating starts.

Example 18

MEDI7219 (SEQ ID NO:2) formulations were fine-tuned in the following canine study, which was designed to optimize Enterically Coated tablet formulation compositions:
  Evaluate performance of lower PE doses formulations 150 and 75 mg amounts
  Evaluate influence of MEDI7219 (SEQ ID NO:2) peptide dose, 3 and 6 mg: understand if there is a peptide concentration trend between 3 and 10 mg
  Evaluate influence of Enteric Coating pH, 5.5 or 7.0 on the bioavailability
  Evaluate the role of Tris base in solubility and bioavailability of peptide
  Evaluate the role of controlled release and MA component amount on lower PE doses tablet (Pending DOE 2)

The results in Table 25 demonstrate that the reduction of permeation enhancers dose from 150 mg to 75 mg also reduced absolute oral bioavailability (F %). The MEDI7219 (SEQ ID NO:2) dose level (3 mg vs. 6 mg) had no impact on F % for permeation enhancer amount at 150 mg. There was no clear trend showing the impact of Tris base content on F %. Enteric coating pH (5.5 vs. 7.0) did not seem to have marked impact on F % holding other formulation variables constant under this study condition. Higher Carbopol 71G amount (i.e., 5%) did not appear to have apparent impact on F %; however, a higher variability was observed with sustained release tablets. Intravenous exposure data were found to be consistent in the prior studies and were used for calculation of absolute oral bioavailability.

TABLE 25

Design and pharmacokinetic parameters of MEDI7219 (SEQ ID NO: 2) controlled release and bioadhesive tablet formulations in canines.

| Group | No. of Males | Enteric tablet formulation composition, per animal in group | MEDI 7219 (SEQ ID NO: 2) Dose level, mg/animal | PE dose, mg/animal | Tris base, mg/group | CR, % | Enteric Coating pH | Tablets/animal | F, (%) | CV at Cmax, (%) |
|---|---|---|---|---|---|---|---|---|---|---|
| 1 | 5 | 3 mg MEDI7219 (SEQ ID NO: 2), 50 mg Sodium Chenodeoxycholate, 100 mg Propyl Gallate, 18.8 mg Tris base, pH 5.5 EC | 3 | 150 | 18.8 | — | 5.5 | 1 | 6.15 | 51.2 |
| 2 | 5 | 6 mg MEDI7219 (SEQ ID NO: 2), 50 mg Sodium Chenodeoxycholate, 100 mg Propyl Gallate, 18.8 mg Tris base, pH 5.5 EC | 6 | 150 | 18.8 | — | 5.5 | 1 | 6.76 | 91.1 |
| 3 | 5 | 3 mg MEDI7219 (SEQ ID NO: 2), 50 mg Sodium Chenodeoxycholate, 100 mg Propyl Gallate, 18.8 mg Tris base, pH 7.0 EC | 3 | 150 | 18.8 | — | 7.0 | 1 | 4.97 | 90.8 |
| 4 | 5 | 3 mg MEDI7219 (SEQ ID NO: 2), 25 mg Sodium Chenodeoxycholate, 50 mg Propyl Gallate, 9.4 mg Tris base, pH 5.5 EC | 3 | 75 | 9.4 | — | 5.5 | 1 | 1.22 | 69.2 |
| 5 | 5 | 6 mg MEDI7219 (SEQ ID NO: 2), 25 mg Sodium Chenodeoxycholate, 50 mg Propyl Gallate, 9.4 mg Tris base, pH 5.5 EC | 6 | 75 | 9.4 | — | 5.5 | 1 | 3.01 | 106.1 |
| 6 | 5 | 3 mg MEDI7219 (SEQ ID NO: 2), 50 mg Sodium Chenodeoxycholate, 100 mg Propyl Gallate, 9.4 mg Tris base, pH 5.5 EC | 3 | 150 | 9.4 (1/2) | — | 5.5 | 1 | 10.2 | 73.9 |
| 7 | 5 | 3 mg MEDI7219 (SEQ ID NO: 2), 50 mg Sodium Chenodeoxycholate, 100 mg Propyl Gallate, 4.7 mg Tris base, pH 5.5 EC | 3 | 150 | 4.7 (1/4) | — | 5.5 | 1 | 4.90 | 91.9 |
| 8 | 5 | 3 mg MEDI7219 (SEQ ID NO: 2), 50 mg Sodium Chenodeoxycholate, 100 mg Propyl Gallate, 9.4 mg Tris base, pH 7.0 EC | 3 | 150 | 9.4 (1/2) | — | 7.0 | 1 | 2.54 | 62.1 |

TABLE 25-continued

Design and pharmacokinetic parameters of MEDI7219 (SEQ ID NO: 2) controlled release and bioadhesive tablet formulations in canines.

| Group | No. of Males | Enteric tablet formulation composition, per animal in group | MEDI 7219 (SEQ ID NO: 2) Dose level, mg/animal | PE dose, mg/ animal | Tris base, mg/ group | CR, % | Enteric Coating pH | Tablets/ animal | F, (%) | CV at Cmax, (%) |
|---|---|---|---|---|---|---|---|---|---|---|
| 9 | 5 | 3 mg MEDI7219 (SEQ ID NO: 2), 50 mg Sodium Chenodeoxycholate, 100 mg Propyl Gallate, 18.8 mg Tris base, 2.5% Carbopol 71G, pH 7.0 EC | 3 | 150 | 18.8 | 2.5 | 7.0 | 1 | 6.89 | 106.8 |
| 10 | 5 | 3 mg MEDI7219 (SEQ ID NO: 2), 50 mg Sodium Chenodeoxycholate, 100 mg Propyl Gallate, 18.8 mg Tris base, 18% Eudragit RSPO, pH 7.0 EC | 3 | 150 | 18.8 | 18 | 7.0 | 1 | 5.54 | 122.6 |

Example 19

MEDI7219 (SEQ ID NO:2) formulations were fine-tuned in the following canine study (Beagle dogs). The objective was to study influence of MEDI7219 (SEQ ID NO:2) enterically coated tablet formulation composition with or without Tris base on bioperformance Study design and outcomes are provided in Table 26.

This study indicated that MEDI7219 (SEQ ID NO:2) tablets without Tris base still results in meaningful oral bioavailability. Freshly prepared MEDI7219 (SEQ ID NO:2) tablets with Tris results in higher bioavailability 12.4% compared to no Tris tablet 5.2%. Stressed tablet with Tris results in decreased bioavailability 3.8%; but without Tris, bioavailability is 9.6%. Intravenous exposure data were

TABLE 26

Study design.

| Group | No. of Males | MEDI7219 (SEQ ID NO: 2) Test Article and PE dose levels per animal in the group | Dosing Route | MEDI7219 (SEQ ID NO: 2) Dose level | Dose amount | F, (%) | CV at Cmax, % |
|---|---|---|---|---|---|---|---|
| 1 | 5 | 3 mg MEDI7219 (SEQ ID NO: 2), 50 mg Na CDC, 100 mg PG, 19.1 mg Tris, pH5.5 enteric coating- freshly prepared | Oral | 3 mg/dog | 1 tablet/ dog | 12.3 | 130.0 |
| 2 | 5 | 3 mg MEDI7219 (SEQ ID NO: 2), 50 mg Na CDC, 100 mg PG, 0.0 mg Tris, pH5.5 enteric coating- freshly prepared | Oral | 3 mg/dog | 1 tablet/ dog | 5.2 | 86.5 |
| 4 | 5 | 3 mg MEDI7219 (SEQ ID NO: 2), 50 mg Na CDC, 100 mg PG, 19.1 mg Tris, pH5.5 enteric coating exposed to 40C/75% RH for 2 weeks | Oral | 3 mg/dog | 1 tablet/ dog | 3.8 | 97.5 |
| 5 | 5 | 3 mg MEDI7219 (SEQ ID NO: 2), 50 mg Na CDC, 100 mg PG, 0.0 mg Tris, pH5.5 enteric coating | Oral | 3 mg/dog | 1 tablet/ dog | 9.6 | 75.5 | found to be consistent in the prior studies and were used for calculation of absolute oral bioavailability.

Example 20

MEDI7219 (SEQ ID NO:2) formulations were studied in the following canine study, which was designed to compare different tablet delivery systems and peptides in enterically coated tablet formulation compositions delivered orally. The study was designed to:

Evaluate pharmacokinetic parameters of MEDI7219 (SEQ ID NO:2) formulated in sodium n-[8-(2-hydroxybenzoyl)amino]caprylate (SNAC) enterically coated, sodium caprate enterically coated, and Na CDC/PG enterically coated tablets after oral administration to beagle dogs; and Evaluate pharmacokinetic parameters of a peptide of SEQ ID NO:10 formulated in SNAC enterically coated and Na CDC/PG enterically coated tablets after oral administration to beagle dogs.

The results in Table 27 demonstrate that the best MEDI7219 bioavailability was demonstrated with control Na CDC/PG enterically coated tablet platform: F % of 5.92 and PK variability of 54.2%. Na caprate enterically coated tablets demonstrated comparable MEDI7219 (SEQ ID NO:2) F of 4.46% and PK variability of 58.6% to Na CDC/PG platform. The peptide of SEQ ID NO:10 demonstrated an oral F of 1.93% and PK variability of 52.3%, and a longer $T_{1/2}$ than MEDI7219 (SEQ ID NO:2) (33 hrs vs. 10 hrs), resulting in higher AUC (23700 vs. 13500 ng·hr/mL) in a similar formulation. SNAC provided F % to MEDI7219 (SEQ ID NO:2) of 1.1% and provided F % to the peptide of SEQ ID NO:10 of 0.61%. Intravenous exposure data were found to be consistent in the prior studies and were used for calculation of absolute oral bioavailability in current study.

TABLE 27

Design and pharmacokinetic parameters of MEDI7219 (SEQ ID NO: 2) and SEQ ID NO: 10 enterically coated tablet formulations in canines.

| Group | No. of Males | MEDI7219 (SEQ ID NO: 2) and SEQ ID NO: 10 Test Article and PE dose levels per animal in the group | Dosing Route | Peptide Dose level | Dose amount | F, (%) | CV at Cmax % |
|---|---|---|---|---|---|---|---|
| 1 | 5 | 20 mg MEDI7219 (SEQ ID NO: 2), 300 mg SNAC, pH5.5 enteric coating | Oral | 20 mg/dog | 2 tablets/ dog | 1.10 | 69.8 |
| 2 | 5 | 20 mg MEDI7219 (SEQ ID NO: 2), 300 mg Na Caprate, pH5.5 enteric coating (22% mannitol) | Oral | 20 mg/dog | 2 tablets/ dog | 4.46 | 58.6 |
| 3 | 5 | 20 mg MEDI7219 (SEQ ID NO: 2), 100 mg Na CDC, 200 mg PG, 38.2 mg Tris, pH5.5 enteric coating | Oral | 20 mg/dog | 2 tablets/ dog | 5.92 | 54.2 |
| 4 | 5 | 20 mg SEQ ID NO: 10, 300 mg SNAC, pH5.5 enteric coating | Oral | 20 mg/dog | 2 tablets/ dog | 0.61 | 69.0 |
| 5 | 5 | 20 mg SEQ ID NO: 10, 100 mg Na CDC, 200 mg PG, 38.2 mg Tris, pH5.5 enteric coating | Oral | 20 mg/dog | 2 tablets/ dog | 1.93 | 52.3 |

Example 21

Sodium chenodeoxycholate may be present if different crystalline polymorph forms depending on solvate and preparation procedures, with polymorphs A and B are most common hydrate forms. The following canine study was designed to evaluate the influence of sodium chenodeoxycholate (Na CDC) polymorphs A and B on MEDI7219 (SEQ ID NO:2) pharmacokinetic parameters formulated in enterically coated tablets after oral administration to beagle dogs.

The results in Table 28 demonstrate that Na CDC polymorph A tablets resulted in similar MEDI7219 (SEQ ID NO:2) pharmacokinetic parameters (F=2.34%, CV=76.4%) compared to polymorph B tablets (F=1.79%, CV=56.0%). A change from polymorph A to polymorph B or vice versa should not result in significant differences in bioperformance Other polymorph forms may be used in formulations described in this disclosure.

TABLE 28

Design and pharmacokinetic parameters of MEDI7219 (SEQ ID NO: 2) enterically coated tablet formulations in canines

| Group | No. of Males | MEDI7219 (SEQ ID NO: 2) Test Article and PE dose levels per animal in the group | Dosing Route | Peptide Dose level | Dose amount | Average F % | Average Cmax (ng/mL) | CV at Cmax, % |
|---|---|---|---|---|---|---|---|---|
| 1 | 5 | 3 mg MEDI7219 (SEQ ID NO: 2), 50 mg Na CDC polymorph A, 100 mg PG pH5.5 enteric coating | Oral | 3 mg/dog | 1 tablet/dog | 2.34 | 69.6 | 76.4 |
| 2 | 5 | 3 mg MEDI7219 (SEQ ID NO: 2), 50 mg Na CDC polymorph B, 100 mg PG pH5.5 enteric coating | Oral | 3 mg/dog | 1 tablet/dog | 1.79 | 47.6 | 56.0 |

Example 22

MEDI7219 (SEQ ID NO:2) formulations were studied in the following canine study, which was designed to:

Explore the influence of formulation compositions with changing ratios of sodium chenodeoxycholate (Na CDC) to propyl gallate (PG); and Explore the influence of the amount of permeation enhancers (PE) and the MEDI7219 dose in an enterically coated tablet on bioavailability and PK variability after oral administration to Beagle dogs.

The results in Table 29 demonstrate that a lower ratio of Na CDC:PG in 150 mg PE tablets demonstrated good MEDI7219 bioavailability in dogs: a formulation with a 2:1 Na CDC:PG ratio resulted in F ~7% whereas a formulation with a 1:2 Na CDC:PG ratio resulted in F ~6%. A tablet with a 6.5:1 Na CDC:PG ratio (130 mg Na CDC, 20 mg PG) still delivered good MEDI7219 F ~4%. Tablets with 150 mg Na CDC and no PG demonstrated F ~2%. Lower weight tablets containing 75 mg PE, 65 mg Na CDC: 10 mg PG (6.5:1 ratio), demonstrated exposures of F ~1 to 2%.

TABLE 29

Design and pharmacokinetic parameters of MEDI7219 (SEQ ID NO: 2) enterically coated tablet formulations in canines.

| Group | No. of Males | MEDI7219 Test Article and PE dose levels per animal in the group | Dosing Route | MEDI7219 Dose level mg/animal | PE Dose levels, mg/animal Na CDC:PG | % F | Cmax (ng/mL) | CV at Cmax % |
|---|---|---|---|---|---|---|---|---|
| 1 | 5 | EC tablet 3 mg MEDI7219 (SEQ ID NO: 2), 50 mg Na CDC, 100 mg PG | Oral | 3 | 50:100 1:2 | 5.99 | 208 | 111.0 |
| 2 | 5 | EC tablets 3 mg MEDI7219 (SEQ ID NO: 2), 100 mg Na CDC, 50 mg PG | Oral | 3 | 100:50 2:1 | 6.58 | 214 | 75.3 |
| 3 | 5 | EC tablets 3 mg MEDI7219 (SEQ ID NO: 2), 130 mg Na CDC, 20 mg PG | Oral | 3 | 130:20 6.5:1 | 3.85 | 128 | 41.8 |
| 4 | 5 | EC tablets 3 mg MEDI7219 (SEQ ID NO: 2), 150 mg Na CDC, 0 mg PG | Oral | 3 | 150:0 X:0 | 1.70 | 45.3 | 98.1 |
| 5 | 5 | EC tablets 3 mg MEDI7219 (SEQ ID NO: 2), 65 mg Na CDC, 10 mg PG | Oral | 3 | 65:10 6.5:1 | 1.59 | 70.3 | 86.5 |
| 6 | 5 | EC tablets 10 mg MEDI7219 (SEQ ID NO: 2), 65 mg Na CDC, 10 mg PG | Oral | 10 | 65:10 6.5:1 | 1.25 | 138 | 77.8 |

Example 23

MEDI7219 (SEQ ID NO:2) formulations were studied in the following canine study, which was designed to explore formulation compositions around 6.5:1 ratio of Na Chenodeoxycholate (Na CDC) to Propyl Gallate (PG) in enterically coated tablet.

Figure 12:
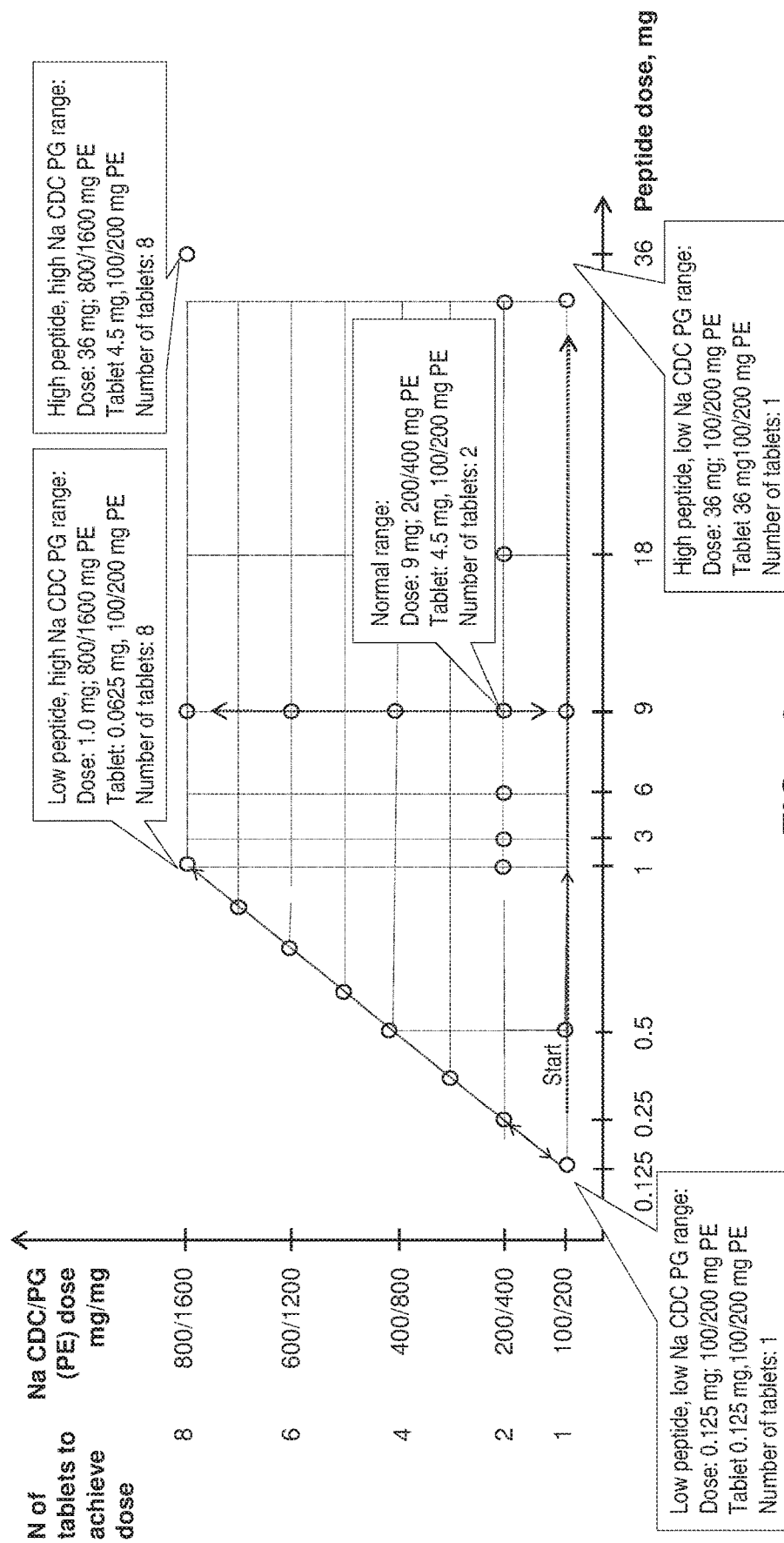
FIG. 12 shows the clinical formulation design space and ranges for enterically coated tablets containing sodium chenodeoxycholate and propyl gallate. (See Example 24.)

The results in Table 30 demonstrate that a 4:1 ratio, 120 mg Na CDC and 30 mg PG, 3 mg MEDI7219 tablet achieved MEDI7219 F~5.7% with PK variability (CV) at C max of 52.8%. A 14:1 Na CDC:PG ratio, 140 mg Na CDC and 10 mg PG, 3 mg MEDI7219 tablets achieved MEDI7219 bioavailability in dogs F~4.6% with PK variability at C max of 84.4%. A 29:1 Na CDC:PG ratio, 145 mg Na CDC and 5 mg PG, 3 mg MEDI7219 tablets achieved MEDI7219 bioavailability in dogs F~3.8% with PK variability at C max of 135.3%. A No PG formulation, containing 150 mg Na CDC tablets achieved F~0.6%.

be adjusted to achieve the required doses eliciting the desired pharmacodynamics response. The clinical formulation design space and ranges in shown in FIG. 12.

Figure 13:
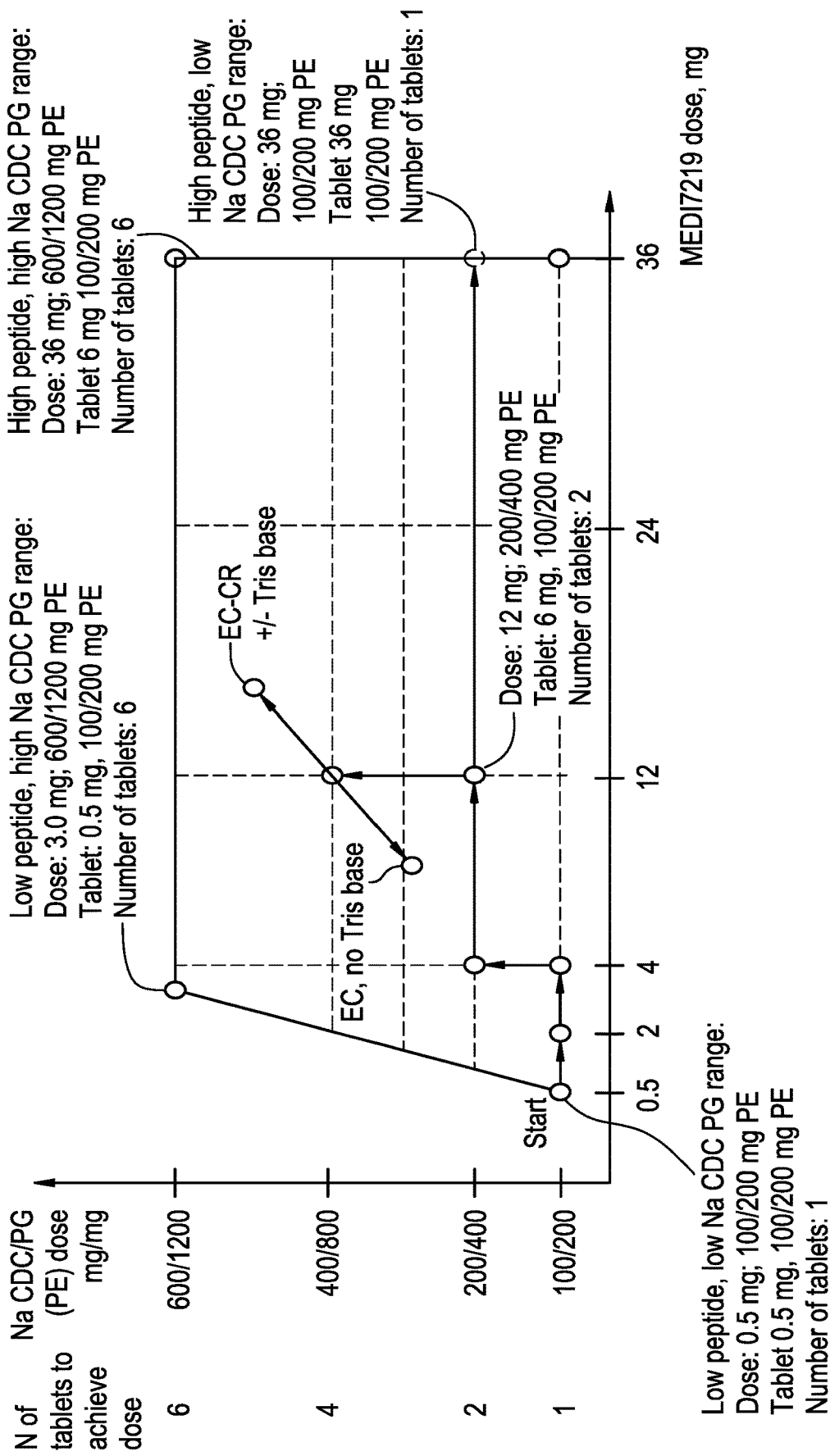
FIG. 13 shows the clinical formulation design space and ranges for additional enterically coated tablets containing sodium chenodeoxycholate and propyl gallate. (See Example 24.)

An additional clinical formulation design space is shown in FIG. 13. In this clinical formulation design space, MEDI7219 peptide rages from 0.5 to 36 mg are studied with permeation enhancer ranges from 100 mg Na CDCA with 200 mg of PG to 600 mg of Na CDCA with 1200 mg of PG. The ratio of permeation enhancers is maintained at a constant 1:2 ratio in this study, and up to six tablets are dosed. The tablets are enterically coated and contain Tris base. After achieving reliable exposures with MEDI7219 in enterically coated tablets with Tris base at given peptide and permeation enhancer levels, enterically coated tablets without Tris base and enterically coated-controlled release tablets with or without Tris base are evaluated.

TABLE 30

Design and pharmacokinetic parameters of MEDI7219 (SEQ ID NO: 2) enterically coated tablet formulations in canines.

| Group | No. of Males | MEDI7219 Test Article and PE dose levels per animal in the group | Dosing Route | MEDI7219 Dose level, mg/animal | PE Dose levels, mg/animal Na CDC:PG | % F | Cmax (ng/mL) | CV at Cmax % |
|---|---|---|---|---|---|---|---|---|
| 1 | 5 | Formulation A: EC tablets 3 mg MEDI7219, 120 mg Na CDC, 30 mg PG | Oral | 3 | 120:30 4:1 | 5.65 | 208 | 52.8 |
| 2 | 5 | Formulation C: EC tablets 3 mg MEDI7219, 140 mg Na CDC, 10 mg PG | Oral | 3 | 140:10 14:1 | 4.55 | 139 | 84.4 |
| 3 | 5 | Formulation E: EC tablets 3 mg MEDI7219, 145 mg Na CDC, 5 mg PG | Oral | 3 | 145:5 29:1 | 3.79 | 85.6 | 135.3 |
| 4 | 5 | Formulation D: EC tablets 3 mg MEDI7219, 150 mg Na CDC, 0 mg Propyl Gallate | Oral | 3 | 150:0 X:0 | 0.56 | 25.1 | 59.0 |

Example 24

Exemplary oral formulations for administration to humans are shown in Tables 31-36. These compositions can be prepared with flexibility to adjust the peptide dose, permeation enhancer dose, and tablet weight. The tablet weight and number of tablets given to a human patient can

TABLE 31

Examples of compositions of immediate release enterically coated tablets.

| Ingredient | Function | Composition, % | Low peptide range, mg/tablet | Intermediate peptide range, mg/tablet | High peptide clinical range, mg/tablet |
|---|---|---|---|---|---|
| Peptide tablet nominal strength, mg | Active | 0.0256-7.36 | 0.125 | 4.5 | 36 |
| Sodium chenodeoxycholate | Permeation enhancer | 20.50 | 100.0 | 100.0 | 100.0 |
| Propyl gallate | Permeation enhancer | 40.90 | 200.0 | 200.0 | 200.0 |
| Mannitol | Filler, diluent | 6.8-10.57 | 94.7 | 89.6 | 51.8 |
| Tris base | pH Stabilizing agent | 0.00-7.41 | 0.0-36.2 | 0.0-36.2 | 0.0-36.2 |
| Crospovidone, Kollidon CL | Disintegrant | 5.81 | 28.4 | 28.4 | 28.4 |
| Aerosil 300 | Glidant | 1.00 | 4.9 | 4.9 | 4.9 |
| Sodium Stearyl Fumarate | Lubricant | 5.00 | 24.4 | 24.4 | 24.4 |

TABLE 31-continued

Examples of compositions of immediate release enterically coated tablets.

| Ingredient | Function | Composition, % | Low peptide range, mg/tablet | Intermediate peptide range, mg/tablet | High peptide clinical range, mg/tablet |
|---|---|---|---|---|---|
| Total tablet: | Oral tablet | 100.00 | 488.8 | 488.8 | 488.8 |
| Eudragit formula | Enteric coating | +12.5% weight gain | 61.2 | 61.2 | 61.2 |
| Total tablet with Enteric Coating | EC tablet | 100 | 550.0 | 550.0 | 550.0 |

Exemplary oral formulations can include peptide ranges from 0.25 to 36 mg of MEDI7219 (SEQ ID NO:2) and permeation enhancers in ranges from 100 mg Sodium Chenodeoxycholate (Na CDC) and 200 mg of propyl gallate (PG) to 800 mg Sodium Chenodeoxycholate and 1600 mg of propyl gallate. The ratio of permeation enhancers Na CDC: PG can be 1:2. Tris base and controlled release excipients (e.g. Carbopol 71G 1-10% and Carbopol 971P 0.3-3%) can be used.

TABLE 32

Additional examples of compositions of immediate release enterically coated tablets.

| Ingredient | Function | Composition, % | Low peptide range, mg/tablet | Intermediate peptide range, mg/tablet | High peptide clinical range, mg/tablet |
|---|---|---|---|---|---|
| Peptide tablet nominal strength, mg | Active | 0.0256-7.36 | 0.125 | 4.5 | 36 |
| Sodium Chenodeoxycholate | Permeation enhancer | 20.50-61.4 | 100.0-300.0 | 100.0-300.0 | 100.0-300.0 |
| Propyl Gallate | Permeation enhancer | 40.90-0.0 | 200.0-0.0 | 200.0-0.0 | 200.0-0.0 |
| Mannitol | Filler, diluent | 6.8-10.57 | 94.7 | 89.6 | 51.8 |
| Tris base | pH Stabilizing agent | 0.00-7.41 | 0.0-36.2 | 0.0-36.2 | 0.0-36.2 |
| Crospovidone, Kollidon CL | Disintegrant | 5.81 | 28.4 | 28.4 | 28.4 |
| Aerosil 300 | Glidant | 1.00 | 4.9 | 4.9 | 4.9 |
| Sodium Stearyl Fumarate | Lubricant | 5.00 | 24.4 | 24.4 | 24.4 |
| Total tablet: | Oral tablet | 100.00 | 488.8 | 488.8 | 488.8 |
| Eudragit formula | Enteric coating | +12.5% weight gain | 61.2 | 61.2 | 61.2 |
| Total tablet with Enteric Coating | EC tablet | 100 | 550.0 | 550.0 | 550.0 |

Additional exemplary oral formulations can include peptide ranges from 0.25 to 36 mg of MEDI7219 (SEQ ID NO:2) and permeation enhancers in ranges from 100-300 mg Sodium Chenodeoxycholate (Na CDC) and 200-0 mg of propyl gallate (PG), in tablets containing 300 mg of permeation enhancers to 800-2400 mg Sodium Chenodeoxycholate and 1600-0 mg of propyl gallate, in tablets containing 2400 mg total amount of permeation enhancers. The ratio of permeation enhancers Na CDC:PG can be 1:2 to X:0 in no propyl gallate containing tables. Tris base and controlled release excipients (e.g. Carbopol 71G 1-10% and Carbopol 971P 0.3-3%) can be used.

TABLE 33

Examples of 4.5 mg MEDI7219 (SEQ ID NO: 2) immediate and controlled release Carbopol 971P tablet compositions (4.5 mg nominal MEDI7219 (SEQ ID NO: 2) strength).

| | Weight(mg) per tablet | | |
|---|---|---|---|
| | | Controlled release tablets | |
| Ingredient | Immediate Release tablets | 0.3% Carbopol 971P | 3.0% Carbopol 971P |
| MEDI7219 (SEQ ID NO: 2) | 5.4* | 5.4 | 5.4 |

TABLE 33-continued

Examples of 4.5 mg MEDI7219 (SEQ ID NO: 2) immediate and controlled release Carbopol 971P tablet compositions (4.5 mg nominal MEDI7219 (SEQ ID NO: 2) strength).

| | Weight(mg) per tablet | | |
|---|---|---|---|
| | | Controlled release tablets | |
| Ingredient | Immediate Release tablets | 0.3% Carbopol 971P | 3.0% Carbopol 971P |
| Sodium Chenodeoxycholate | 100.0 | 100.0 | 100.0 |
| Propyl Gallate | 200.0 | 200.0 | 200.0 |
| Mannitol | 101.8-138 | 88.1-124.3 | 75.0-111.2 |
| Tris base | 0-36.2 | 0-36.2 | 0-36.2 |
| Carbopol 971P | — | 1.5 | 14.6 |
| Crospovidone | 28.4 | 28.4 | 28.4 |
| Aerosil | 4.9 | 4.9 | 4.9 |
| Sodium Stearyl Fumarate | 12.2 | 24.4 | 12.2 |
| Total weight (mg) | 488.8 | 488.8 | 488.8 |
| EC Coated tablet weight | 550.0 | 550.0 | 550.0 |

TABLE 34

Additional examples of 4.5 mg MEDI7219 (SEQ ID NO: 2) immediate and controlled release Carbopol 971P tablet compositions (4.5 mg nominal MEDI7219 (SEQ ID NO: 2) strength).

| | Weight(mg) per tablet | | |
|---|---|---|---|
| | | Controlled release tablets | |
| Ingredient | Immediate Release tablets | 0.3% Carbopol 971P | 3.0% Carbopol 971P |
| MEDI7219 (SEQ ID NO: 2) | 5.4* | 5.4 | 5.4 |
| Sodium Chenodeoxycholate | 100.0-300.0 | 100.0-300.0 | 100.0-300.0 |
| Propyl Gallate | 200.0-0.0 | 200.0-0.0 | 200.0-0.0 |
| Mannitol | 101.8-138 | 88.1-124.3 | 75.0-111.2 |
| Tris base | 0-36.2 | 0-36.2 | 0-36.2 |
| Carbopol 971P | — | 1.5 | 14.6 |
| Crospovidone | 28.4 | 28.4 | 28.4 |
| Aerosil | 4.9 | 4.9 | 4.9 |
| Sodium Stearyl Fumarate | 12.2 | 24.4 | 12.2 |
| Total weight (mg) | 488.8 | 488.8 | 488.8 |
| EC Coated tablet weight | 550.0 | 550.0 | 550.0 |

TABLE 35

Example compositions of enterically coated immediate release (EC) and enterically coated controlled release (EC-CR) tablets.

| Ingredient | Composition, % for 488.8 mg EC tablet | Composition, % for 488.8 mg EC-CR tablet |
|---|---|---|
| Peptide | 0.256-7.364 | 0.256-7.364 |
| Sodium Chenodeoxycholate | 20.5 | 20.5 |
| Propyl Gallate | 40.9 | 40.9 |
| Mannitol | 6.833-18.903 | 6.833-18.903 |
| Tris base | 0.0-7.815 | 0.0-7.815 |
| Crospovidone, Kollidon CL | 5.81 | 5.81 |
| Carbopol | 0 | 0.3-10 |
| Aerosil 300 | 1 | 1 |
| Sodium Stearyl Fumarate | 2.00-10.00 | 2.00-10.00 |
| Total tablet: | 101 | 101 |
| Eudragit formula | +12.5% weight gain | +12.5% weight gain |
| Total tablet with Enteric Coating | 100 | 100 |

TABLE 36

Additional example compositions of enterically coated immediate release (EC) and enterically coated controlled release (EC-CR) tablets.

| Ingredient | Composition, % for 488.8 mg EC tablet | Composition, % for 488.8 mg EC-CR tablet |
|---|---|---|
| Peptide | 0.256-7.364 | 0.256-7.364 |
| Sodium Chenodeoxycholate | 20.5-61.4 | 20.5-61.4 |
| Propyl Gallate | 40.9-0 | 40.9-0 |
| Mannitol | 6.833-18.903 | 6.833-18.903 |
| Tris base | 0.0-7.815 | 0.0-7.815 |
| Crospovidone, Kollidon CL | 5.81 | 5.81 |
| Carbopol | 0 | 0.3-10 |
| Aerosil 300 | 1 | 1 |
| Sodium Stearyl Fumarate | 2.00-10.00 | 2.00-10.00 |
| Total tablet: | 101 | 101 |
| Eudragit formula | +12.5% weight gain | +12.5% weight gain |
| Total tablet with Enteric Coating | 100 | 100 |

Exemplary Eudragit enteric coating compositions formulas for (i) immediate release enterically coated tablets (pH5.5) and enterically coated controlled release tablets (pH 7.0) are shown in Table 37.

TABLE 37

Eudragit enteric coating formula composition (EC) tablets.

| Ingredient | Function | Composition, % | Notes |
|---|---|---|---|
| Eudragit | Enteric coating | 85.5 | By dry weight of polymer |
| PlasACRYL | Enteric coating plasticizer | 14.5* | PlasACRYL ™ HTP20 is a 20% aqueous suspension containing the anti-tacking agent glycerol monostearate (GMS), the plasticizer triethyl citrate (TEC) and the emulsifier polysorbate 80 |

*By dry weight of components

Example 25

Figure 11:
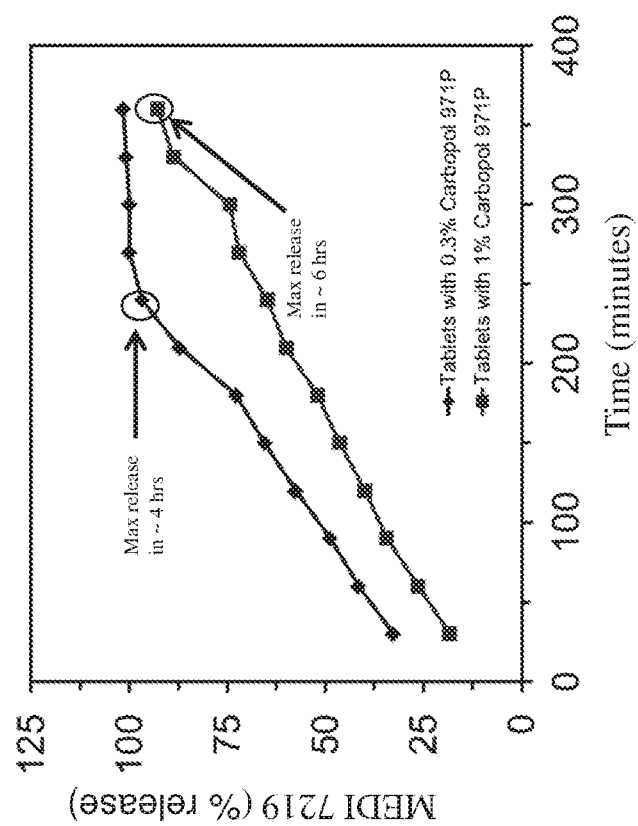
FIG. 11 shows dissolution profiles of exemplary tablet compositions. (See Example 25.)

In the following example, magnesium stearate (1%) was replaced with sodium stearyl fumarate 5%. Carbopol 71G did not give the desired release of active in the presence of sodium stearyl fumarate and therefore was replaced with powder grade Carbopol 971P. Less Carbopol 971P (0.3 and 1%) was needed to attain the same release profile as with Carbopol 71G (2.5 and 5%). Tablets were prepared at 488.8 mg weight. Examples of tablet compositions are provided in Tables 38 and 39. Example dissolution profiles are provided in FIG. 11.

TABLE 38

Example compositions of MEDI7219 (SEQ ID NO: 2) controlled release tablets.

| Ingredient | Composition, mg/tablet (0.3% Carbopol) | Composition, mg/tablet (1% Carbopol) |
|---|---|---|
| MEDI7219 (SEQ ID NO: 2) | 6 | 6 |
| Na Chenodeoxycholate | 100 | 100 |
| Propyl Gallate | 200 | 200 |
| Mannitol | 87.9 | 84.6 |
| Tris base | 36.2 | 36.2 |
| Carbopol 97IP | 1.5 | 4.8 |
| Crospovidone, Kollidon CL | 28.4 | 28.4 |
| Aerosil 300 | 4.8 | 4.8 |
| Sodium stearyl fumarate | 24 | 24 |
| Total tablet: | 488.8 | 488.8 |

TABLE 39

Additional example compositions of MEDI7219 (SEQ ID NO: 2) controlled release tablets.

| Ingredient | Composition, mg/tablet (0.3% Carbopol) | Composition, mg/tablet (1% Carbopol) |
|---|---|---|
| MEDI7219 (SEQ ID NO:2) | 6 | 6 |
| Na Chenodeoxycholate | 100-300 | 100-300 |
| Propyl Gallate | 200-0 | 200-0 |
| Mannitol | 87.9 | 84.6 |
| Tris base | 36.2 | 36.2 |
| Carbopol 97IP | 1.5 | 4.8 |
| Crospovidone, Kollidon CL | 28.4 | 28.4 |
| Aerosil 300 | 4.8 | 4.8 |
| Sodium stearyl fumarate | 24 | 24 |
| Total tablet: | 488.8 | 488.8 |

Example 26

Figure 4:
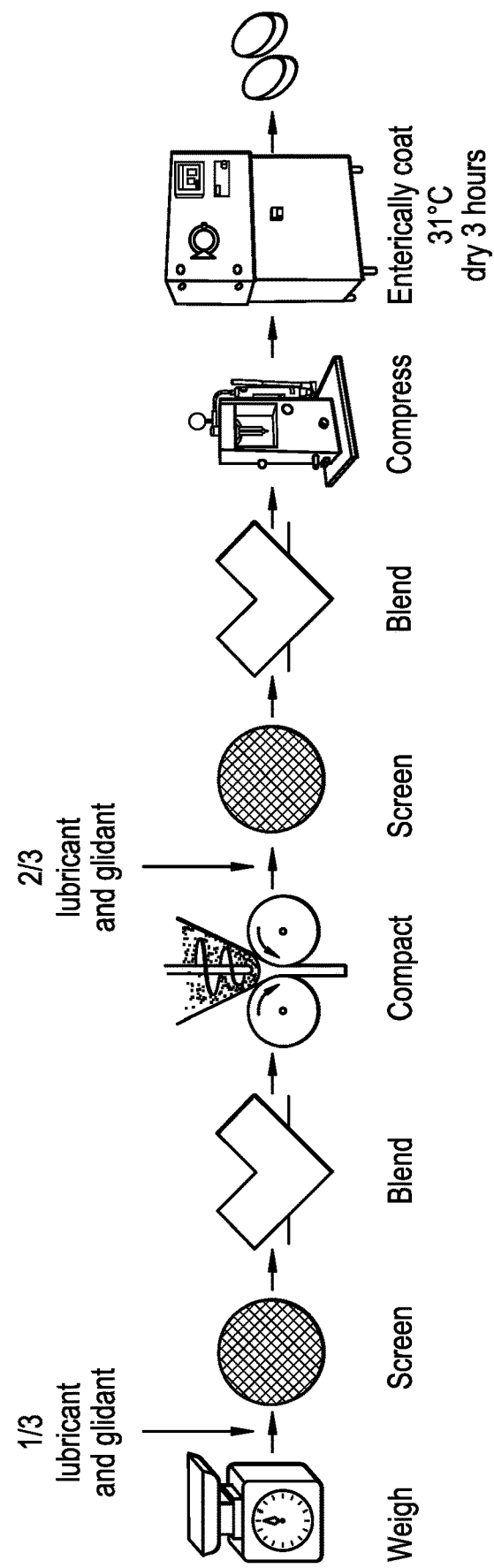
FIG. 4 shows an exemplary flow chart of tablet preparation methods tested for the development of the oral GLP-1 peptide analog formulation. (See Example 26.)

Tablet preparation is carried out as summarized in FIG. 4. All ingredients needed to make the required number of tablets are weighed. The weights of the glidant (Aerosil) are split to 0.33% and 0.66%, and the weights of the lubricant (sodium stearyl fumarate) are split to 2% and 3%. All ingredients are passed through US sieve size 34 (0.500 mm opening). Weigh MEDI7219 (SEQ ID NO:2) and mannitol (10 times MEDI7219 (SEQ ID NO:2)) and pass through sieve #60 (0.250 mm opening). Rub and tap with spatula to recover any clogged material. Weigh the remaining amount of mannitol and pass it through the same sieve #60 to rinse out all the MEDI7219 (SEQ ID NO:2) from the sieve. Weigh propyl gallate, Tris base and Pruv (intragranular) and pass through sieve No. 35 and mix with above blend from step 2 in Turbula mixer for 10 minutes. Weigh sodium chenodeoxycholate, crospovidone and Aerosil® (intragranular), pass them through sieve #35 and mix with the above blend in Turbula mixer for 10 minutes. Dry granulation is performed by compressing the blend using a pellet machine and using the same amount of power to make pellet every time. An instant release pellet machine can be used for slugging that has a diameter of 12 mm. The thickness of the slugs is about 5 mm and the hardness is about 20 N. After compression for dry granulation, the compressed slug is passed through a US sieve size with 1 mm opening. Weigh Aerosil (extragranular), pass through sieve #35 and mix with above blend in Turbula mixer for 5 minutes. Weigh Pruv (extragranular), pass through sieve #35 and finally mix with the above blend in Turbula mixer for 30 minutes. Make the tablets of 488.8 mg tablet weight using 8×15 mm oval concave punches or 244.4 mg using a 6×11 mm oval concave punches. Pressure is applied to compress the power to achieve a hardness of 40-50N.

For the preparation of enterically coated controlled release (EC-CR) tablets, the controlled release polymer (Carbopol) is added along with the sodium chenodeoxycholate, Tris base, Crospovidone, and 0.33% Aerosil, prior to the roller compaction.

The tablet characterization and specification in process parameters, before applying enteric coating, (488.8 mg tablets) are shown in Table 40 below.

TABLE 40

Tablet characterization and specification process parameters (488.8 mg tablets).

| Attribute | Method | Acceptance Criteria |
|---|---|---|
| Hardness (Newtons) | Hardness tester | 40-55 N |
| Thickness (mm) | Vernier caliper | 5.60-5.90 mm |
| Disintegration time (mins) | Disintegration apparatus | 5-17 minutes |
| Uncoated Tablet weight (mg) | Weighing balance | 488.8 mg ± 5% |
| Friability (%) | Weighing balance | ≤1.0% |
| Weight Gain during coating | Weighing balance | 11-13% |

Figure 5:
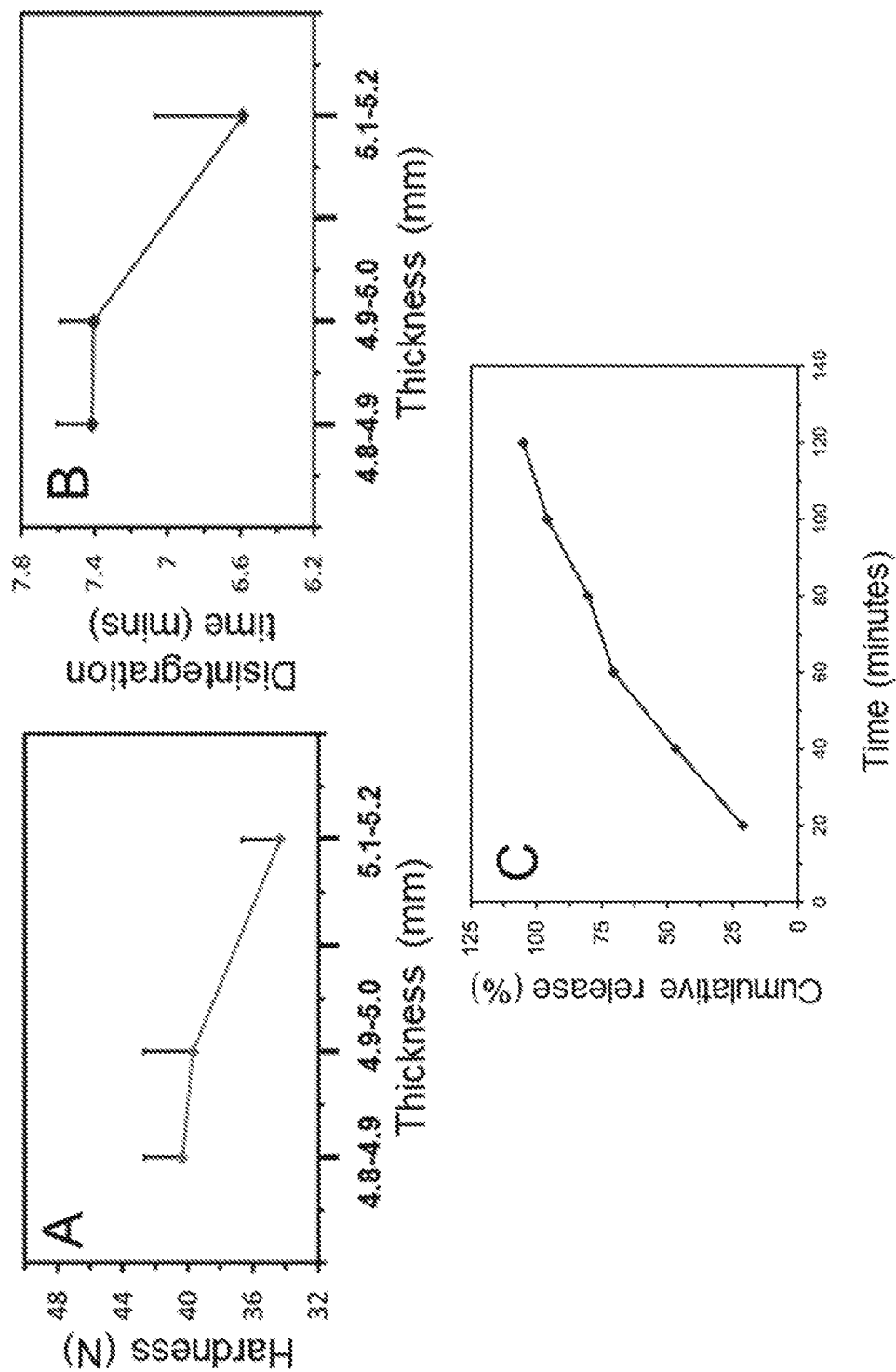
FIG. 5 shows (A) hardness values attained and its relation to the thickness of the tablets, (B) disintegration time attained and its relation to the thickness of the tablets, and (C) a typical dissolution profile for uncoated tablets. (See Example 26.)

An Example of 244.4 mg uncoated immediate release tablets hardness (A) and disintegration time (B) in comparison to increasing tablet thickness is shown in FIG. 5. FIG. 5C shows the cumulative release profile of an uncoated tablets.

Enteric coating is performed using a Vector LDCS3 pan coater equipped with 1.3 L pan. Exhaust temperature is set at ≤31° C. An inlet temperature set at 45° C. can attain the desired exhaust temperature. Inlet air flow is set at >10 CFM. Pan speed is set at 8-10 rpm. Spray rate is approximately 4 g/min. Drying time after coating is complete is about 3 hours. Weight gain for coated tablets 11-13%. Table 41 below provides a comparison of enterically coated immediate release and controlled release 244.4 mg tablets in process release specifications.

TABLE 41

Comparison of in process parameters (before enteric coating) for immediate release and controlled release 244.4 mg tablets in process release specifications

| Attribute | Method | Acceptance Criteria | | |
|---|---|---|---|---|
| | | EC | 0.3% EC CR | 1% EC CR |
| Hardness (Newtons) | Hardness tester | 40-50 N | 40-50 N | 40-50 N |
| Thickness (mm) | Vernier caliper | 5.17-5.66 mm | 5.10-5.35 mm | 5.10-5.35 mm |
| Disintegration time (mins) | Disintegration apparatus | 8.5-11 minutes | 40-50 minutes | 70-80 minutes |
| Tablet weight (mg) | Weighing balance | 244.4 mg ± 5% | 244.4 mg ± 5% | 244.4 mg ± 5% |
| Friability (%) | Weighing balance | ≤1.0% | ≤1.0% | ≤1.0% |
| Weight Gain during coating (%) | Weighing balance | 11-13% | 11-13% | 11-13% |

Dissolution Parameters:
a. Stability in 0.1N HCl: less than 5% of active released after 2 hours
b. Dissolution rate EC-IR tablets: Not less than 75%% dissolution in 60 minutes
c. Dissolution rate EC-CR tablets: 100% release in under 4 hours for 1% Carbopol 71G or 0.3% Carbopol 971P and under 6 hours for 3% Carbopol 71G or 1.0% Carbopol 971P.

Example 27

Additional exemplary tablets for administration to humans without Tris are provided in Table 42.

TABLE 42

| MEDI7219 Dose Strength | NaCDC (mg) | PG (mg) | NaCDC:PG ratio | Carbopol |
|---|---|---|---|---|
| 3 mg | 100 | 200 | 1:2 | 0.9% |
| 12 mg | 100 | 200 | 1:2 | 0.9% |
| 36 mg | 100 | 200 | 1:2 | 0.9% |
| 3 mg | 150 | 150 | 1:1 | 0.9% |
| 12 mg | 150 | 150 | 1:1 | 0.9% |
| 36 mg | 150 | 150 | 1:1 | 0.9% |
| 3 mg | 200 | 100 | 2:1 | 0.9% |
| 12 mg | 200 | 100 | 2:1 | 0.9% |
| 36 mg | 200 | 100 | 2:1 | 0.9% |
| 3 mg | 260 | 40 | 6.5 | 0.9% |
| 12 mg | 260 | 40 | 6.5 | 0.9% |
| 36 mg | 260 | 40 | 6.5 | 0.9% |
| 3 mg | 280 | 20 | 14:1 | 0.9% |
| 12 mg | 280 | 20 | 14:1 | 0.9% |
| 36 mg | 280 | 20 | 14:1 | 0.9% |
| 3 mg | 290 | 10 | 29:1 | 0.9% |
| 12 mg | 290 | 10 | 29:1 | 0.9% |
| 36 mg | 290 | 10 | 29:1 | 0.9% |
| 3 mg | 299 | 2 | 145:1 | 0.9% |
| 12 mg | 299 | 2 | 145:1 | 0.9% |
| 36 mg | 299 | 2 | 145:1 | 0.9% |
| 3 mg | 300 | 1 | | 0.9% |
| 12 mg | 300 | 1 | | 0.9% |
| 36 mg | 300 | 1 | | 0.9% |
| 3 mg | 100 | 200 | 1:2 | 0.3% |
| 12 mg | 100 | 200 | 1:2 | 0.3% |
| 36 mg | 100 | 200 | 1:2 | 0.3% |
| 3 mg | 150 | 150 | 1:1 | 0.3% |
| 12 mg | 150 | 150 | 1:1 | 0.3% |
| 36 mg | 150 | 150 | 1:1 | 0.3% |
| 3 mg | 200 | 100 | 2:1 | 0.3% |
| 12 mg | 200 | 100 | 2:1 | 0.3% |
| 36 mg | 200 | 100 | 2:1 | 0.3% |

TABLE 42-continued

| MEDI7219 Dose Strength | NaCDC (mg) | PG (mg) | NaCDC:PG ratio | Carbopol |
|---|---|---|---|---|
| 3 mg | 260 | 40 | 6.5 | 0.3% |
| 12 mg | 260 | 40 | 6.5 | 0.3% |
| 36 mg | 260 | 40 | 6.5 | 0.3% |
| 3 mg | 280 | 20 | 14:1 | 0.3% |
| 12 mg | 280 | 20 | 14:1 | 0.3% |
| 36 mg | 280 | 20 | 14:1 | 0.3% |
| 3 mg | 290 | 10 | 29:1 | 0.3% |
| 12 mg | 290 | 10 | 29:1 | 0.3% |
| 36 mg | 290 | 10 | 29:1 | 0.3% |
| 3 mg | 299 | 2 | 145:1 | 0.3% |
| 12 mg | 299 | 2 | 145:1 | 0.3% |
| 36 mg | 299 | 2 | 145:1 | 0.3% |
| 3 mg | 300 | 1 | | 0.3% |
| 12 mg | 300 | 1 | | 0.3% |
| 36 mg | 300 | 1 | | 0.3% |
| 3 mg | 100 | 200 | 1:2 | 1.2% |
| 12 mg | 100 | 200 | 1:2 | 1.2% |
| 36 mg | 100 | 200 | 1:2 | 1.2% |
| 3 mg | 150 | 150 | 1:1 | 1.2% |
| 12 mg | 150 | 150 | 1:1 | 1.2% |
| 36 mg | 150 | 150 | 1:1 | 1.2% |
| 3 mg | 200 | 100 | 2:1 | 1.2% |
| 12 mg | 200 | 100 | 2:1 | 1.2% |
| 36 mg | 200 | 100 | 2:1 | 1.2% |
| 3 mg | 260 | 40 | 6.5 | 1.2% |
| 12 mg | 260 | 40 | 6.5 | 1.2% |
| 36 mg | 260 | 40 | 6.5 | 1.2% |
| 3 mg | 280 | 20 | 14:1 | 1.2% |
| 12 mg | 280 | 20 | 14:1 | 1.2% |
| 36 mg | 280 | 20 | 14:1 | 1.2% |
| 3 mg | 290 | 10 | 29:1 | 1.2% |
| 12 mg | 290 | 10 | 29:1 | 1.2% |
| 36 mg | 290 | 10 | 29:1 | 1.2% |
| 3 mg | 299 | 2 | 145:1 | 1.2% |

TABLE 42-continued

| MEDI7219 Dose Strength | NaCDC (mg) | PG (mg) | NaCDC:PG ratio | Carbopol |
|---|---|---|---|---|
| 12 mg | 299 | 2 | 145:1 | 1.2% |
| 36 mg | 299 | 2 | 145:1 | 1.2% |
| 3 mg | 300 | 1 | | 1.2% |
| 12 mg | 300 | 1 | | 1.2% |
| 36 mg | 300 | 1 | | 1.2% |

Example 28

The efficacy of sodium caprate as a permeation enhancer was also evaluated. Sodium caprate is a C10 saturated fatty acid sodium salt that is believed to increase permeability by loosening tight junctions. In vivo studies in dogs demonstrated that the bioavailabilty of MEDI7219 in enterically coated tablets containing sodium caprate was comparable to the bioavailability of MEDI7219 in tables with NaCDC and propyl gallate. (See Table 27, above). Sodium caprate and NaCDC/PG also resulted in similar exposures of MEDI7219 (Cmax and AUC), similar half-lives, and similar median times to reach Cmax. See Table 43.

TABLE 43

MEDI7219 exposure based on tablet components

| Parameter | 300 mg Na Caprate; 20 mg MEDI7219 | 300 mg Na CDC/PG; 20 mg MEDI7219 |
|---|---|---|
| $T_{1/2}$ (hr) | 10.6 (16.8) | 9.76 (13.2) |
| $T_{max}$ (hr) | 1.5 (1.5-2.0) | 1.5 (1.0-4.5) |
| $C_{max}$ (ng/mL) | 924 (47.5) | 1450 (63.2) |
| $AUC_{0-last}$ (ng · hr/mL) | 10200 (58.6) | 13500 (54.3) |
| $AUC_{0-inf}$ (ng · hr/mL) | 10200 (58.6) | 13500 (54.2) |
| dn- $AUC_{0-inf}$ (ng · hr/mL/mg) | 509 (58.6) | 676 (54.2) |
| CL/F (mL/hr) | 2390 (40.9) | 1880 (52.1) |
| F (%) | 4.46 (58.6) | 5.92 (54.2) |

Additional exemplary sodium caprate tablet formulations are provided in Table 44.

TABLE 44

Sodium caprate based MEDI7219 formulations

| Group | No. of Males | MEDI7219 and PE dose levels per tablet | Peptide dose level | Na Caprate dose level | Dose amount |
|---|---|---|---|---|---|
| 1 | 5 | 1.0 mg MEDI7219<br>150 mg Na Caprate<br>pH 5.5 enteric coating | 1 mg/dog | 150 mg/dog | 1 tablet/dog |
| 2 | 5 | 1.0 mg MEDI7219<br>150 mg Na Caprate<br>pH 5.5 enteric coating | 3 mg/dog | 450 mg/dog | 3 tablets/dog |
| 3 | 5 | 3.0 mg MEDI7219<br>150 mg Na Caprate<br>pH 5.5 enteric coating | 3 mg/dog | 150 mg/dog | 1 tablet/dog |
| 4 | 5 | 3.0 mg MEDI7219<br>150 mg Na Caprate<br>pH 5.5 enteric coating | 6 mg/dog | 300 mg/dog | 2 tablets/dog |
| 5 | 5 | 3.0 mg MEDI7219<br>150 mg Na Caprate<br>pH 5.5 enteric coating | 9 mg/dog | 450 mg/dog | 3 tablets/dog |
| 6 | 5 | 10.0 mg MED 17219<br>150 mg Na Caprate<br>pH 5.5 enteric coating | 10 mg/dog | 150 mg/dog | 1 tablet/dog |
| 7 | 5 | 3.0 mg MEDI7219<br>150 mg Na Caprate<br>pH 7.0 enteric coating<br>0.9% Carbopol | 3 mg/dog | 150 mg/dog | 1 tablet/dog |
| 8 | 5 | 3.0 mg MEDI7219<br>50 mg Na CDC<br>100 mg PG<br>pH 5.5 enteric coating | 3 mg/dog | 150 mg/dog | 1 tablet/dog |

Figure 14:
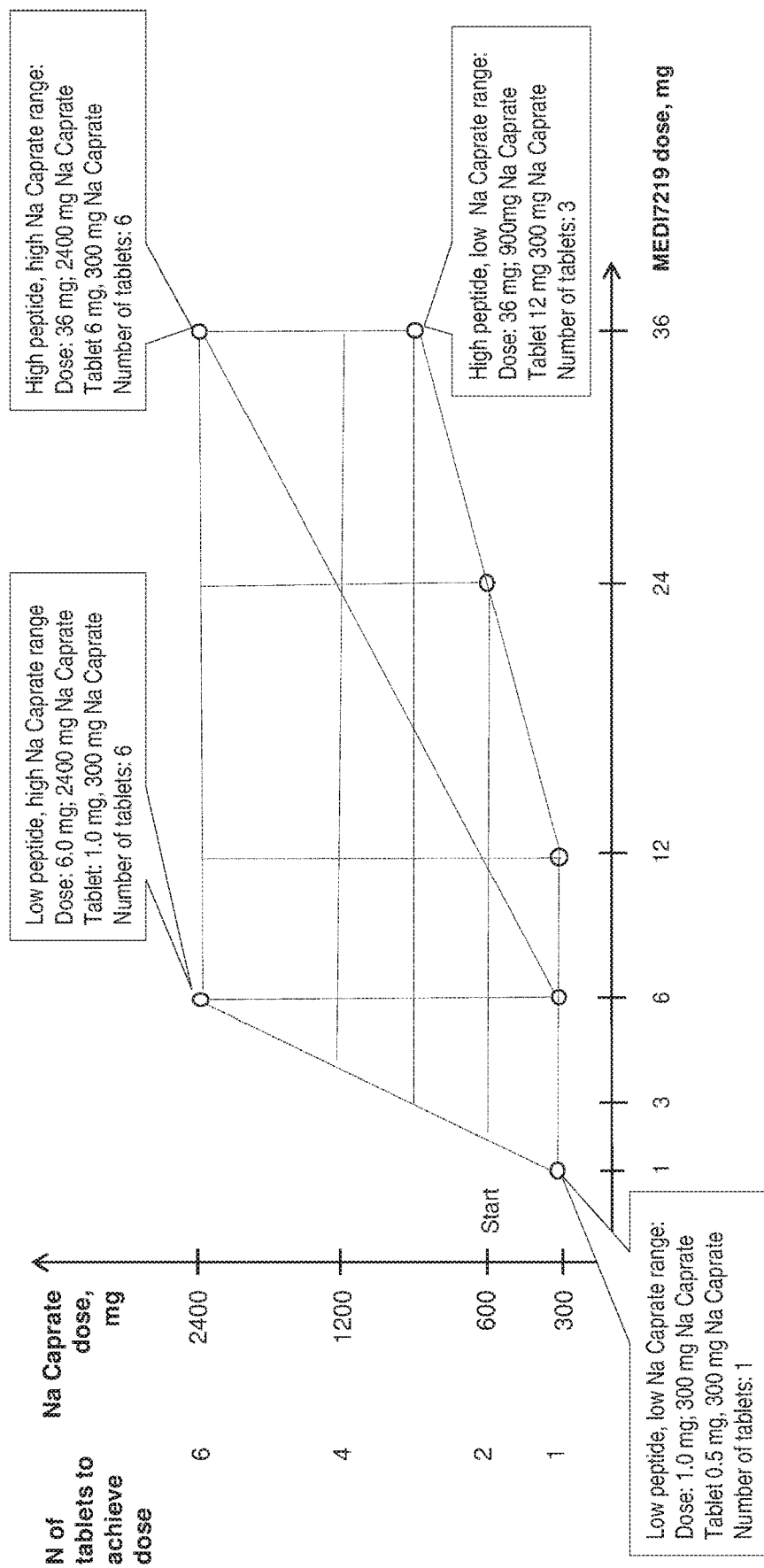
FIG. 14 shows the clinical formulation design space and ranges for enterically coated tablets containing sodium caprate. (See Example 28.)

The clinical formulation design space and ranges for exemplary enterically coated tablets comprising sodium caprate for administration to humans is shown in FIG. 14.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

All publications, patents, patent applications, and/or other documents cited in this application are incorporated by

What is claimed is:

1. A pharmaceutical composition for oral administration comprising (i) a bislipidated GLP-1 peptide analog and (ii) sodium chenodeoxycholate.

2. A pharmaceutical composition for oral administration comprising (i) a bislipidated GLP-1 peptide analog and (ii) propyl gallate.

3. The pharmaceutical composition of claim 2, further comprising sodium chenodeoxycholate.

4. The pharmaceutical composition of claim 3, wherein the ratio of sodium chenodeoxycholate to propyl gallate is 150:1 to 1:4.

5. The pharmaceutical composition of claim 4, wherein the ratio of sodium chenodeoxycholate to propyl gallate is 145:1.

6. The pharmaceutical composition of claim 4, wherein the ratio of sodium chenodeoxycholate to propyl gallate is 29:1.

7. The pharmaceutical composition of claim 4, wherein the ratio of sodium chenodeoxycholate to propyl gallate is 14:1.

8. The pharmaceutical composition of claim 4, wherein the ratio of sodium chenodeoxycholate to propyl gallate is 6.5:1.

9. The pharmaceutical composition of claim 4, wherein the ratio of sodium chenodeoxycholate to propyl gallate is 4:1.

10. The pharmaceutical composition of claim 4, wherein the ratio of sodium chenodeoxycholate to propyl gallate is 2:1.

11. The pharmaceutical composition of claim 4, wherein the ratio of sodium chenodeoxycholate to propyl gallate is 1:1.

12. The pharmaceutical composition of claim 3, wherein the ratio of sodium chenodeoxycholate to propyl gallate is 2:1 to 1:4.

13. The pharmaceutical composition of claim 12, wherein the ratio of sodium chenodeoxycholate to propyl gallate is 1:2.

14. The pharmaceutical composition of claim 1, wherein the amount of sodium chenodeoxycholate is about 1 mg to about 1500 mg.

15. The pharmaceutical composition of claim 14, wherein the amount of sodium chenodeoxycholate is about 100 mg to about 800 mg.

16. The pharmaceutical composition of claim 14, wherein the amount of sodium chenodeoxycholate is about 100 mg, about 200 mg, about 300 mg, about 400 mg, about 500 mg, about 600 mg, about 700 mg, or about 800 mg.

17. The pharmaceutical composition of claim 14, wherein the amount of sodium chenodeoxycholate is about 50 mg, about 65 mg, about 120 mg, about 130 mg, about 140 mg, about 150 mg, about 260 mg, about 280 mg, about 290 mg, or about 299 mg.

18. The pharmaceutical composition of claim 14, wherein the amount of sodium chenodeoxycholate is about 100 mg.

19. The pharmaceutical composition of claim 1, wherein sodium chenodeoxycholate is about 15% to about 25% of the pharmaceutical composition by weight.

20. The pharmaceutical composition of claim 19, wherein sodium chenodeoxycholate is about 20% to about 21% of the pharmaceutical composition by weight.

21. The pharmaceutical composition of claim 1, wherein sodium chenodeoxycholate is about 15% to about 65% of the pharmaceutical composition by weight, optionally wherein sodium chenodeoxycholate is about 30% to about 65% of the pharmaceutical composition by weight.

22. The pharmaceutical composition of claim 2, wherein the amount of propyl gallate is about 1 mg to about 3000 mg.

23. The pharmaceutical composition of claim 22, wherein the amount of propyl gallate is about 200 mg to about 1600 mg.

24. The pharmaceutical composition of claim 22, wherein the amount of propyl gallate is about 2 mg, about 10 mg, about 20 mg, about 30 mg, about 40 mg, about 50 mg, about 100 mg, about 150 mg, or about 200 mg.

25. The pharmaceutical composition of claim 22, wherein the amount of propyl gallate is about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, or about 1600 mg.

26. The pharmaceutical composition of claim 22, wherein the amount of propyl gallate is about 200 mg.

27. The pharmaceutical composition of claim 2, wherein propyl gallate is about 45% to about 55% of the pharmaceutical composition by weight.

28. The pharmaceutical composition of claim 27, wherein propyl gallate is about 40% to about 41% of the pharmaceutical composition by weight.

29. The pharmaceutical composition of claim 1, wherein the pharmaceutical composition does not comprise propyl gallate.

30. A pharmaceutical composition for oral administration comprising a bislipidated GLP-1 peptide analog and sodium caprate.

31. The pharmaceutical composition of claim 30, wherein the composition comprises about 300 mg to about 2400 mg of sodium caprate.

32. The pharmaceutical composition of claim 31, wherein the composition comprises about 300 mg of sodium caprate.

33. The pharmaceutical composition of claim 31, wherein the composition comprises about 600 mg of sodium caprate.

34. The pharmaceutical composition of claim 31, wherein the composition comprises about 900 mg of sodium caprate.

35. The pharmaceutical composition of claim 31, wherein the composition comprises about 1200 mg of sodium caprate.

36. The pharmaceutical composition of claim 31, wherein the composition comprises about 2400 mg of sodium caprate.

37. The pharmaceutical composition of claim 31, wherein the amount of the GLP-1 peptide analog is about 0.1 mg to about 100 mg.

38. The pharmaceutical composition of claim 37, wherein the amount of the GLP-1 peptide analog is about 0.0625 mg to about 36 mg.

39. The pharmaceutical composition of claim 38, wherein the amount of the GLP-1 peptide analog is about 0.25 mg to about 36 mg.

40. The pharmaceutical composition of claim 39, wherein the amount of the GLP-1 peptide analog is about 0.125 mg, about 4.5 mg, or about 36 mg.

41. The pharmaceutical composition of claim 40, wherein the GLP-1 peptide analog is about 0.2% to about 10% of the pharmaceutical composition by weight.

\* \* \* \* \*

SEQUENCE LISTING

```
<160> NUMBER OF SEQ ID NOS: 15

<210> SEQ ID NO 1
<211> LENGTH: 30
<212> TYPE: PRT
<213> ORGANISM: Artificial Sequence
<220> FEATURE:
<223> OTHER INFORMATION: GLP-1 7-36

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: AIB
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys((Peg)2-(Peg)2-gamma-Glu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys((PEG)2-(PEG)2-gammaGlu-Lauroyl)

<400> SEQUENCE: 2

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: aib
<220> FEATURE:
```

```
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys((Peg)2-(Peg)2-gamma-Glu-stearate)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 3

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys((Peg)2-(Peg)2-gamma-Glu-stearate)
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 4

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
```

```
                  20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys((PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys((PEG)2-(PEG)2-gammaGlu-Lauroyl)

<400> SEQUENCE: 5

His Xaa Glu Gly Ser Phe Thr Ser Asp Val Ser Lys Tyr Leu Glu Gly
1               5                   10                  15

Glu Ala Ala Lys Glu Phe Ile Ala Lys Val Val Glu Gly Gly
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys((PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys((PEG)2-(PEG)2-gammaGlu-Lauroyl)

<400> SEQUENCE: 6

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30
```

```
<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys((PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (26)..(26)
<223> OTHER INFORMATION: Lys((PEG)2-(PEG)2-gammaGlu-Lauroyl)

<400> SEQUENCE: 7

His Xaa Glu Gly Ser Phe Thr Ser Asp Val Ser Lys Tyr Leu Glu Gly
1               5                   10                  15

Glu Ala Ala Lys Glu Phe Ile Ala Trp Lys Val Glu Gly Gly
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Description of Artificial Sequence: Synthetic
      Polypeptide
<220> FEATURE:
<221> NAME/KEY: MOD_RES
<222> LOCATION: (2)..(2)
<223> OTHER INFORMATION: MOD_RES
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys((PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys((PEG)2-(PEG)2-gammaGlu-Lauroyl)

<400> SEQUENCE: 8

His Xaa Glu Gly Ser Phe Thr Ser Asp Lys Ser Ser Tyr Leu Glu Gly
1               5                   10                  15

Glu Ala Ala Lys Glu Phe Ile Lys Trp Val Val Glu Gly Gly
            20                  25                  30

<210> SEQ ID NO 9
<211> LENGTH: 30
<212> TYPE: PRT
```

```
<213> ORGANISM: Artificial Sequence
<220> FEATURE:
<223> OTHER INFORMATION: Description of Artificial Sequence: Synthetic
      Polypeptide
<220> FEATURE:
<221> NAME/KEY: MOD_RES
<222> LOCATION: (2)..(2)
<223> OTHER INFORMATION: aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys((PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys((PEG)2-(PEG)2-gammaGlu-Lauroyl)

<400> SEQUENCE: 9

His Xaa Glu Gly Ser Phe Thr Ser Asp Val Ser Ser Tyr Lys Glu Gly
1               5                   10                  15

Glu Ala Ala Lys Glu Phe Ile Ala Lys Val Val Glu Gly Gly
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: Description of Artificial Sequence: Synthetic
      Polypeptide
<220> FEATURE:
<221> NAME/KEY: MOD_RES
<222> LOCATION: (2)..(2)
<223> OTHER INFORMATION: aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys((PEG)2-(PEG)2-gammaGlu-Palmitoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys((PEG)2-(PEG)2-gammaGlu-Palmitoyl)

<400> SEQUENCE: 10

His Xaa Glu Gly Ser Phe Thr Ser Asp Val Ser Ser Lys Leu Glu Gly
1               5                   10                  15
```

```
Glu Ala Ala Lys Glu Phe Ile Ala Lys Val Val Glu Gly Gly
            20                  25                  30

<210> SEQ ID NO 11
<211> LENGTH: 31
<212> TYPE: PRT
<213> ORGANISM: Artificial Sequence
<220> FEATURE:
<223> OTHER INFORMATION: Description of Artificial Sequence: Synthetic
      Polypeptide
<220> FEATURE:
<221> NAME/KEY: MOD_RES
<222> LOCATION: (2)..(2)
<223> OTHER INFORMATION: aib
<220> FEATURE:
<221> NAME/KEY: MOD_RES
<222> LOCATION: (20)..(20)
<223> OTHER INFORMATION: AEEAc-AEEAc-Gamma-Glu-17-carboxyheptadecanoyl

<400> SEQUENCE: 11

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence: Synthetic
      Polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: Tyr(OMe)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 12

His Xaa Glu Gly Ser Phe Thr Ser Asp Val Ser Ser Lys Leu Glu Gly
1               5                   10                  15

Glu Ala Ala Lys Glu Tyr Ile Ala Lys Val Val Glu Gly Gly
            20                  25                  30

<210> SEQ ID NO 13
<211> LENGTH: 30
<212> TYPE: PRT
<213> ORGANISM: Artificial Sequence
<220> FEATURE:
```

```
<223> OTHER INFORMATION: Description of Artificial Sequence: Synthetic
      Polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 13

His Xaa Glu Gly Ser Phe Thr Ser Asp Val Ser Ser Lys Leu Glu Gly
1               5                   10                  15

Glu Ala Ala Lys Glu Xaa Ile Ala Lys Val Val Glu Gly Gly
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: Description of Artificial Sequence: Synthetic
      Polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Myristoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Myristoyl)

<400> SEQUENCE: 14

His Xaa Glu Gly Ser Phe Thr Ser Asp Val Ser Ser Lys Leu Glu Gly
```

```
                1               5                  10                 15
            Glu Ala Ala Lys Glu Phe Ile Ala Lys Val Val Glu Gly Gly
                            20              25              30

<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Stearoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Stearoyl)

<400> SEQUENCE: 15

His Xaa Glu Gly Ser Phe Thr Ser Asp Val Ser Ser Lys Leu Glu Gly
            1               5                   10                  15

Glu Ala Ala Lys Glu Phe Ile Ala Lys Val Val Glu Gly Gly
                            20              25              30
```